(12) United States Patent
Olejnik et al.

(10) Patent No.: US 7,524,941 B2
(45) Date of Patent: Apr. 28, 2009

(54) METHODS FOR THE PREPARATION OF CHEMICALLY MISAMINOACYLATED TRNA VIA PROTECTIVE GROUPS

(75) Inventors: Jerzy Olejnik, Brookline, MA (US); Edyta Krzymanska-Olejnik, Brookline, MA (US); Sergey Mamaev, West Roxbury, MA (US); Kenneth J. Rothschild, Newton, MA (US)

(73) Assignee: Ambergen, Inc., Watertown, MA (US)

( * ) Notice: Subject to any disclaimer, the term of this patent is extended or adjusted under 35 U.S.C. 154(b) by 38 days.

(21) Appl. No.: 11/900,323

(22) Filed: Sep. 11, 2007

(65) Prior Publication Data

US 2008/0287710 A1    Nov. 20, 2008

(51) Int. Cl.
| | |
|---|---|
| C07C 245/00 | (2006.01) |
| C07C 291/00 | (2006.01) |
| C12Q 1/68 | (2006.01) |
| C07K 14/00 | (2006.01) |
| G01N 33/00 | (2006.01) |
| C07H 21/04 | (2006.01) |

(52) U.S. Cl. .............. 534/554; 534/557; 534/570; 435/6; 435/7.1; 435/7.2; 530/350; 536/23.1; 436/86

(58) Field of Classification Search .............. 435/6, 435/7.1, 7.2; 530/350; 536/23.1; 436/86; 534/554, 557, 570

See application file for complete search history.

*Primary Examiner*—Jezia Riley
(74) *Attorney, Agent, or Firm*—Medlen & Carroll, LLP

(57) ABSTRACT

The present invention relates to methods for the preparation of chemically aminoacylated tRNAs for the purpose of introduction of markers into nascent proteins. The present invention also relates to methods for the non-radioactive labeling, detection, quantitation and isolation of nascent proteins translated in a cellular or cell-free translation system utilizing chemically aminoacylated tRNAs. tRNA molecules are misaminoacylated with non-radioactive markers which may be non-native amino acids, amino acid analogs or derivatives. Markers may comprise cleavable moieties, detectable labels, reporter properties wherein markers incorporated into protein can be distinguished from unincorporated markers, or coupling agents which facilitate the detection and isolation of nascent protein from other components of the translation system.

15 Claims, 64 Drawing Sheets

| AMBER-1 PROTEIN | FLUOROPHORE INCORPORATION [%] | PROTEIN YIELD |
| --- | --- | --- |
| α-HEMOLYSIN | 53% | 10 μg/ml |
| CALMODULIN | 67% | 7 μg/ml |
| GLUTATHIONE S-TRANSFERASE (GST) | 27% | 5 μg/ml |

FIG. 53C

METHODS FOR THE PREPARATION OF CHEMICALLY MISAMINOACYLATED TRNA VIA PROTECTIVE GROUPS

FIELD OF THE INVENTION

This invention relates to the preparation of chemically aminoacylated tRNAs for the purpose of introduction of markers into nascent proteins. The invention also relates to methods for the non-radioactive labeling, detection, quantitation and isolation of nascent proteins translated in a cellular or cell-free translation systems utilizing chemically aminoacylated tRNAs.

BACKGROUND OF THE INVENTION

Cells contain organelles, macromolecules and a wide variety of small molecules. Except for water, the vast majority of the molecules and macromolecules can be classified as lipids, carbohydrates, proteins or nucleic acids. Proteins are the most abundant cellular components and facilitate many of the key cellular processes. They include enzymes, antibodies, hormones, transport molecules and components for the cytoskeleton of the cell.

Proteins are composed of amino acids arranged into linear polymers or polypeptides. In living systems, proteins comprise over twenty common amino acids. These twenty or so amino acids are generally termed the native amino acids. At the center of every amino acid is the alpha carbon atom ($C\alpha$) which forms four bonds or attachments with other molecules. One bond is a covalent linkage to an amino group ($NH_2$) and another to a carboxyl group (COOH) which both participate in polypeptide formation. A third bond is nearly always linked to a hydrogen atom and the fourth to a side chain which imparts variability to the amino acid structure. For example, alanine is formed when the side chain is a methyl group ($—CH_3$) and a valine is formed when the side chain is an isopropyl group ($—CH(CH_3)_2$). It is also possible to chemically synthesize amino acids containing different side-chains, however, the cellular protein synthesis system, with rare exceptions, utilizes native amino acids. Other amino acids and structurally similar chemical compounds are termed non-native and are generally not found in most organisms.

A central feature of all living systems is the ability to produce proteins from amino acids. Basically, protein is formed by the linkage of multiple amino acids via peptide bonds. Key molecules involved in this process are messenger RNA (mRNA) molecules, transfer RNA (tRNA) molecules and ribosomes (rRNA-protein complexes). Protein translation normally occurs in living cells and in some cases can also be performed outside the cell in systems referred to as cell-free translation systems. In either system, the basic process of protein synthesis is identical. The extra-cellular or cell-free translation system comprises an extract prepared from the intracellular contents of cells. These preparations contain those molecules which support protein translation and depending on the method of preparation, post-translational events such as glycosylation and cleavages as well. Typical cells from which cell-free extracts or in vitro extracts are made are *Escherichia coli* cells, wheat germ cells, rabbit reticulocytes, insect cells and frog oocytes.

Both in vivo and in vitro syntheses involve the reading of a sequence of bases on a mRNA molecule. The mRNA contains instructions for translation in the form of triplet codons. The genetic code specifies which amino acid is encoded by each triplet codon. For each codon which specifies an amino acid, there normally exists a cognate tRNA molecule which functions to transfer the correct amino acid onto the nascent polypeptide chain. The amino acid tyrosine (Tyr) is coded by the sequence of bases UAU and UAC, while cysteine (Cys) is coded by UGU and UGC. Variability associated with the third base of the codon is common and is called wobble.

Translation begins with the binding of the ribosome to mRNA (See FIG. 1). A number of protein factors associate with the ribosome during different phases of translation including initiation factors, elongation factors and termination factors. Formation of the initiation complex is the first step of translation. Initiation factors contribute to the initiation complex along with the mRNA and initiator tRNA (fmet and met) which recognizes the base sequence UAG. Elongation proceeds with charged tRNAs binding to ribosomes, translocation and release of the amino acid cargo into the peptide chain. Elongation factors assist with the binding of tRNAs and in elongation of the polypeptide chain with the help of enzymes like peptidyl transferase. Termination factors recognize a stop signal, such as the base sequence UGA, in the message terminating polypeptide synthesis and releasing the polypeptide chain and the mRNA from the ribosome.

The structure of tRNA is often shown as a cloverleaf representation (See, e.g., FIGS. 1 & 2). Structural elements of a typical tRNA include an acceptor stem, a D-loop, an anticodon loop, a variable loop and a TΨC loop. Aminoacylation or charging of tRNA results in linking the carboxyl terminal of an amino acid to the 2'-(or 3'-)hydroxyl group of a terminal adenosine base via an ester linkage. This process can be accomplished either using enzymatic or chemical methods. Normally a particular tRNA is charged by only one specific native amino acid. This selective charging, termed here enzymatic aminoacylation, is accomplished by aminoacyl tRNA synthetases. A tRNA which selectively incorporates a tyrosine residue into the nascent polypeptide chain by recognizing the tyrosine UAC codon will be charged by tyrosine with a tyrosine-aminoacyl tRNA synthetase, while a tRNA designed to read the UGU codon will be charged by a cysteine-aminoacyl tRNA synthetase. These synthetases have evolved to be extremely accurate in charging a tRNA with the correct amino acid to maintain the fidelity of the translation process. Except in special cases where the non-native amino acid is very similar structurally to the native amino acid, it is necessary to use means other than enzymatic aminoacylation to charge a tRNA.

Molecular biologists routinely study the expression of proteins that are coded for by genes. A key step in research is to express the products of these genes either in intact cells or in cell-free extracts. Conventionally, molecular biologists use radioactively labeled amino acid residues such as $^{35}$S-methionine as a means of detecting newly synthesized proteins or so-called nascent proteins. These nascent proteins can normally be distinguished from the many other proteins present in a cell or a cell-free extract by first separating the proteins by the standard technique of gel electrophoresis and determining if the proteins contained in the gel possess the specific radioactively labeled amino acids. This method is simple and relies on gel electrophoresis, a widely available and practiced method. It does not require prior knowledge of the expressed protein and in general does not require the protein to have any special properties. In addition, the protein can exist in a denatured or unfolded form for detection by gel electrophoresis. Furthermore, more specialized techniques such as blotting to membranes and coupled enzymatic assays are not needed. Radioactive assays also have the advantage that the structure of the nascent protein is not altered or can be restored, and thus, proteins can be isolated in a functional form for subsequent biochemical and biophysical studies.

Radioactive methods suffer from many drawbacks related to the utilization of radioactively labeled amino acids. Handling radioactive compounds in the laboratory always involves a health risk and requires special laboratory safety procedures, facilities and detailed record keeping as well as special training of laboratory personnel. Disposal of radioactive waste is also of increasing concern both because of the potential risk to the public and the lack of radioactive waste disposal sites. In addition, the use of radioactive labeling is time consuming, in some cases requiring as much as several days for detection of the radioactive label. The long time needed for such experiments is a key consideration and can seriously impede research productivity. While faster methods of radioactive detection are available, they are expensive and often require complex image enhancement devices.

The use of radioactive labeled amino acids also does not allow for a simple and rapid means to monitor the production of nascent proteins inside a cell-free extract without prior separation of nascent from pre-existing proteins. However, a separation step does not allow for the optimization of cell-free activity. Variables including the concentration of ions and metabolites and the temperature and the time of protein synthesis cannot be adjusted.

Radioactive labeling methods also do not provide a means of isolating nascent proteins in a form which can be further utilized. The presence of radioactivity compromises this utility for further biochemical or biophysical procedures in the laboratory and in animals. This is clear in the case of in vitro expression when proteins cannot be readily produced in vivo because the protein has properties which are toxic to the cell. A simple and convenient method for the detection and isolation of nascent proteins in a functional form could be important in the biomedical field if such proteins possessed diagnostic or therapeutic properties. Recent research has met with some success, but these methods have had numerous drawbacks.

Radioactive labeling methods also do not provide a simple and rapid means of detecting changes in the sequence of a nascent protein which can indicate the presence of potential disease causing mutations in the DNA which code for these proteins or fragments of these proteins. Current methods of analysis at the protein level rely on the use of gel electrophoresis and radioactive detection which are slow and not amenable to high throughput analysis and automation. Such mutations can also be detected by performing DNA sequence analysis on the gene coding for a particular protein or protein fragment. However, this requires large regions of DNA to be sequenced, which is time-consuming and expensive. The development of a general method which allows mutations to be detected at the nascent protein level is potentially very important for the biomedical field.

Radioactive labeling methods also do not provide a simple and rapid means of studying the interaction of nascent proteins with other molecules including compounds which might be have importance as potential drugs. If such an approach were available, it could be extremely useful for screening large numbers of compounds against the nascent proteins coded for by specific genes, even in cases where the genes or protein has not yet been characterized. In current technology, which is based on affinity electrophoresis for screening of potential drug candidates, both in natural samples and synthetic libraries, proteins must first be labeled uniformly with a specific marker which often requires specialized techniques including isolation of the protein and the design of special ligand markers or protein engineering.

Special tRNAs, such as tRNAs which have suppressor properties, suppressor tRNAs, have been used in the process of site-directed non-native amino acid replacement (SNAAR) (C. Noren et al., *Science* 244: 182-188, 1989). In SNAAR, a unique codon is required on the mRNA and the suppressor tRNA, acting to target a non-native amino acid to a unique site during the protein synthesis (PCT WO 90/05785). However, the suppressor tRNA must not be recognizable by the aminoacyl tRNA synthetases present in the protein translation system (Bain et al., *Biochemistry* 30: 5411-21, 1991). Furthermore, site-specific incorporation of non-native amino acids is not suitable in general for detection of nascent proteins in a cellular or cell-free protein synthesis system due to the necessity of incorporating non-sense codons into the coding regions of the template DNA or the mRNA.

Products of protein synthesis may also be detected by using antibody based assays. This method is of limited use because it requires that the protein be folded into a native form and also for antibodies to have been previously produced against the nascent protein or a known protein which is fused to the unknown nascent protein. Such procedures are time consuming and again require identification and characterization of the protein. In addition, the production of antibodies and amino acid sequencing both require a high level of protein purity.

In certain cases, a non-native amino acid can be formed after the tRNA molecule is aminoacylated using chemical reactions which specifically modify the native amino acid and do not significantly alter the functional activity of the aminoacylated tRNA (Promega Technical Bulletin No. 182; tRNA$^{nscend}$™: "Non-radioactive Translation Detection System," September 1993). These reactions are referred to as post-aminoacylation modifications. For example, the ε-amino group of the lysine linked to its cognate tRNA (tRNA$^{LYS}$), could be modified with an amine specific photoaffinity label (U. C. Krieg et al., *Proc. Natl. Acad. Sci. USA* 83: 8604-08, 1986). These types of post-aminoacylation modifications, although useful, do not provide a general means of incorporating non-native amino acids into the nascent proteins. The disadvantage is that only those non-native amino acids that are derivatives of normal amino acids can be incorporated and only a few amino acid residues have side chains amenable to chemical modification. More often, post-aminoacylation modifications can result in the tRNA being altered and produce a non-specific modification of the α-amino group of the amino acid (e.g. in addition to the ε-amino group) linked to the tRNA. This factor can lower the efficiency of incorporation of the non-native amino acid linked to the tRNA. Non-specific, post-aminoacylation modifications of tRNA structure could also compromise its participation in protein synthesis. Incomplete chain formation could also occur when the α-amino group of the amino acid is modified.

In certain other cases, a nascent protein can be detected because of its special and unique properties such as specific enzymatic activity, absorption or fluorescence. This approach is of limited use since most proteins do not have special properties with which they can be easily detected. In many cases, however, the expressed protein may not have been previously characterized or even identified, and thus, its characteristic properties are unknown.

What is needed is a non-radioactive method involving the misaminoacylation of tRNA that allows the incorporation of both native and non-native amino acids into nascent proteins, and that permits a wide variety of markers or labels to be incorporated so that said proteins may be detected.

SUMMARY OF THE INVENTION

The present invention overcomes the problems and disadvantages associated with current strategies for the labeling of proteins involving the use of misaminoacylated tRNA molecules. The present invention provides methods for the chemical misaminoacylation of tRNA molecules by the use of protective groups, and methods for the labeling, detection, quantitation, analysis, and isolation of such labeled proteins.

For example, in one embodiment, the present invention contemplates a method, comprising: a) providing: i) an amino acid (whether naturally occurring or synthetic) comprising an alpha amino group; ii) at least one protective group; and iii) an unprotected polynucleotide comprising x nucleotides, wherein x is an integer between 1 and 10 (preferably between 2 and 10); b) attaching said protective group to said alpha amino group of said amino acid to form a protected amino acid; c) converting said protected amino acid so as to form a protected amino acid ester; and d) reacting said protected amino acid ester with said unprotected polynucleotide under conditions such that an aminoacyl-polynucleotide conjugate comprising said protective group is formed.

At this point, one can take one of two approaches to labeling (e.g. two approaches to introducing a marker, such as a detectable marker, that will eventually be incorporated into the nascent protein). In one embodiment, the next step is to ligate the aminoacyl-polynucleotide conjugate to tRNA. For example, in one embodiment, the present invention contemplates, e) ligating said conjugate of step d) with a tRNA molecule lacking y nucleotides at the 3' terminus, wherein y is an integer between 0 and 10, so as to form a tRNA conjugate comprising a protective group. Thereafter, the present invention contemplates (for this embodiment) the steps: f) removing said protective group of said tRNA conjugate so as to form an unprotected tRNA conjugate; and g) attaching a marker moiety to said unprotected tRNA conjugate so as to form a marker-tRNA conjugate.

As noted, however, this is but one approach. Another approach is to delay ligation and label the aminoacyl-polynucleotide conjugate of step (d) above. For example, in one embodiment, the present invention contemplates the steps: e) removing said protective group of said aminoacyl-polynucleotide conjugate of step (d) so as to form an unprotected aminoacyl-polynucleotide conjugate; and f) attaching a marker moiety to said unprotected aminoacyl-polynucleotide conjugate so as to form a marker-aminoacyl-polynucleotide conjugate. For this embodiment, the ligation step comes after introduction of the marker. For example, the present invention contemplates the step: g) ligating said marker-aminoacyl-polynucleotide conjugate of step f) with a tRNA molecule lacking y nucleotides at the 3' terminus, wherein y is an integer between 0 and 10, so as to form a marker-tRNA conjugate.

In another embodiment, the present invention contemplates a method comprising: a) providing an amino acid, at least one protective group, a marker moiety, an unprotected dinucleotide, and a tRNA molecule lacking two nucleotides at the 3' terminus; b) introducing said protective group onto the alpha amino group of said amino acid to form a protected amino acid (under conditions such that said protective group may be replaced with a marker at the aminoacyl-dinucleotide or aminoacyl-tRNA stage); c) linking the protected amino acid to the 2'(3') OH group of the unprotected dinucleotide under conditions such that a aminoacyl-dinucleotide conjugate is formed; d) removing the protective group of said protected amino acid; e) introducing said marker moiety so as to form a marker-aminoacyl-dinucleotide conjugate; and f) linking the 5'-phosphate of said marker-aminoacyl-dinucleotide conjugate to the 3'-OH group of said tRNA molecule.

It is not intended that the present invention be limited to any specific polynucleotide. In one embodiment, said polynucleotide is a dinucleotide. For example, the dinucleotide 5'-phospho-deoxycytidyl-adnosine is particularly useful. In another embodiment, the present invention contemplates a method that provides a polynucleotide comprising between 3-10 nucleotides (e.g. trinucleotide, quadranucleotide, pentanucleotide, etc.). In one embodiment said polynucleotide is a ribonucleotide. In another embodiment, said polynucleotide is a deoxyribonucleotide. In yet another embodiment, said polynucleotide is a dideoxyribonucleotide.

In another embodiment, the present invention contemplates the above methods wherein said amino acid is a natural amino acid. In another embodiment, said amino acid is an un-natural amino acid (i.e. it does not occur in nature).

It is not intended that the present invention be limited to a method utilizing a specific number of protective groups. In one embodiment, the method of the present invention utilizes one protective group. In another embodiment, at least two protective groups are provided. In a further embodiment, a method utilizing more than two protective groups is contemplated.

It is not intended that the present invention be limited to any specific protective group. In one embodiment, said protective group is selected from the group consisting of 1-(2-nitrophenyl-5-methyl)ethyloxycarbonyl (Npe), 1-(2-nitrophenyl-4,5-dimethoxy)ethyloxycarbonyl (NVOC), 1-(2-nitrophenyl)ethyloxycarbonyl, 3,5-(dimethoxy)benzyloxycarbonyl, 2-nitrophenylsulfenyloxycarbonyl, biphenylylisopropyloxycarbonyl (Bpoc), 9-fluorenylmethyloxycarbonyl (Fmoc), and pent-4-enoyl (Pent). In embodiments utilizing more than one protective group, the protective groups may be the same or different.

It is not intended that the present invention be limited to a protective group having any specific chemical or physical properties. In one embodiment, the present invention contemplates a protective group that is photolabile. In another embodiment, said protective group is acid or base labile. In another embodiment, said protective group can be selectively removed (for example, if there are two protective groups, conditions can be used wherein only one of the protective groups is removed and the other remains).

It is not intended that the present invention be limited to any particular marker moiety. In one embodiment, said marker moiety is selected from biotin, photocleavable biotin, BODIPY-FL, BODIPY 558/568, fluorescein, NBD-X, phenyldiboronic acid (PDBA)-X, and cyanine 3 (Cy3). In another embodiment, said marker moiety is photocleavable. In another embodiment, said marker moiety is a chelator. In another embodiment, said marker moiety is a photocleavable marker that is a chelator capable of forming luminescent complexes. In a preferred embodiment, said marker moiety is capable of forming a complex with its binding partner, wherein said complex may be, for example, fluorescent or luminescent. In another preferred embodiment, said marker moiety is a linker.

Although the present invention is not limited to any particular site on the resultant protein at which said marker moiety is incorporated, in a preferred embodiment, said marker moiety is incorporated at the N-terminus of the protein.

It is not intended that the present invention be limited to a tRNA molecule lacking any particular number of nucleotides at its 3' terminus. In one embodiment, the present invention contemplates a tRNA molecule lacking between 0-10 nucleotides at its 3' terminus, more preferably between 2-8, even more preferably between 2-6. In a preferred embodiment, the present invention contemplates a tRNA molecule lacking two nucleotides at its 3' terminus. In another embodiment, said tRNA molecule is lacking three nucleotides at its 3' terminus.

It is not intended that the present invention be limited to any specific type of a tRNA molecule lacking preferably between 0-10 nucleotides at the 3' terminus. In one embodiment, the present invention contemplates a tRNA molecule that is an initiator tRNA. In another embodiment, said tRNA is an elongator tRNA. In another embodiment, said tRNA is a suppressor tRNA. Moreover, the present invention also contemplates methods wherein a plurality of tRNAs is used.

The present invention also contemplates composition useful in labeling nascent proteins, such as the family of compounds of the formula:

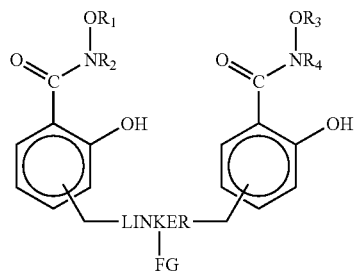

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, and LINKER is a chain comprising at least three carbon atoms. It is not intended that the present invention be limited by the nature of the LINKER. In one embodiment, the LINKER is an amino-substituted dicarboxylic acid; such acids are commercially available, e.g. (Fmoc)Glu(OtBu)ONHS and (Fmoc)Asp(OtBu)ONHS. It is also not intended that the present invention be limited by the nature of the functional group. Any chemical group that can function as a site of attack for binding to other reagents or is reactive with other groups is contemplated. In one embodiment, the functional group is selected from a sulfhydryl group, a carboxyl group and a hydroxyl group. In a preferred embodiment, said functional group is an amino group. In another embodiment, the functional group is a 1,2-diol. In yet another embodiment, the functional group is a crosslinker, such as the bifunctional crosslinkers shown in Tables 2-4.

The above-general formula defines a broad group of contemplated compounds that are useful for further attachment reactions (via the functional group). For example, in one embodiment, the present invention contemplates a composition having the formula:

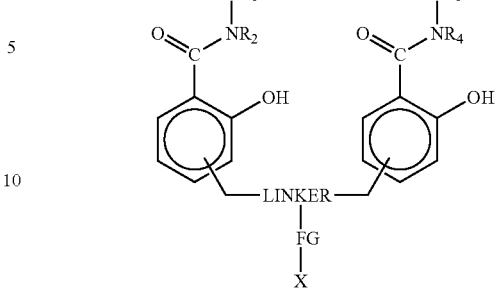

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, LINKER is a chain comprising at least three carbon atoms, and X is selected from the group consisting of a solid support (beads, plates, surfaces etc.), a detectable marker (e.g. a fluorescent marker such as a fluorescent dye), and a biomolecule (e.g. proteins, peptides, nucleic acids, carbohydrates, lipids, etc.). Again, it is not intended that the present invention be limited by the nature of the functional group. In one embodiment, said functional group is an amino group. In another embodiment, the functional group is a carboxyl, sulfhydryl, 1,2-diol or hydroxyl. Again, it is not intended that the present invention be limited by the nature of the LINKER. In one embodiment, the LINKER is an amino-substituted dicarboxylic acid; such acids are commercially available, e.g. (Fmoc)Glu(OtBu)ONHS and (Fmoc)Asp(OtBu)ONHS.

The present invention contemplates specific subsets of the broad family of compounds outlined above. In one embodiment, the present invention contemplates a composition having the formula:

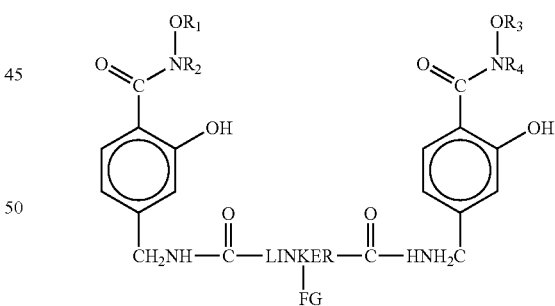

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, and LINKER is a chain comprising at least one carbon atom. Again, the functional group can be a variety of groups, including but not limited to an amino group.

Again, these specific subsets of compounds are useful for further attachment reactions (via the functional group). In one embodiment, the present invention contemplates a composition having the formula:

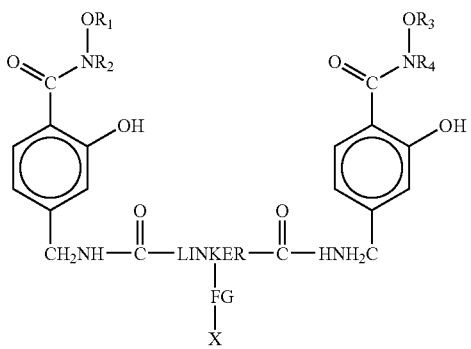

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group (such as an amino group), LINKER is a chain comprising at least one carbon atom, and X is selected from the group consisting of a solid support, a detectable marker, and a biomolecule.

Still additional subsets are contemplated. In one embodiment, the present invention contemplates a composition having the formula:

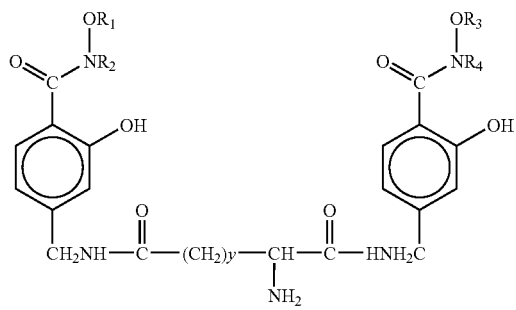

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, and y is an integer between 0 and 6.

This subset is also useful for further attachment reactions. For example, the present invention contemplates a composition having the formula:

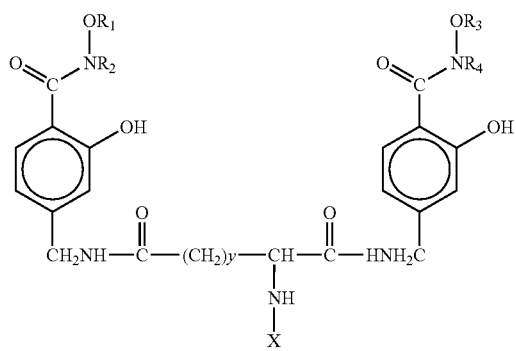

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, y is an integer between 0 and 6, and X is selected from the group consisting of a solid support, a detectable marker, and a protein.

The present invention also contemplates methods of synthesis of the above-described family of compounds. In one embodiment, the present invention contemplates a method, comprising: a) providing 4-aminomethyl-salicylic acid methyl ester monomers and a linker moiety; and b) reacting said 4-aminomethyl-salicylic acid methyl ester monomers and said linker moiety under conditions such that a compound is formed of the general formula:

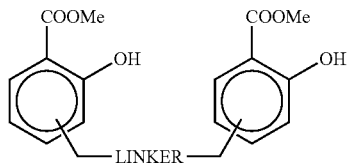

wherein LINKER is a chain comprising at least three carbon atoms. It is contemplated that this dimer is reactive with phenyldiboronic acid (and various derivatives thereof).

The present invention contemplates certain embodiments which conveniently permit the synthesis of members of the family of compounds outlined above. In one embodiment, the present invention contemplates method, comprising: a) providing first and second 4-aminomethyl-salicylic acid methyl ester monomers and a linker moiety, said linker moiety having the general structure:

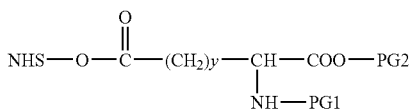

wherein PG1 is a first protective group, PG2 is a second protective group, and y is an integer between 0 and 6; and b) reacting said first 4-aminomethyl-salicylic acid methyl ester monomer with said linker moiety under conditions such that a first intermediate compound is formed of the general formula:

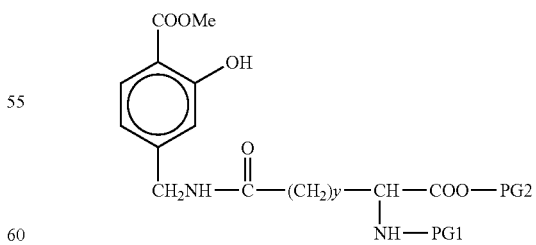

c) removing said second protective group of said first intermediate compound so as to create a second intermediate compound; and d) reacting said second intermediate compound with said second 4-aminomethyl-salicylic acid methyl ester monomer so as to create a dimer of the general formula:

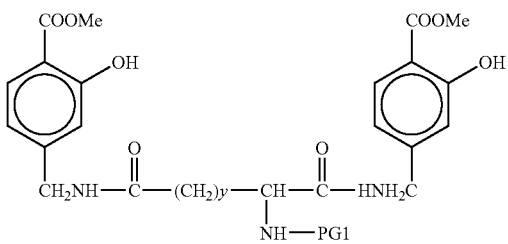

The present invention contemplates (in one embodiment) the further step of e) treating said dimer of step (d) so as to convert it to a compound of the general formula:

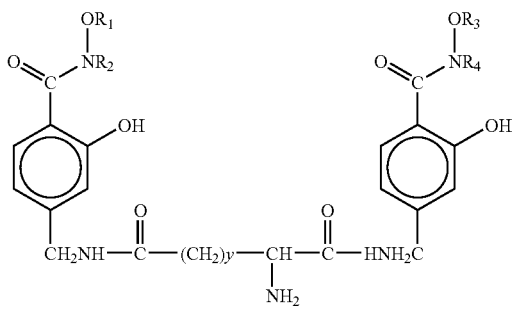

This converted compound (which will also bind phenyldiboronic acid) can be used for further attachment reactions (via the amino group of the linker chain). In one embodiment, the present invention contemplates the further step of f) reacting said compound of step (e) with derivatized marker, said derivatized marker comprising an amine-reactive moiety, so as to create a marker-dimer conjugate. In one embodiment, said derivatized marker is a derivatized fluorescent marker.

The present invention also contemplates a method comprising reacting salicylic acid methyl ester moieties linked by a linker containing protected functional group under conditions that result in conversion of methyl ester moiety to the corresponding amides. In preferred embodiments, the amides are derived from hydroxylamine (the reaction results in formation of salicylhydroxamic acids) or from substituted (alkyl) hydroxylamine derivatives (the reaction results in formation of substituted salicylhydroxamic acids). In one embodiment, the conditions used for conversion of methyl ester groups into the hydroxamic moieties result also in simultaneous removal of protective group from the functional group. In another embodiment, the removal of protective group from the functional group is a separate step that occurs under different conditions after the formation of the salicylhydroxamic acid.

The methods of the present invention in one embodiment, comprises tRNA$^{TOTAL}$ (total tRNA). In another embodiment, the present invention contemplates that the tRNA total tRNA and that the total tRNA comprises a plurality of different (a mixture of tRNAs corresponding to a plurality of different amino acids including an initiator tRNA) tRNAs.

DEFINITIONS

As used herein, the term "protected amino acid" refers to an amino acid that is bound to a "protective group," whereas an "unprotected amino acid" is not so bound. As used herein, the term "protective group" refers to a chemical group (e.g. NVOC, Fmoc and Bpoc) which is bound to a monomer unit and which may be removed (e.g. selectively removed) therefrom to expose an reactive or active site such as, in the specific example of a nucleotide or photocleavable linker, an amino group. A protective group is capable of being "selectively removed" where its removal does not disrupt the integrity of the molecule to which it is attached, or where more than one different protective group is present, it may be removed while the other protective group is left intact, or both.

As used herein, the term "p(d)CpA dinucleotide" or "pdCpA dinucleotide" refers to a molecule comprising an adenosine linked to a cytosine via a phosphate group.

As used herein, the term "polynucleotide" refers to a molecule comprising more than one (e.g. two, three, etc.) nucleotide moiety such as, for example, a di- or tri-nucleotide. Polynucleotides may be ribonucleotides, deoxynucleotides, and dideoxynucleotides. The present invention specifically contemplates the preparation of aminoacylated tRNA using a polynucleotide comprising adenosine and cytosine (e.g. pdCpA).

As used herein, the term "marker" and "marker moiety" refers to any atom or molecule which can be used to provide a detectable (preferably quantifiable) signal, and which can be attached to a amino acids, peptides, nucleotides, polynucleotides, or nucleic acids (including polynucleic acids). Markers may provide signals detectable by fluorescence, radioactivity, colorimetry, gravimetry, X-ray diffraction or absorption, magnetism, enzymatic activity, and the like. Such markers can be added to the nucleic acids, aminoacids, nucleotides and polynucleotides of the present invention. Marker molecules are "capable of being independently detected" where, in a mixture comprising two or more different markers, each marker has a separate and distinct detectable (preferably quantifiable) signal. A marker is considered "bifunctional" where it may be utilized both as a detectable moiety and an affinity moiety (i.e. allows selective binding or attachment to another chemical group or moiety, or a nucleic acid or peptide).

Various methods of adding markers to nucleotides, polynucleotides, or nucleic acids are known in the art and may be used. Examples of markers for nucleotides, polynucleotides, or nucleic acids include, but are not limited to, the following: radioisotopes (e.g. $^3$H), fluorescent markers (e.g. BODIPY, fluorescein [FAM-5, FAM-6, EX-5], PDBA, NBD-X, and Cy3), enzymatic markers (e.g. horseradish peroxidase, beta-galactosidase, luciferase, alkaline phosphatase), biotinyl groups, pre-determined polypeptide epitopes recognized by a secondary reporter (e.g. leucine zipper pair sequences, binding sites for secondary antibodies, metal binding domains, and epitope tags). In some embodiments, markers are attached by linkers, or spacer arms, of various lengths to reduce potential steric hindrance.

As used herein, the term "photocleavable marker" refers to a marker that may be removed from a nucleotide, polynucleotide, chemical group, or nucleic acid, to which it is attached or operably linked, by exposure to electromagnetic radiation (e.g. visible light, UV light, etc.). The wavelength of light necessary to photocleave the marker is dependent upon the structure of the photocleavable marker used.

As used herein, the term "chelator" refers to a ligand that contains two or more atoms, each of which can simultaneously form a two-electron donor bond (i.e. chelate) to the same metal ion. A "chelator" may also be referred to as a polydentate ligand.

As used herein, the phrase "the photocleavable marker is a chelator capable of forming luminescent complexes," refers to a photocleavable marker molecule comprising a portion that chelates a metal ion (e.g. Terbium, Europium, Samarium, Ruthenium, Calcium, Magnesium, Manganese, Iron, Copper, Cobalt, Nickel, or other polyvalent cations) wherein the chelating of said metal ion allows detection by luminescence. For example, the present invention contemplates a photocleavable marker that is a first chelator (e.g. salicylic acid) capable of forming luminescent complex when reacted with a second chelator (e.g. EDTA) and a metal ion (e.g. $Tb^{3+}$).

As used herein, the term "binding member" refers to a portion of a marker molecule that is operably linked to a nucleotide molecule wherein said marker molecule further binds to another portion of a marker molecule so as to allow detection. For example, the present invention contemplates the detection of a photocleavable marker comprising a first binding member (e.g. biotin) that is detected by binding with a second binding member (e.g. streptavidin). In another example, the present invention contemplates the detection of a photocleavable marker comprising a first binding member (e.g. phenyldiboronic acid) that is detected by binding with a second binding member (e.g. salicylhydroxamic acid).

As used herein, the term "tRNA" refers to transfer ribonucleic acid. An "initiator tRNA" is a tRNA molecule that is acylated with an amino such as, for example, methionine (i.e. forming $tRNA^{Met}$) or N-formylmethionine (i.e. forming $tRNA^{fMet}$), and lack hydrogen bonding of the 5'-terminal base. A "suppressor tRNA" is a tRNA molecule that comprises an anticodon such as, for example CUA or UUA, which allows pairing with a termination codon (e.g. UAG and UAA). An "elongator tRNA" is a tRNA molecule that is neither a "initiator," nor "suppressor," and which places its corresponding amino acid or codon in its proper sequence during the process of translation.

As used herein, the term "total tRNA" is used to describe a mixture comprising misaminoacylated marker tRNA molecules representing each amino acid and may be designated as "$tRNA^{TOTAL}$". This mixture has a distinct advantage over the limited ability of misaminoacylated lys-tRNA to reliably incorporate in large variety of proteins. It is contemplated that "total tRNA" will provide a homogenous insertion of affinity markers in all nascent proteins.

In another embodiment DNA-bis(SHA)-PDBA-Polypeptide conjugates are incubated with bis(SHA) containing surface. In one embodiment a plurality of various PDBA-Polypeptide conjugates are spotted on the bis(SHA) containing surface and immobilized in a site specific manner. The support containing a plurality of various polypeptide is then subjected to a variety of interrogation solutions after which specific reactions and interactions with immobilized polypeptides are detected.

Figure 40:
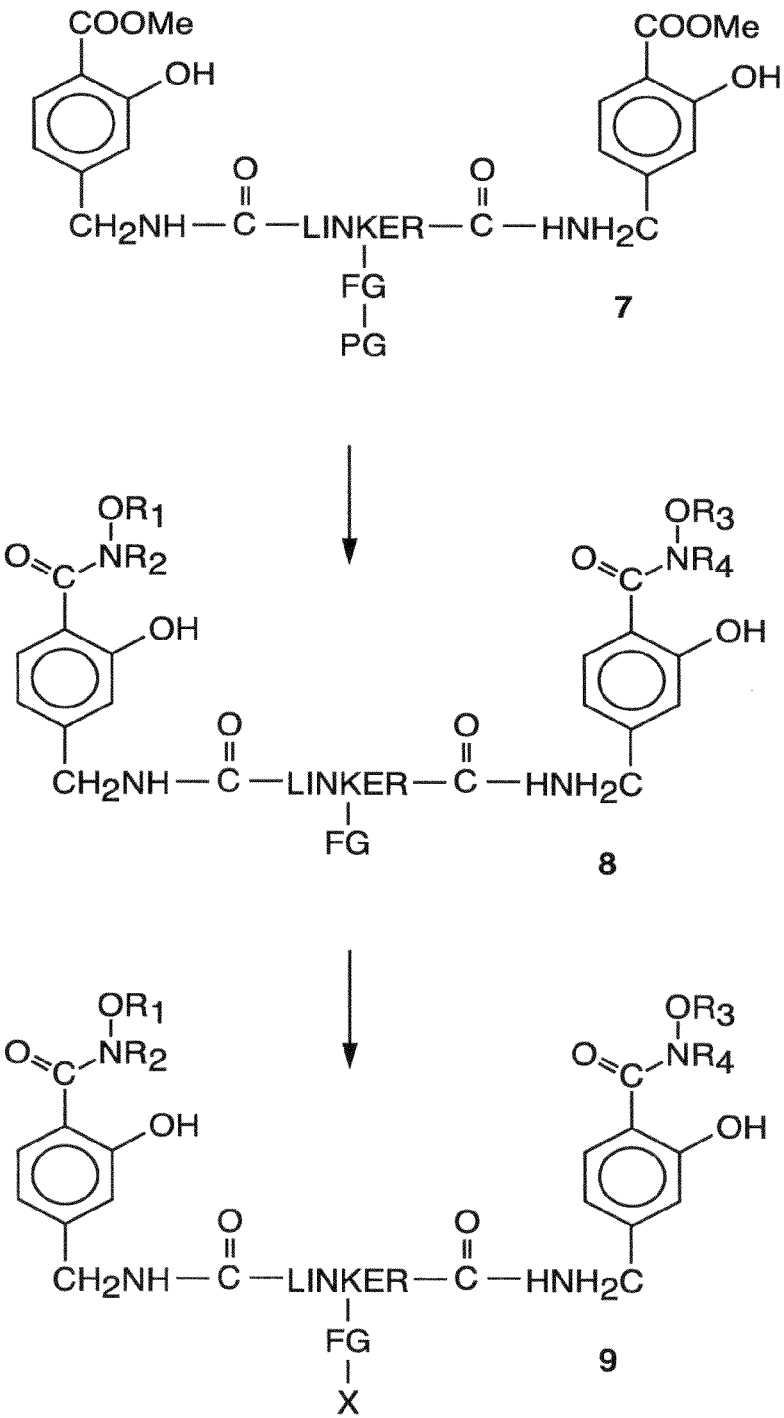

FIG. 40 depicts the general reaction scheme for another embodiment of a method to produce a bis(SHA) conjugate, wherein LINKER is a symmetrical linker moiety flanked by two carbonyl groups, FG is a functional group, PG is a protective group, groups R1-R4 are either hydrogen or an alkyl group, and X is a group or structure selected from a marker moiety, a bifunctional cross-linker, a polypeptide, a nucleic acid, alkaline phosphatase, horseradish peroxidase, and a solid support.

Figure 41:
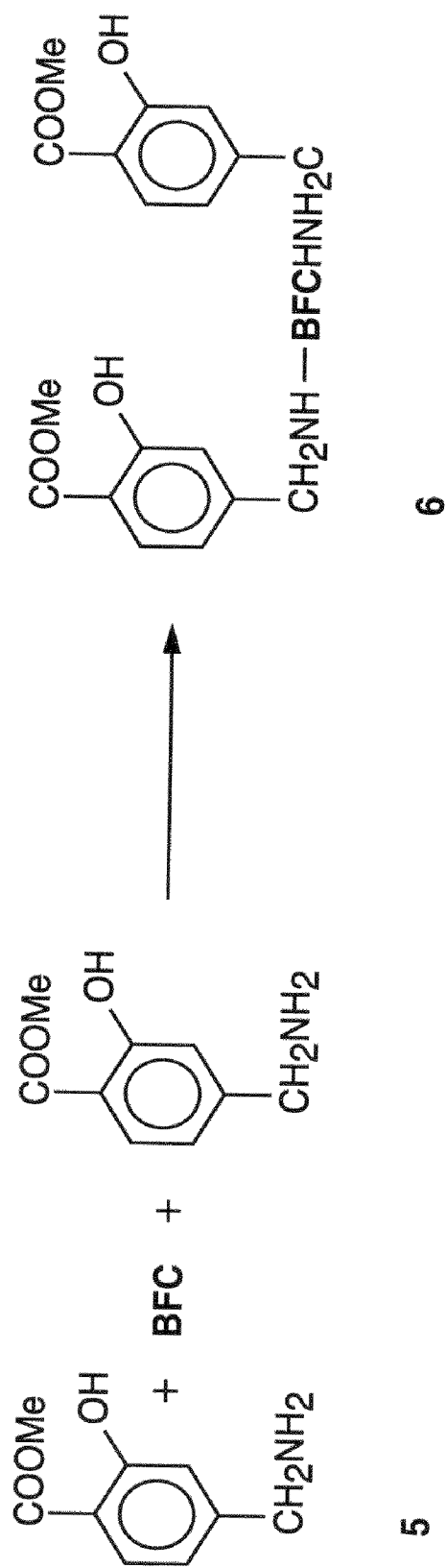

FIG. 41 depicts the reaction scheme for one embodiment of a method to produce a 4-aminomethyl-salicylic acid methyl ester dimer. The group "BFC" represents a bifunctional cross-linker (activated or activatable) such as, for example, the crosslinkers listed in Table 2.

Figure 42:
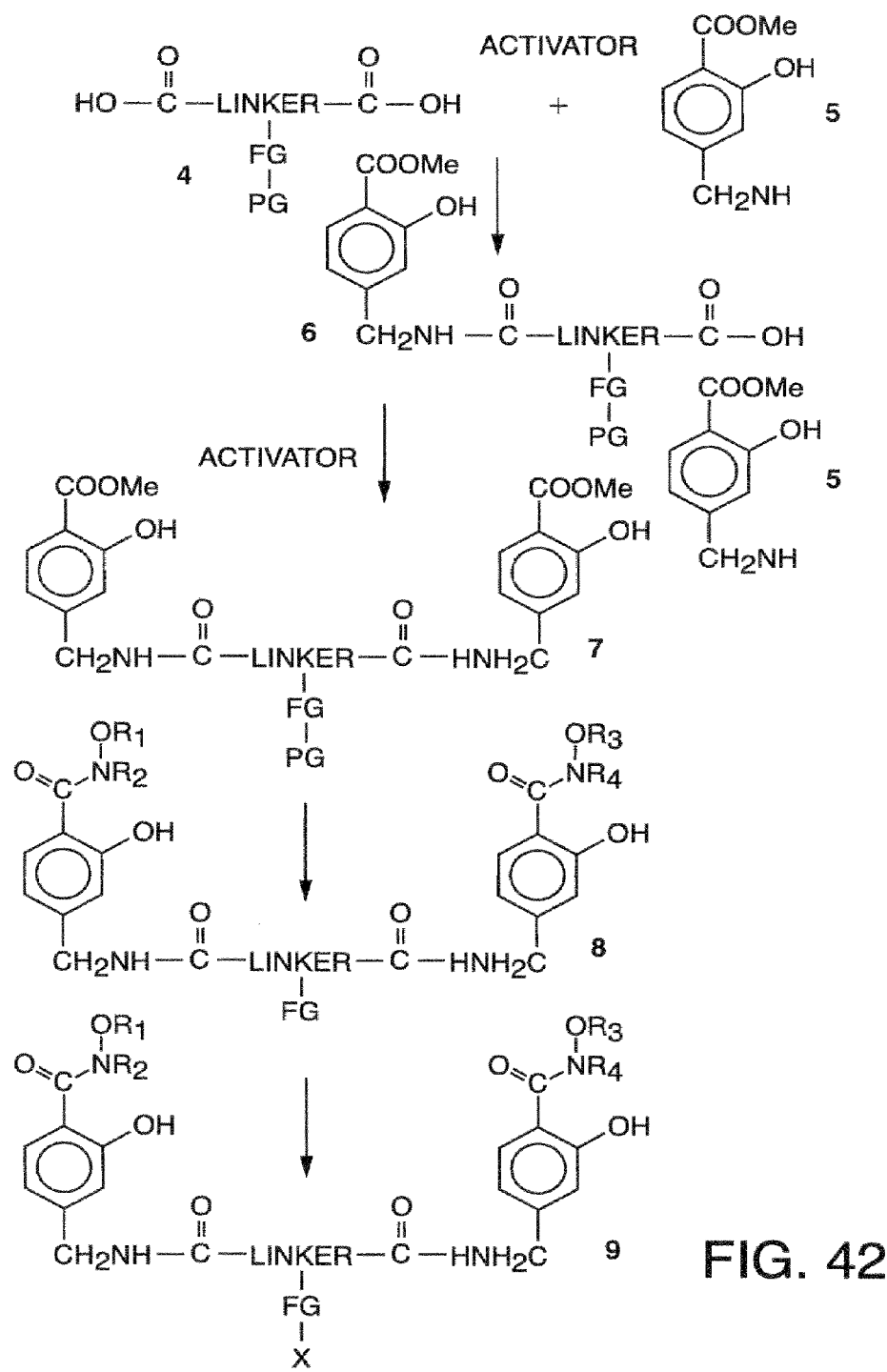

FIG. 42 depicts the same reaction scheme as described in FIG. 40 with the additional step to produce a 4-aminomethyl-salicylic acid methyl ester dimer (compound 7) from an activatable linker and two 4-aminomethyl-salicylic acid methyl ester monomers. Groups R1-R4 are either hydrogen or an alkyl group.

Figure 43:
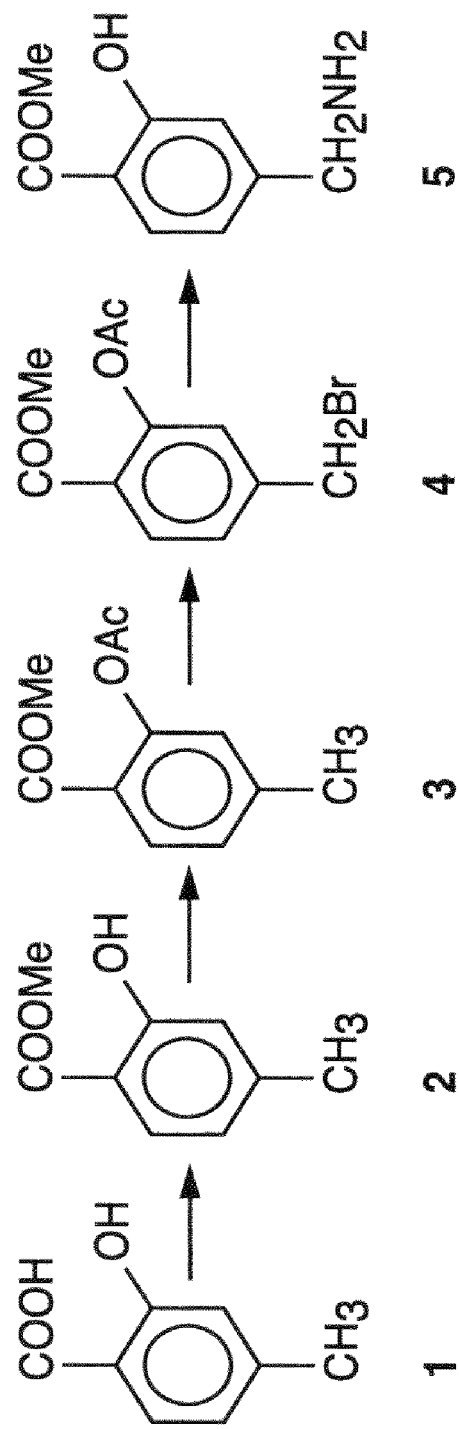

FIG. 43 depicts the reaction scheme for one embodiment of a method to synthesize a 4-aminomethyl-salicylic acid methyl ester monomer.

Figure 44:
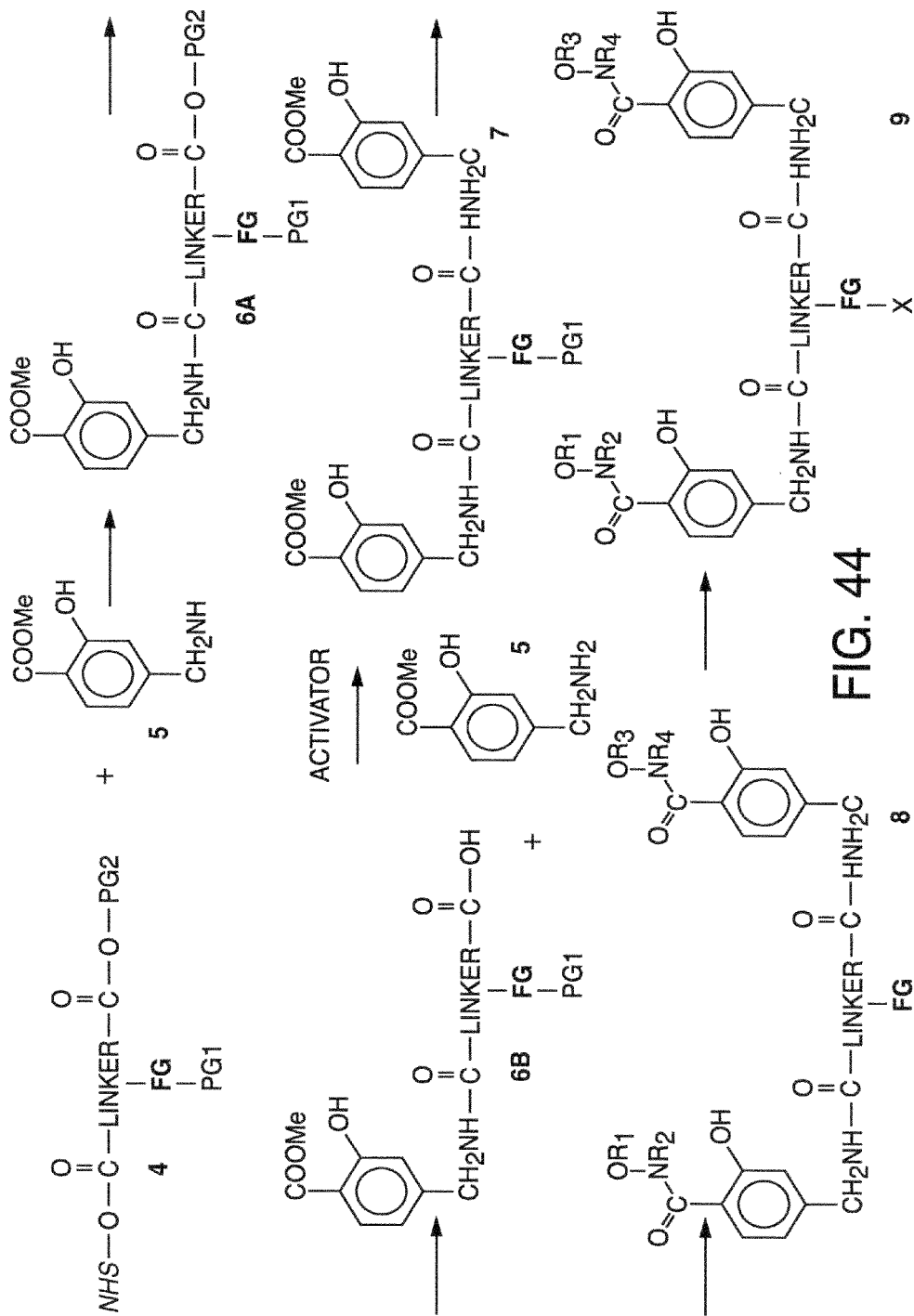

FIG. 44 depicts the reaction scheme for one embodiment of a method to synthesize a bis(SHA) conjugate. The group "LINKER" is a linker moiety (e.g. such as, for example, those compounds listed in Tables 5, 6a & 6b). The group "FG" is a functional group such as carboxyl, sulfhydryl, 1,2-diol, hydroxyl. The group "PG" is a protective group such as 1-(2-nitrophenyl-5-methyl)ethyloxycarbonyl (Npe), 1-(2-nitrophenyl-4,5-dimethoxy)ethyloxycarbonyl (NVOC), 1-(2-nitrophenyl)ethyloxycarbonyl, 3,5-(dimethoxy)benzyloxycarbonyl, 2-nitrophenylsulfenyloxycarbonyl, biphenylylisopropyloxycarbonyl (Bpoc), 9-fluorenylmethyloxycarbonyl (Fmoc), and pent-4-enoyl (Pent). The group "X" is a structure or group such as a marker moiety (e.g. BODIPY-FL), a bifunctional cross-linker, a polypeptide, a nucleic acid, alkaline phosphatase, horseradish peroxidase, and a solid support. Groups R1-R4 are either hydrogen or an alkyl group.

Figure 45:
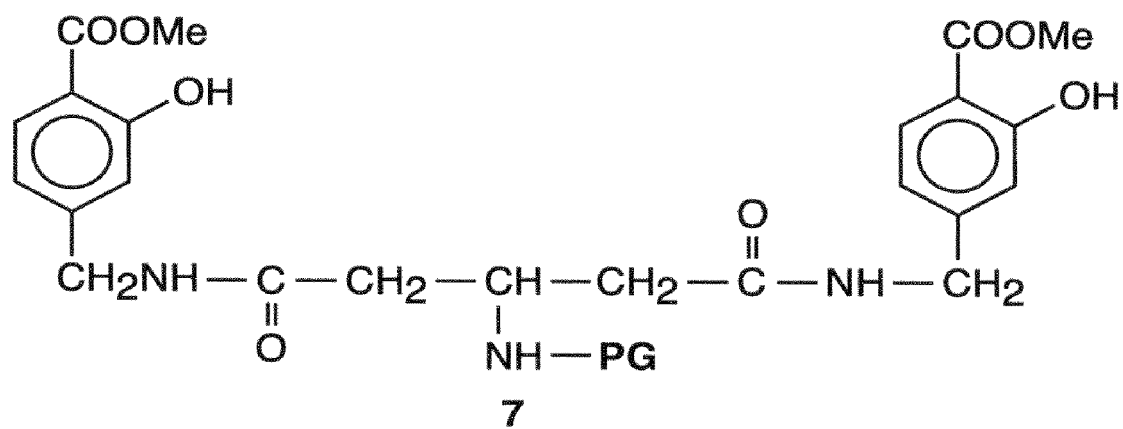

FIG. 45 depicts a contemplated compound wherein an amino group (i.e. the functional group) is in a symmetrical position on the linker moiety. The group "PG" is a protective group.

Figure 46:
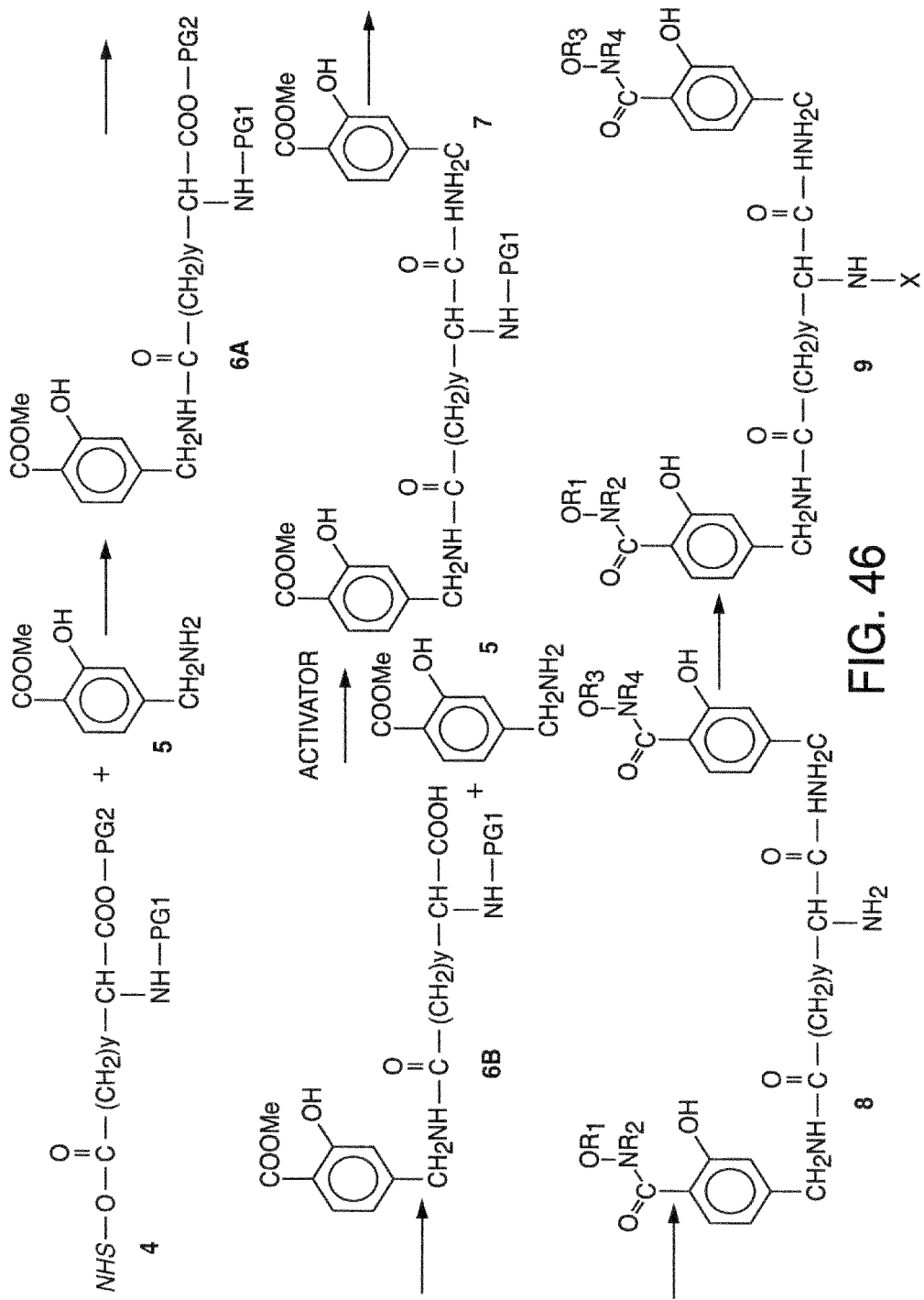

FIG. 46 depicts the reaction scheme for one embodiment of a method to synthesize bis(salicylhydroxamic acid). The group "PG1" is a first protective group. The group "PG2" is a second protective group. Said protective groups may be selected from, for example, 1-(2-nitrophenyl-5-methyl)ethyloxycarbonyl (Npe), 1-(2-nitrophenyl-4,5-dimethoxy)ethyloxycarbonyl (NVOC), 1-(2-nitrophenyl)ethyloxycarbonyl, 3,5-(dimethoxy)benzyloxycarbonyl, 2-nitrophenylsulfenyloxycarbonyl, biphenylylisopropyloxycarbonyl (Bpoc), 9-fluorenylmethyloxycarbonyl (Fmoc), and pent-4-enoyl (Pent). The "$(CH_2)_Y$" group, represents the fact that the linker moiety of compound 6 (and compounds 7 & 8) may comprise any number of —$CH_2$ groups. For example, in one embodiment, "Y" is an integer from 1-20. Groups R1-R4 are either hydrogen or an alkyl group X is a group or structure selected from a marker moiety, a bifunctional cross-linker, a polypeptide, a nucleic acid, alkaline phosphatase, horseradish peroxidase, and a solid support.

Figure 47:
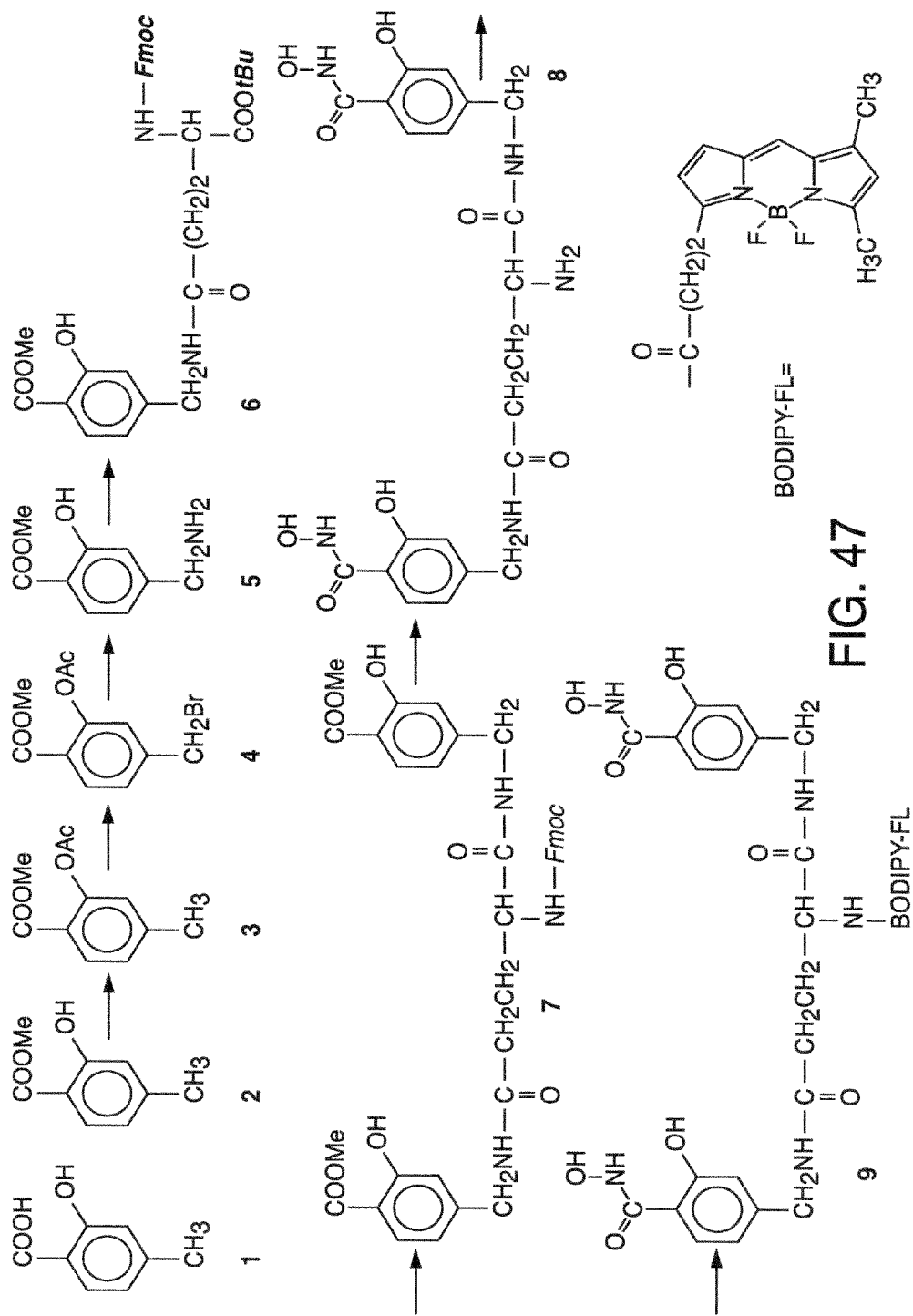

FIG. 47 depicts a reaction scheme for one preferred embodiment of a method to synthesis a bis(SHA) conjugate. The scheme is as is described for FIG. 46, but wherein PG1 is Fmoc, PG2 is tBu, groups R1-R4 are hydrogen molecules, Y is equal to 2, and X is a marker moiety (e.g. BODIPY-FL).

Figure 48:
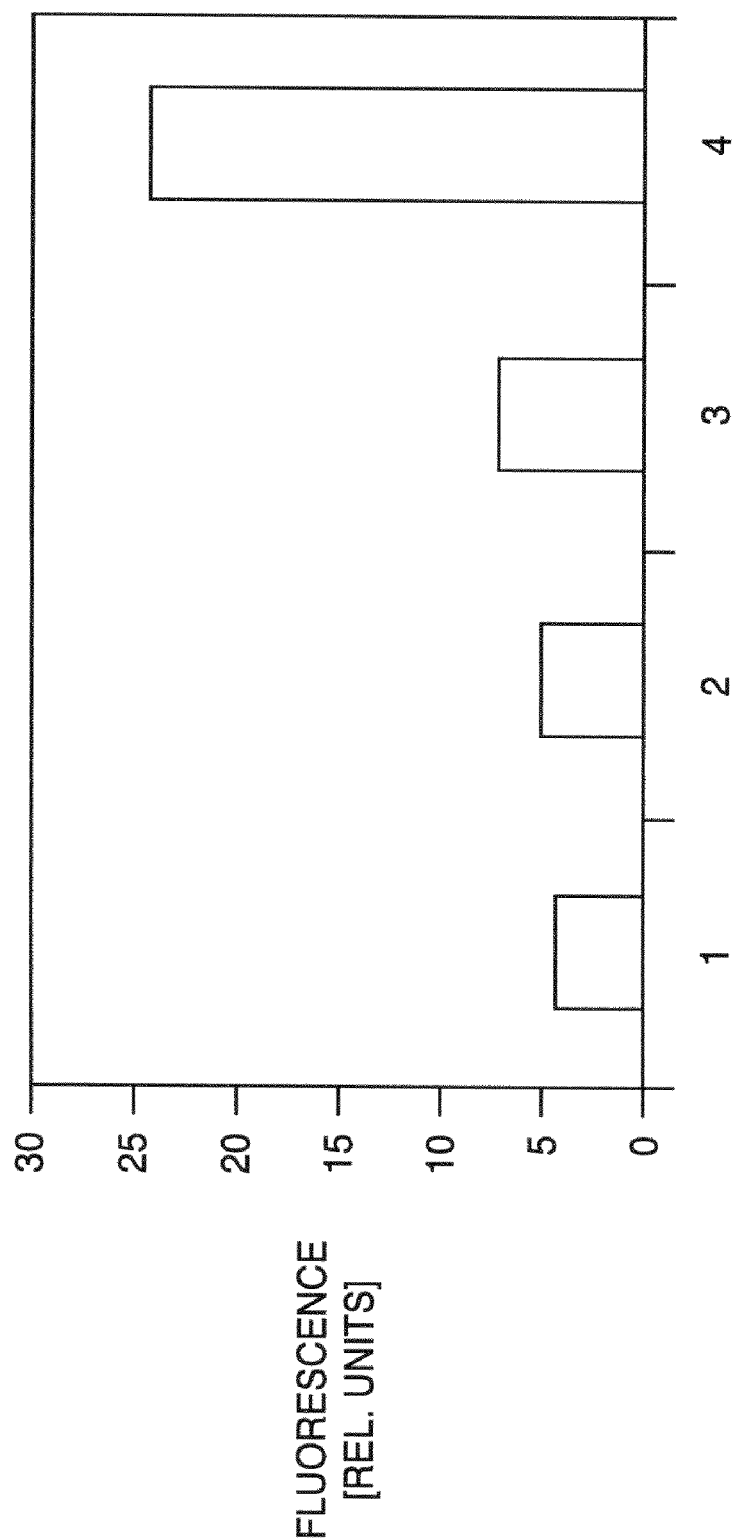

FIG. 48 depicts a graph showing the integrated intensity for each sample of Sepharose 4B beads conjugated with diamine linker (sample 1), and with 1,3-phenyldiboronic acid (PDBA) (sample 2); Beads conjugated with diamine and incubated with BODIPY-FL-bis(SHA) conjugate (sample 3) and beads conjugated with 1,3-phenyldiboronic acid (PDBA) and incubated with BODIPY-FL-bis(SHA) conjugate (sample 4). The image obtained using a transilluminator (365 nm) and a CCD imaging system (ChemImager, AlphaInnotech).

Figure 49:
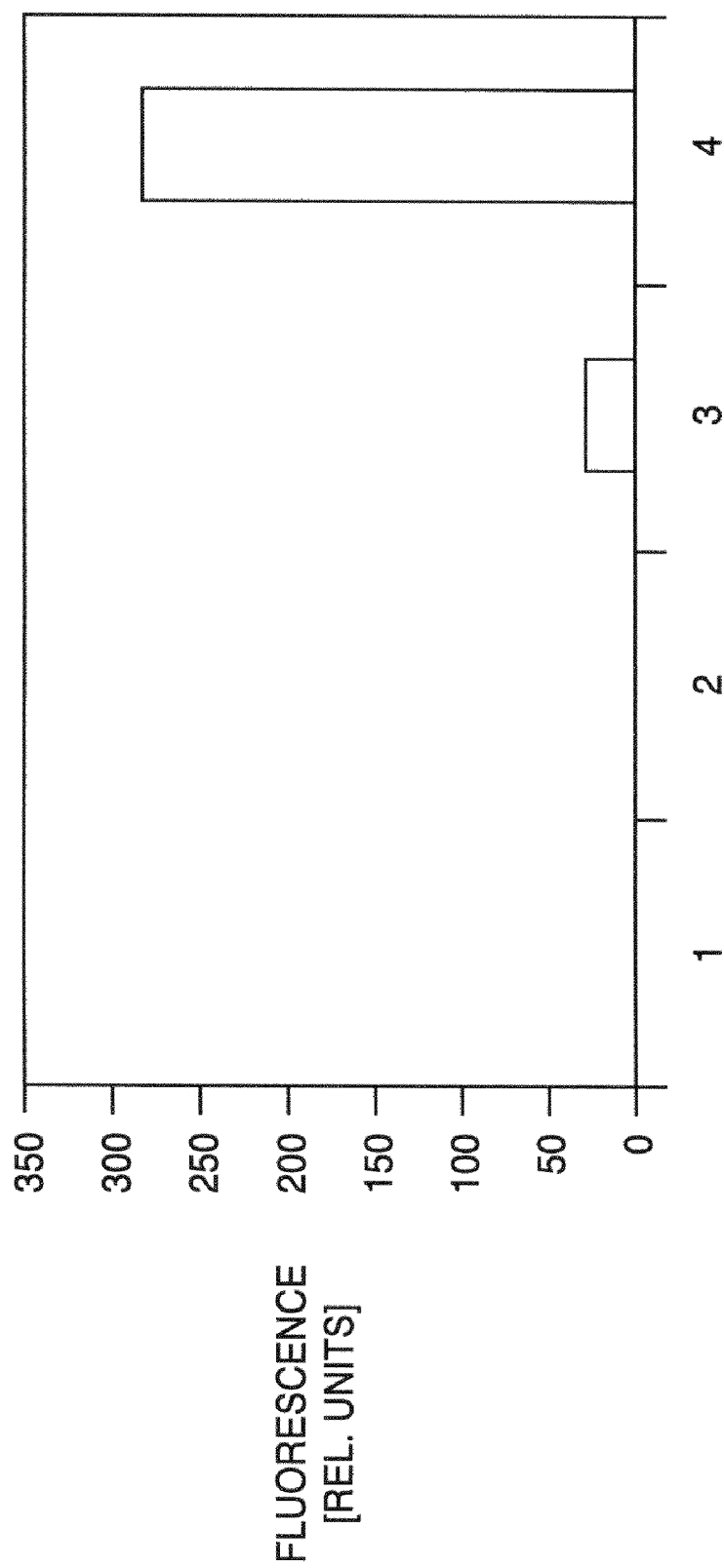

FIG. 49 depicts a graph showing the integrated intensity for each sample of Sepharose 4B beads conjugated with diamine linker (sample 1), and with 1, 3-phenyldiboronic acid (PDBA)(sample 2); Beads conjugated with diamine and incubated with BODIPY-FL-bis(SHA) conjugate (sample 3) and beads conjugated with 1,3-phenyldiboronic acid (PDBA) and incubated with BODIPY-FL-bis(SHA) conjugate (sample 4). The image was obtained using a 488 mm laser scanner (FluorImager, Molecular Dynamics).

Figure 50A:
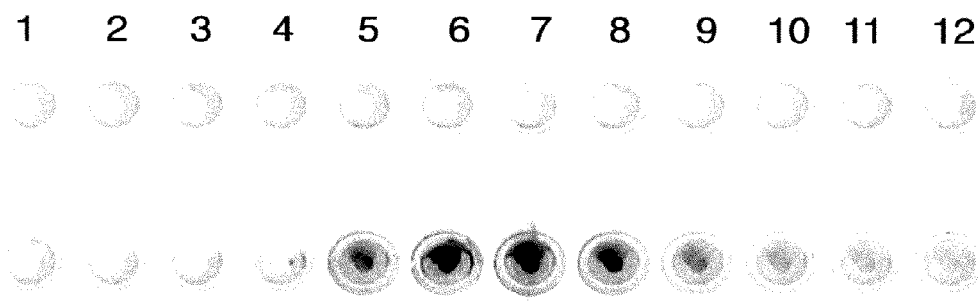
Figure 50B:
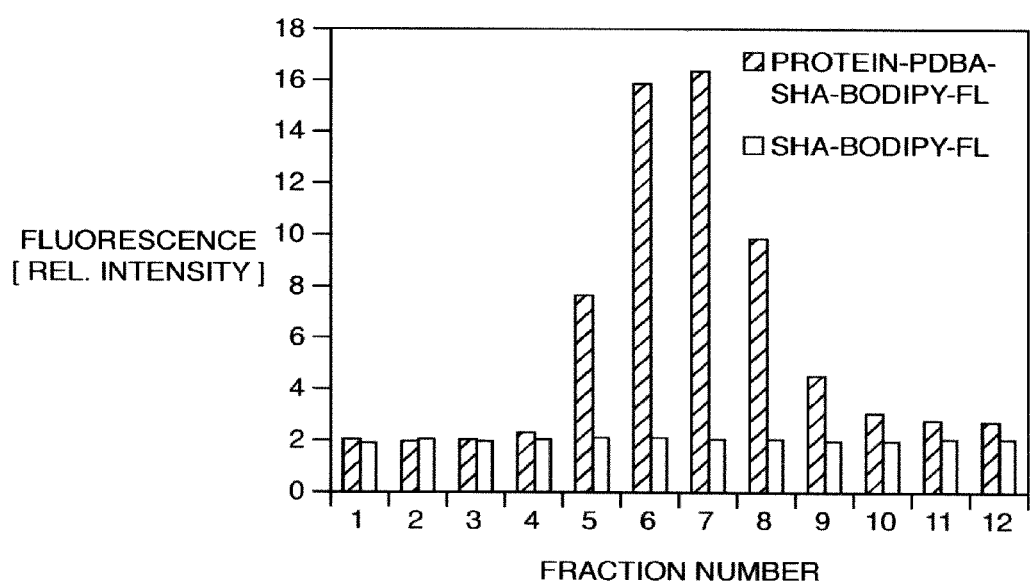

FIG. 50 Gel filtration separation of BODIPY-FL-bis(SHA) alone and int the presence of PDBA modified trypsin inhibitor. Top: provides an image depicting microwells containing fractions eluted of the gel filtration column imaged using FluorImager. Bottom: depicts a graph showing the integrated intensity for each eluate fraction.

Figure 51:
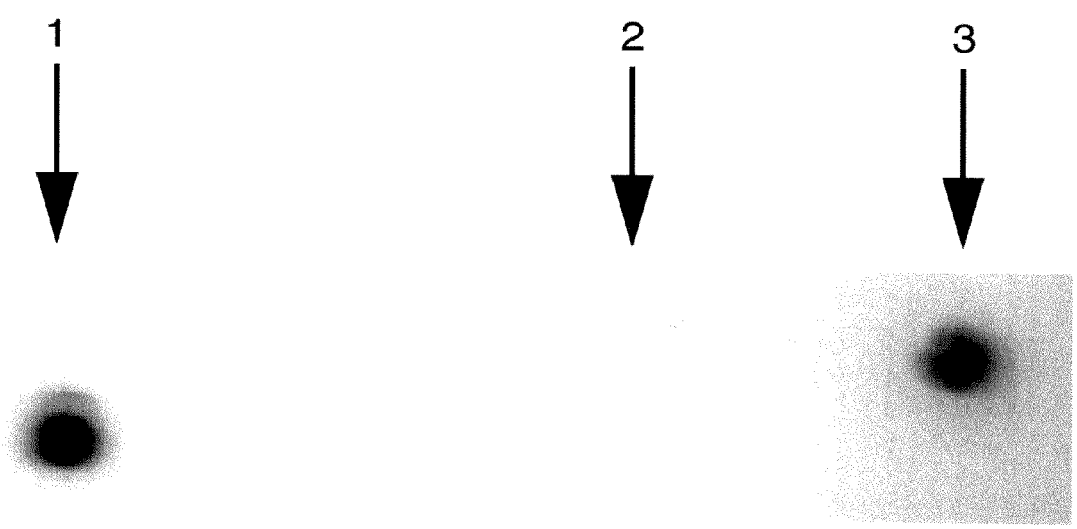

FIG. 51 shows a PVDF membrane with dot-blotted protein samples (1-4): 1-BODIPY-FL modified trypsin inhibitor, 2-trypsin inhibitor, 3-PDBA-modified trypsin inhibitor. The membrane was incubated with a solution of BODIPY-FL-bis (SHA) conjugate after spotting.

Figure 52:
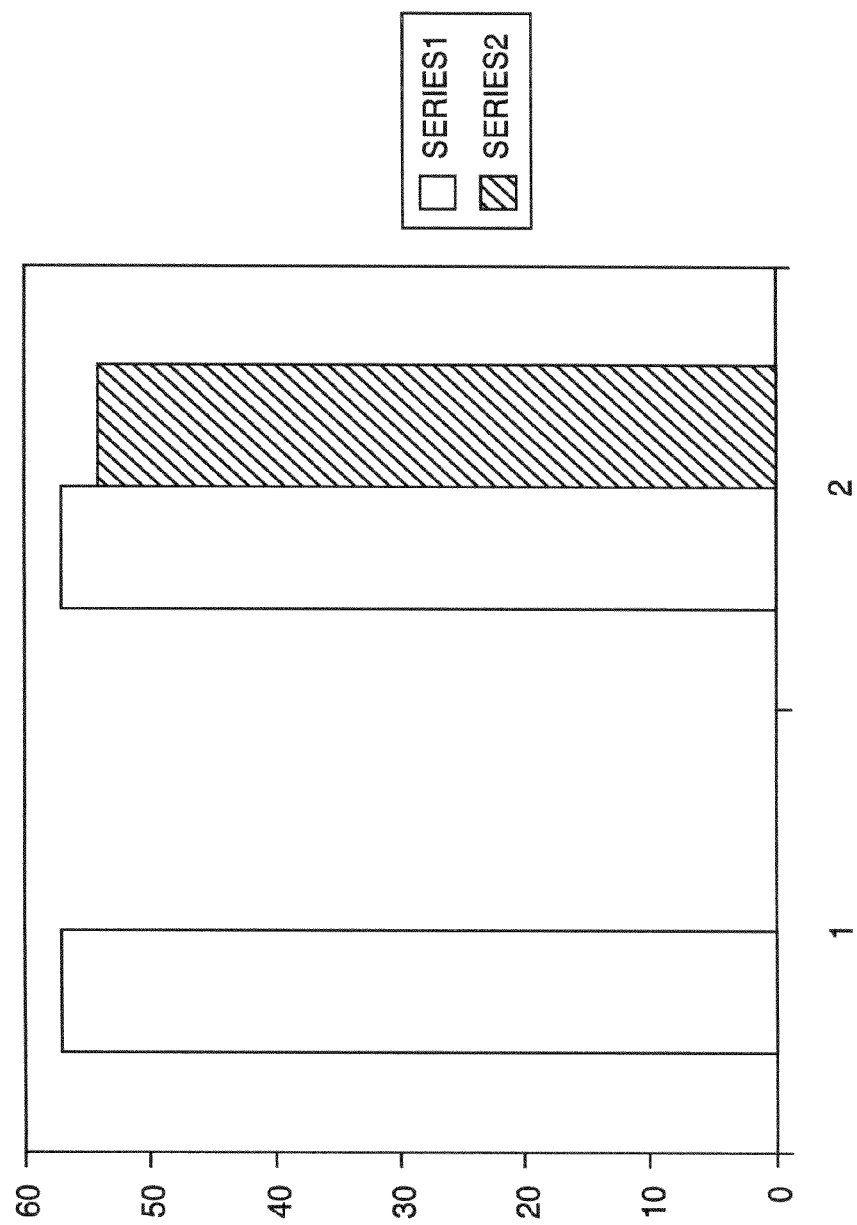

FIG. 52 depicts a graph indicating the fluorescence intensity of in vitro produced and purified BODIPY-FL and PDBA labeled GST spotted on a PVDF membrane. Sample set 1 represents the intensity of the BODIPY-FL (left) and PDBA (right) labeled GST spotted on the membrane. Sample set 2 represents the intensity of the same samples (BODIPY-FL (left) and PDBA (right) labeled GST) after incubation with BODIPY-FL-bis(SHA).

FIG. 53 illustrates determination of specific labeling for the in vitro produced proteins labeled at the N-terminus with BODIPY-FL-VAL. A) calibration curves obtained for protein standards labeled with BODIPY-FL; B) calibration curves obtained for protein standards using SYPRO-Orange stain; C) table illustrating determined yield and specific labeling for 3 different in vitro produced proteins.

Figure 54:
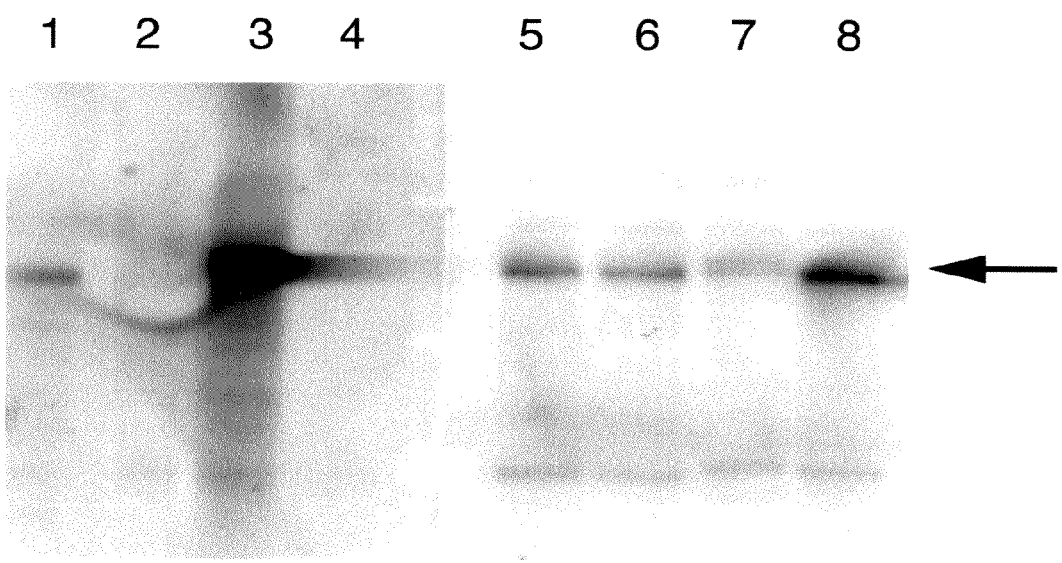

FIG. 54 illustrates detection of in vitro synthesized p53 protein on the Western blot using detection of biotin/PC-biotin incorporated into protein via the tRNAs (lanes 1-4) or using anti-HSV antibody-alkaline phosphatase directed at the HSV epitope incorporated into protein (lanes 5-8). Translations were performed in rabbit reticulocyte extract and 1 μl aliquots were separated on the gradient SDS-PAGE and transferred to membrane. Lanes: 1,5-biotin-Lys-tRNA$^{Lys}$ (tRNA$^{scend}$, Promega Corp.), lanes 2,6-α-$NH_2$, ε-PC-Biotin-Lys-tRNA$^{TOTAL}$, lane 3,7-α-$NH_2$, ε-Biotin-Lys-tRNA$^{TOTAL}$, lanes 4,8-no tRNA added.

Figure 55:
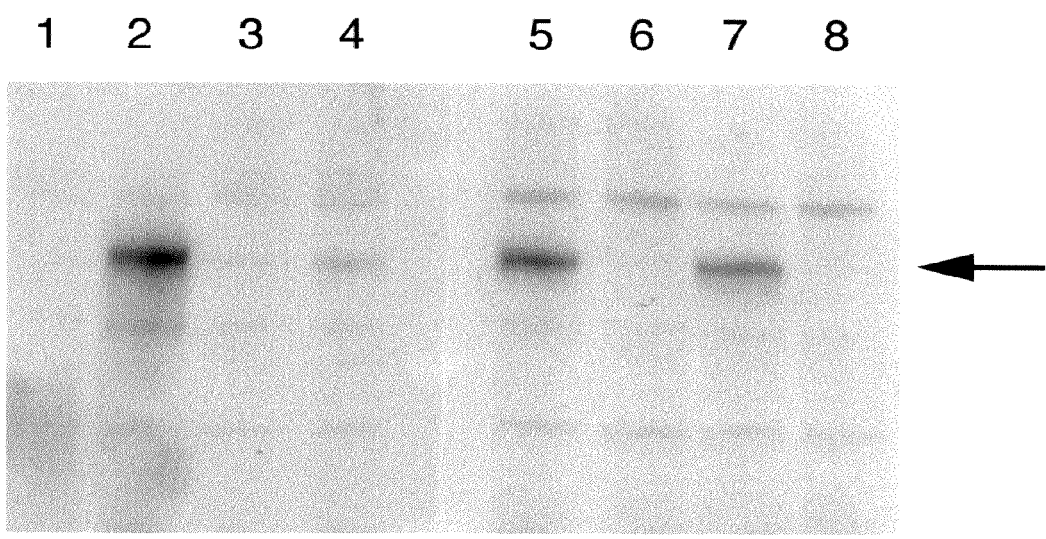

FIG. 55 illustrates detection of in vitro synthesized p53 protein on the Western blot using detection of biotin/PC-biotin incorporated into protein via the tRNAs (lanes 1-4) or using anti-HSV antibody-alkaline phosphatase directed at the HSV epitope incorporated into protein (lanes 5-8). Lanes: 1, 2, 7, 8-biotin-Lys-tRNA$^{Lys}$ (tRNA$^{scend}$, Promega Corp.), lanes 3, 4, 5, 6-α-$NH_2$, ε-PC-Biotin-Lys-tRNA$^{TOTAL}$ lanes 2, 4, 5, 7 DNA template added, lanes 1, 3, 6, 8-no DNA template added.

Figure 56:
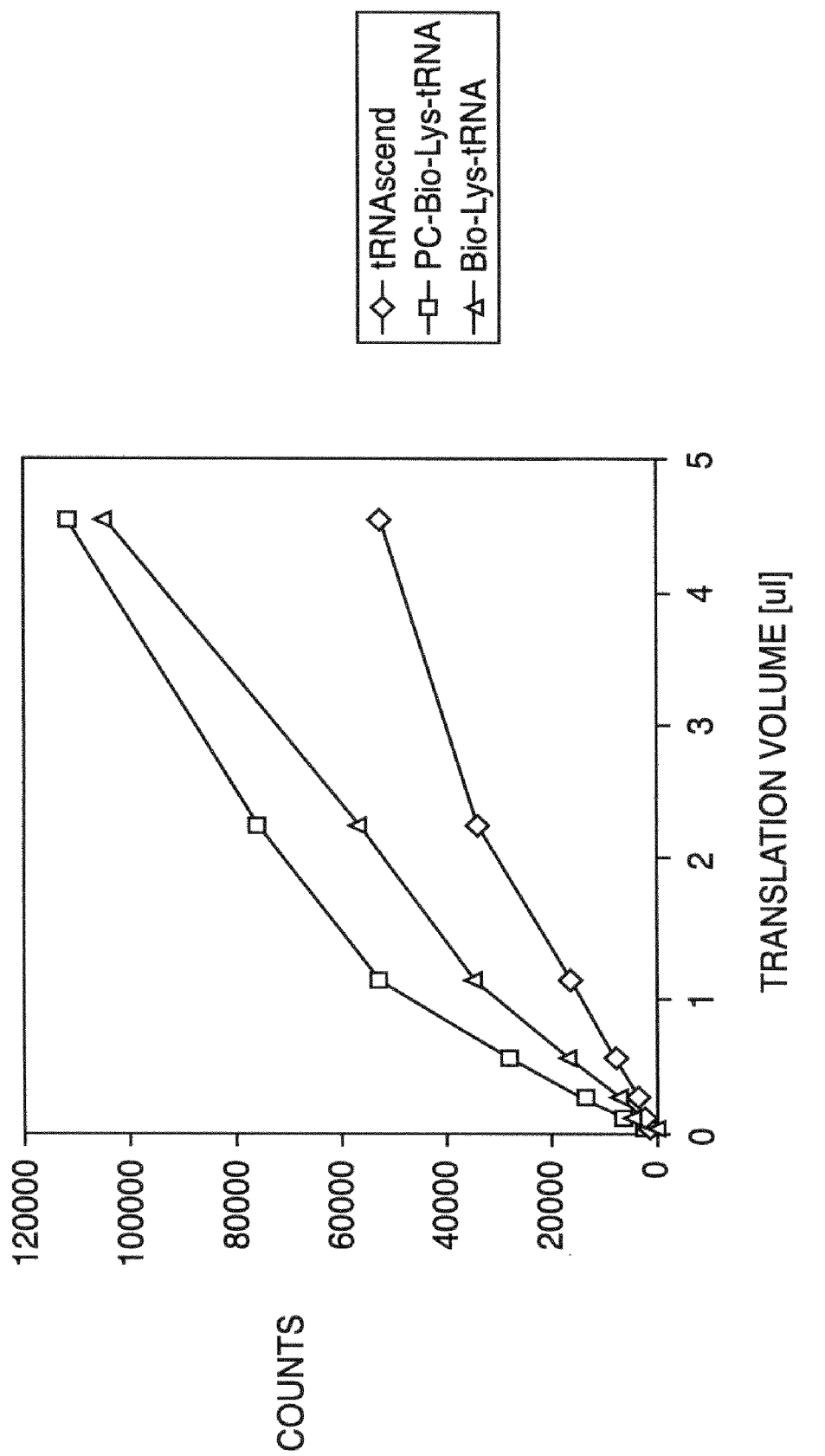

FIG. 56 illustrates selective capture on streptavidin coated plate of translation product (p53 protein) produced in the rabbit reticulocyte translation system followed by detection of the HSV epitope on the p53 protein by the anti-HSV-alkaline phosphatase conjugate and chemiluminescent substrate. The tRNAs used in the translation were: biotin-Lys-tRNA$^{Lys}$ (tRNA$^{scend}$, Promega Corp.)(♦), α-$NH_2$, ε-PC-Biotin-Lys-tRNA$^{TOTAL}$ (■) and α-$NH_2$, ε-Biotin-Lys-tRNA$^{TOTAL}$ (▲).

Figure 57:
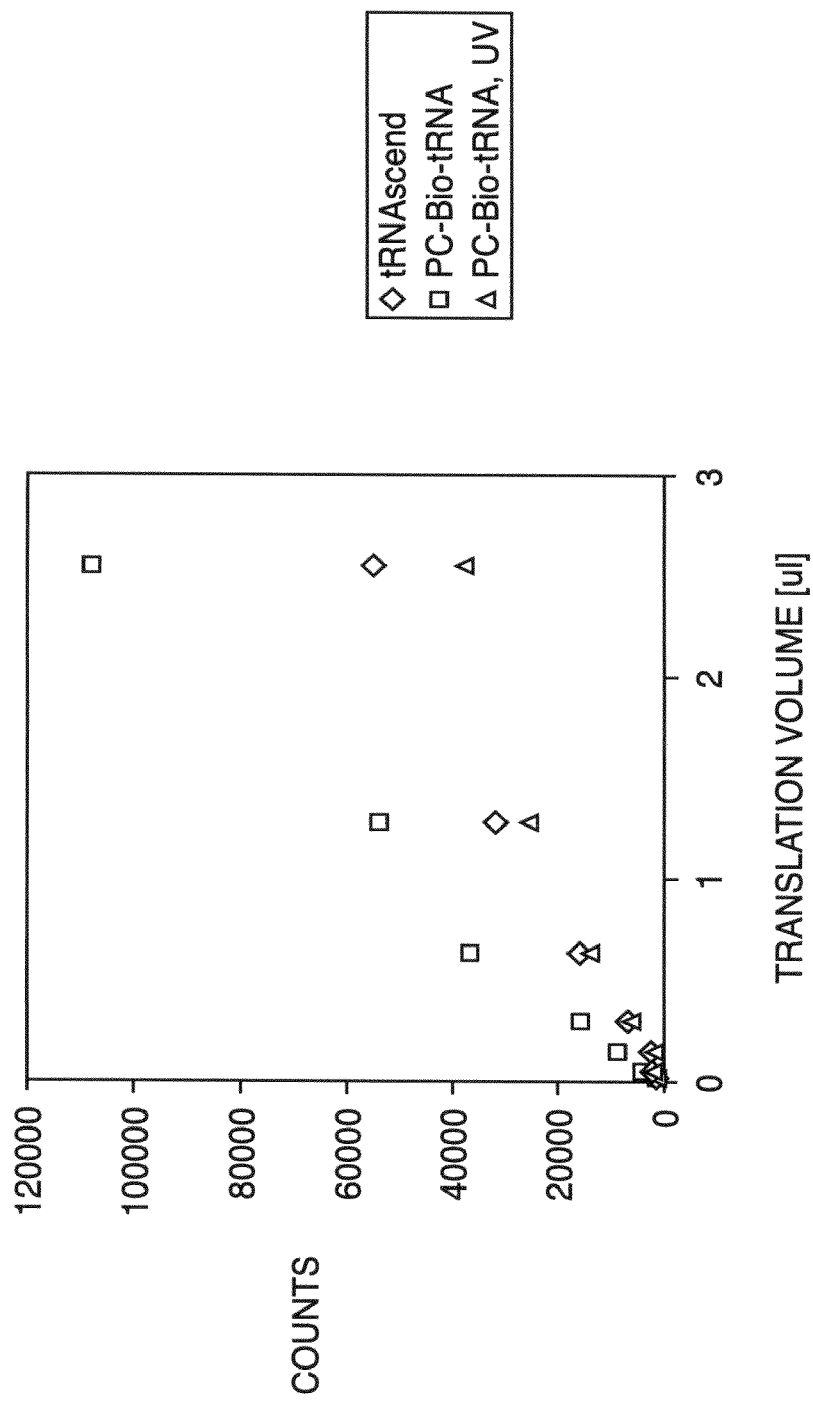

FIG. 57 shows the tRNAs used in the translation were: biotin-Lys-tRNA$^{Lys}$ (tRNA$^{scend}$, Promega Corp.)(♦), α-$NH_2$, ε-PC-Biotin-Lys-tRNA$^{TOTAL}$ (■) and α-$NH_2$, ε-PC-Biotin-Lys-tRNA$^{TOTAL}$ (sample irradiated with UV light prior to assay)(▲).

Figure 58A:
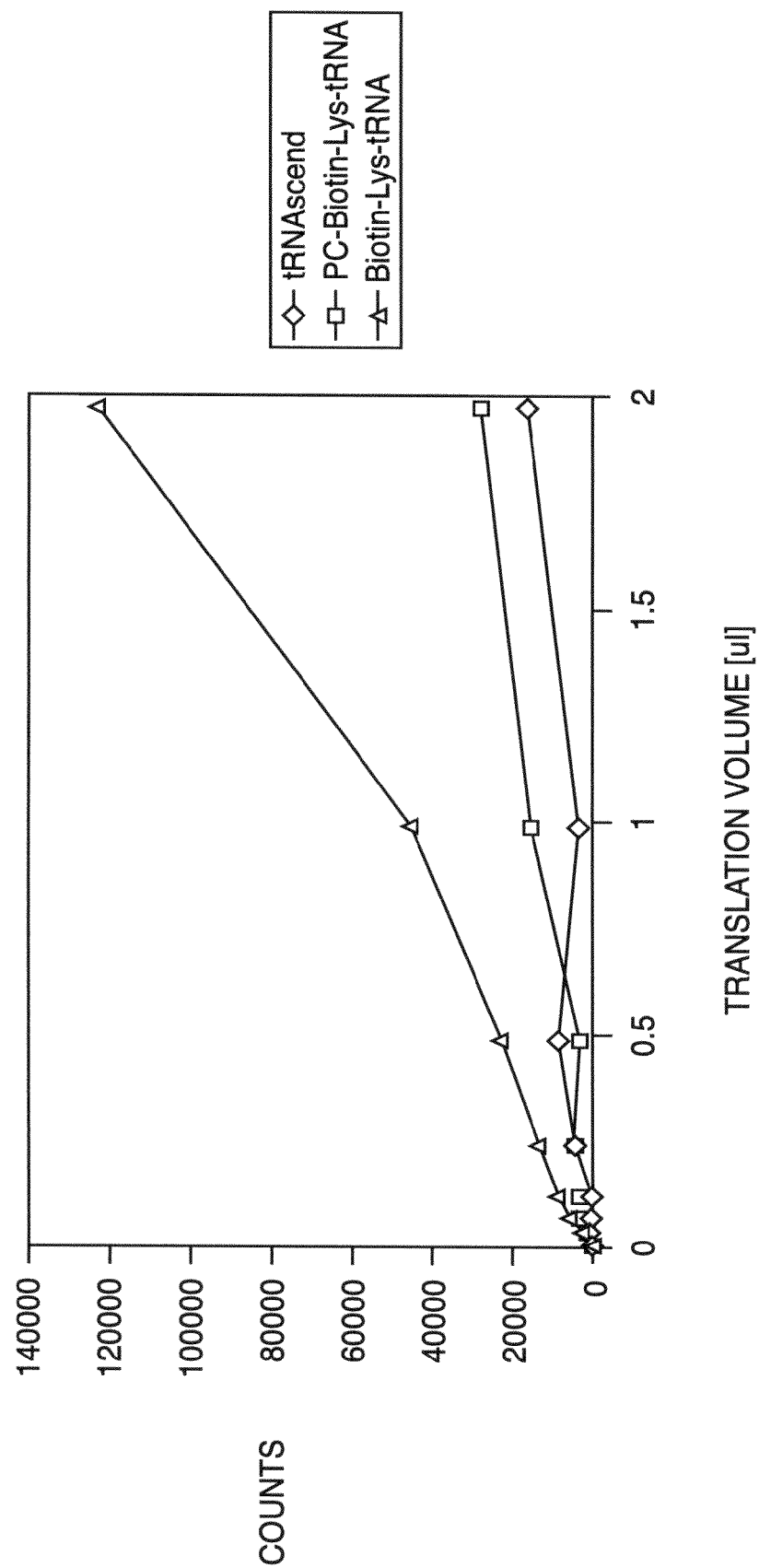
Figure 58B:
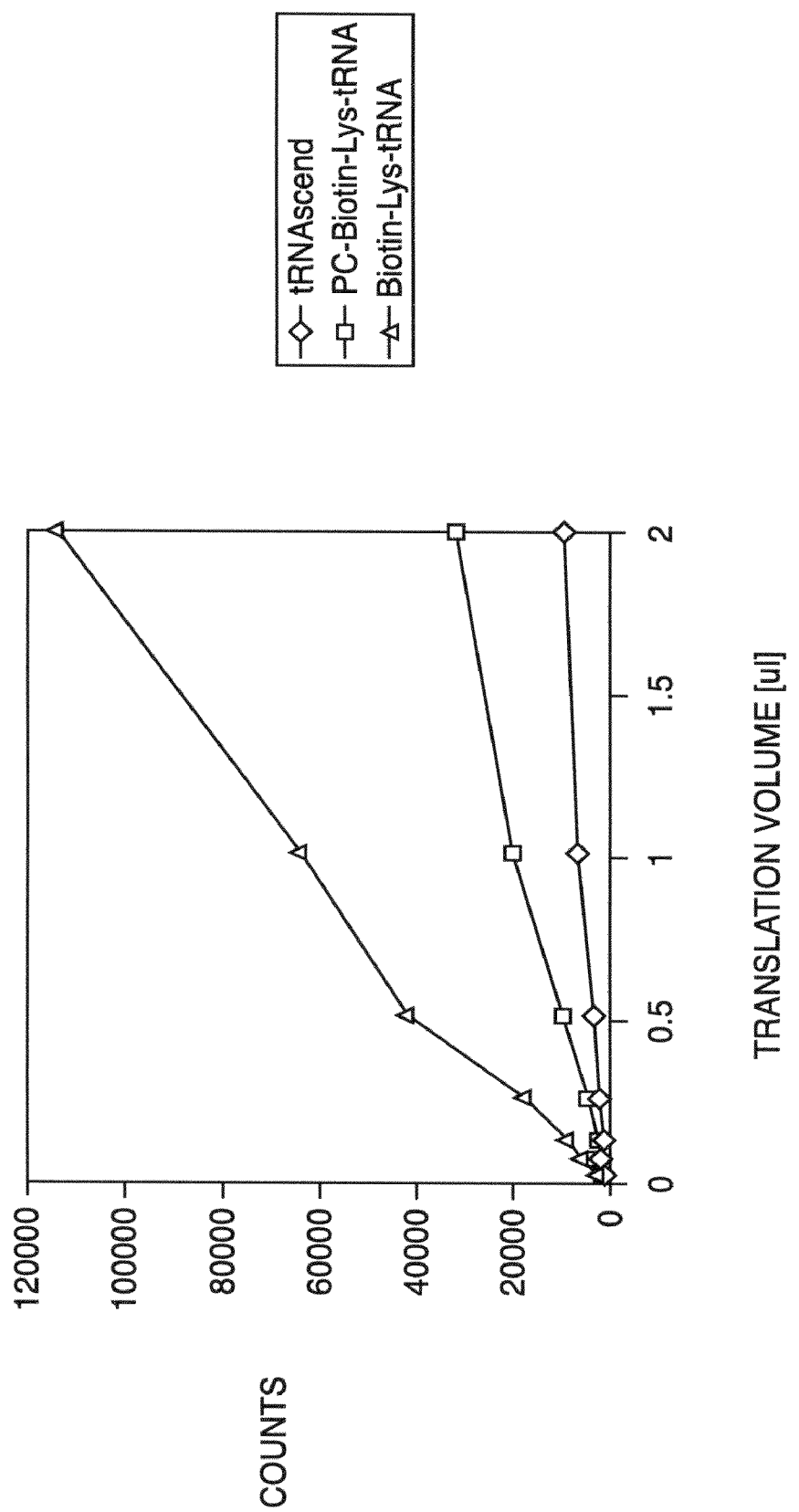

FIG. 58 illustrates selective capture on anti-HSV antibody coated plate of translation product (p53 protein) produced in the rabbit reticulocyte translation system followed by detection of the incorporated biotin on the p53 protein by the streptavidin-alkaline phosphatase conjugate and chemiluminescent substrate. Assay was performed under native (A) and denaturing (B) conditions, the tRNAs used were: biotin-Lys-tRNA$^{Lys}$ (tRNA$^{scend}$, Promega Corp.)(♦), α-$NH_2$, ε-PC-Biotin-Lys-tRNA$^{TOTAL}$ (■) and α-$NH_2$, ε-Biotin-Lys-tRNA$^{TOTAL}$ (▲).

Figure 59A:
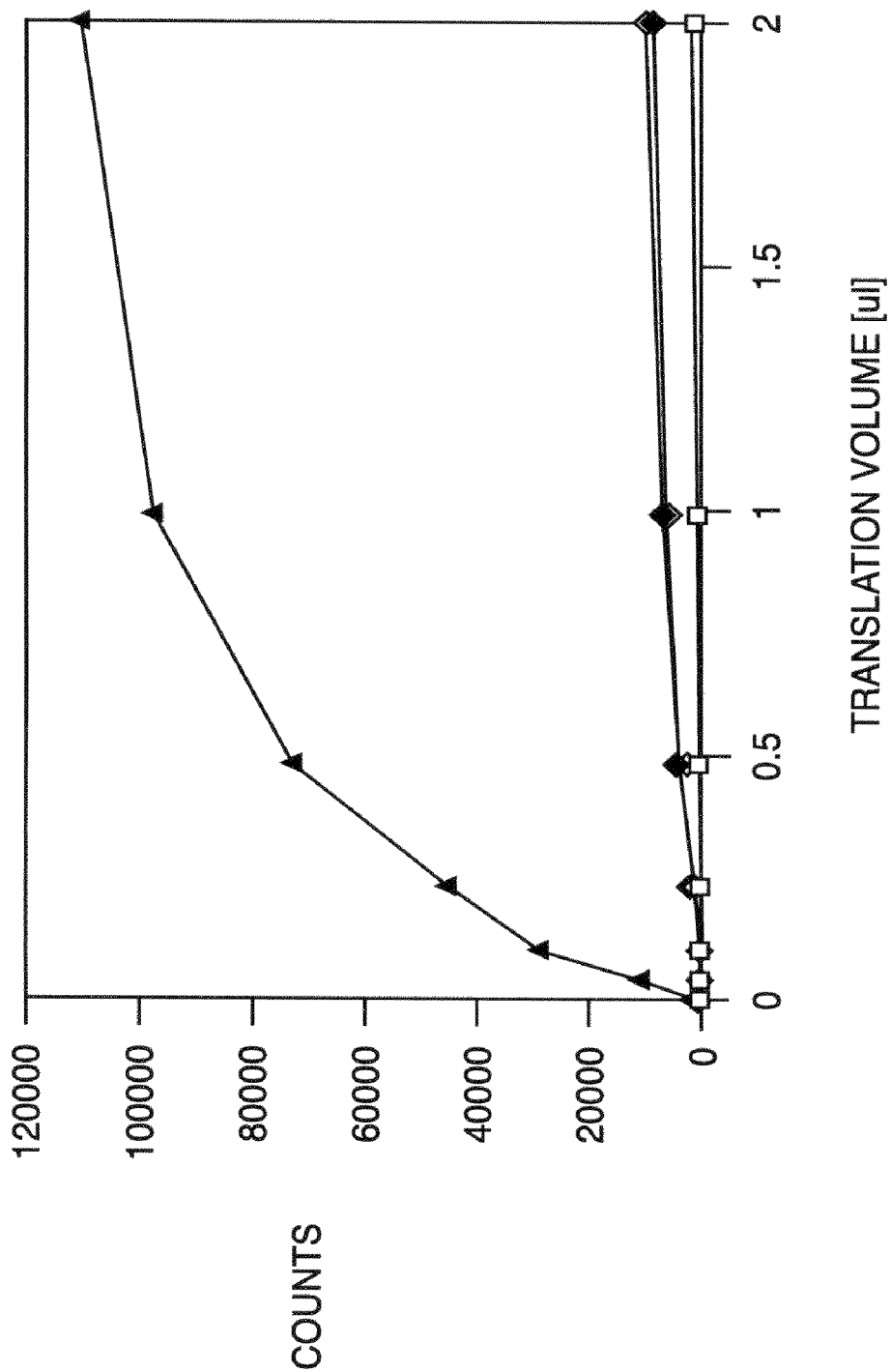
Figure 59B:
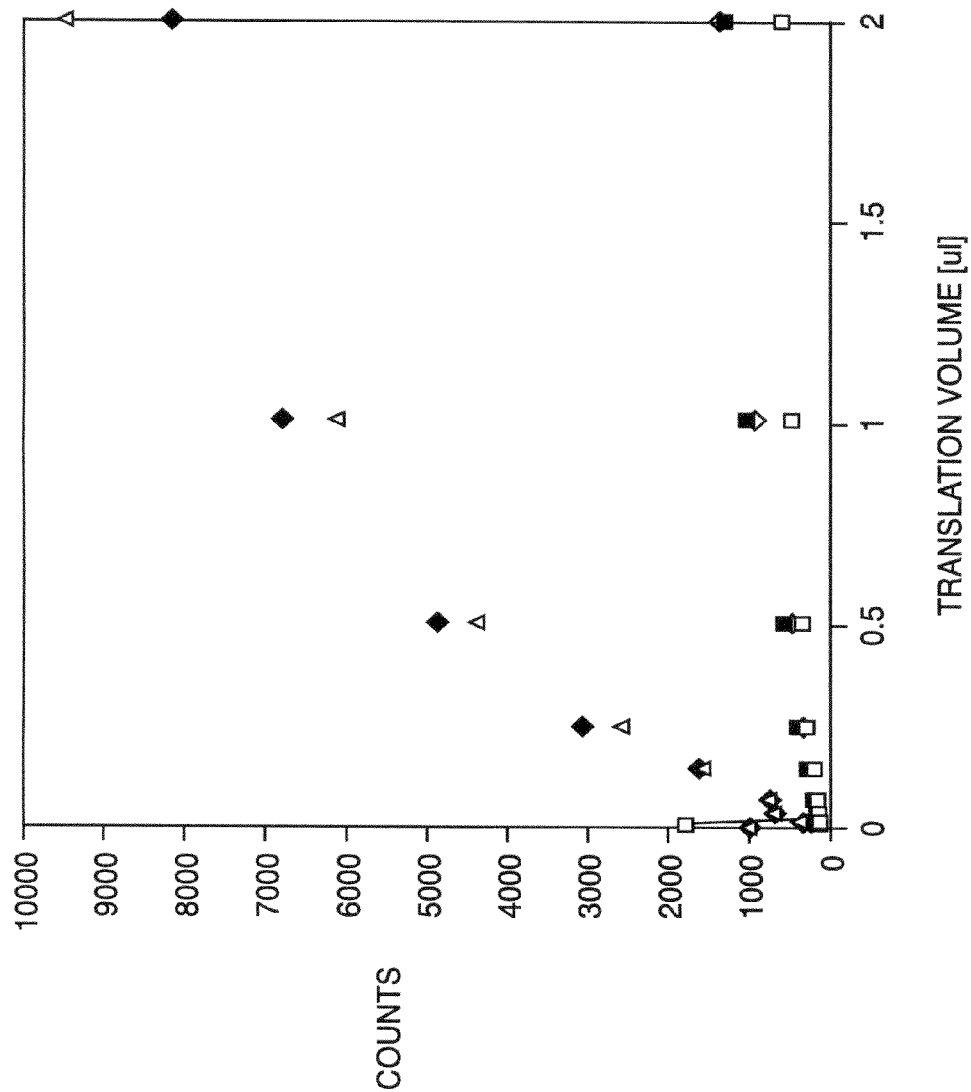

FIG. 59 illustrates selective capture on anti-HSV antibody coated plate of translation product (β-tubulin) produced in the S-30 E. coli translation system followed by detection of the incorporated biotin on the protein by the streptavidin-alkaline phosphatase conjugate and chemiluminescent substrate. Assay was performed under denaturing and native conditions, the tRNAs used were: biotin-Lys-tRNA$^{Lys}$ (tRNA$^{scend}$, Promega Corp.)(♦ denaturing, ◊ native), α-$NH_2$, e-PC-Biotin-Lys-tRNA$^{TOTAL}$ (■ denaturing, □ native) and α-$NH_2$, ε-Biotin-Lys-tRNA (▲ denaturing, Δ native). A—Complete set of data points, B—all data points except for the α-$NH_2$, ε-Biotin-Lys-tRNA$^{TOTAL}$ (▲ denaturing).

DETAILED DESCRIPTION OF THE INVENTION

The present invention is directed to methods for the preparation of chemically aminoacylated tRNAs for the purpose of the introduction of markers into nascent proteins. The present invention is also directed to methods for the non-radioactive labeling, detection, quantitation and isolation of nascent proteins translated in a cellular or cell-free translation system utilizing chemically aminoacylated tRNAs.

I. Preparation of Chemically Aminoacylated tRNAs

Figure 1:
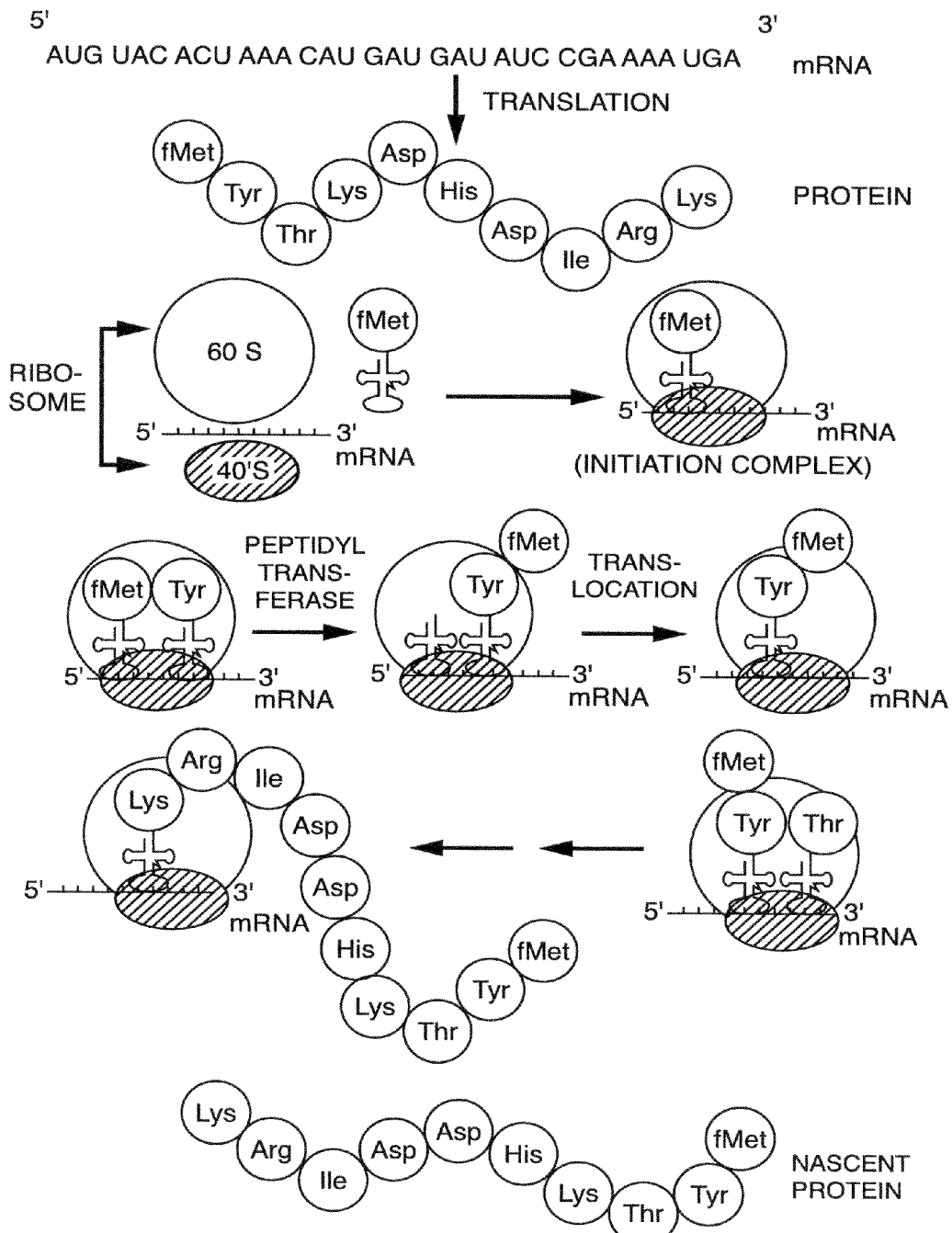
FIG. 1 (SEQ ID NOS: 5-7) provides a description of the molecular steps that occur during protein synthesis in a cellular or cell-free system.
Figure 2:
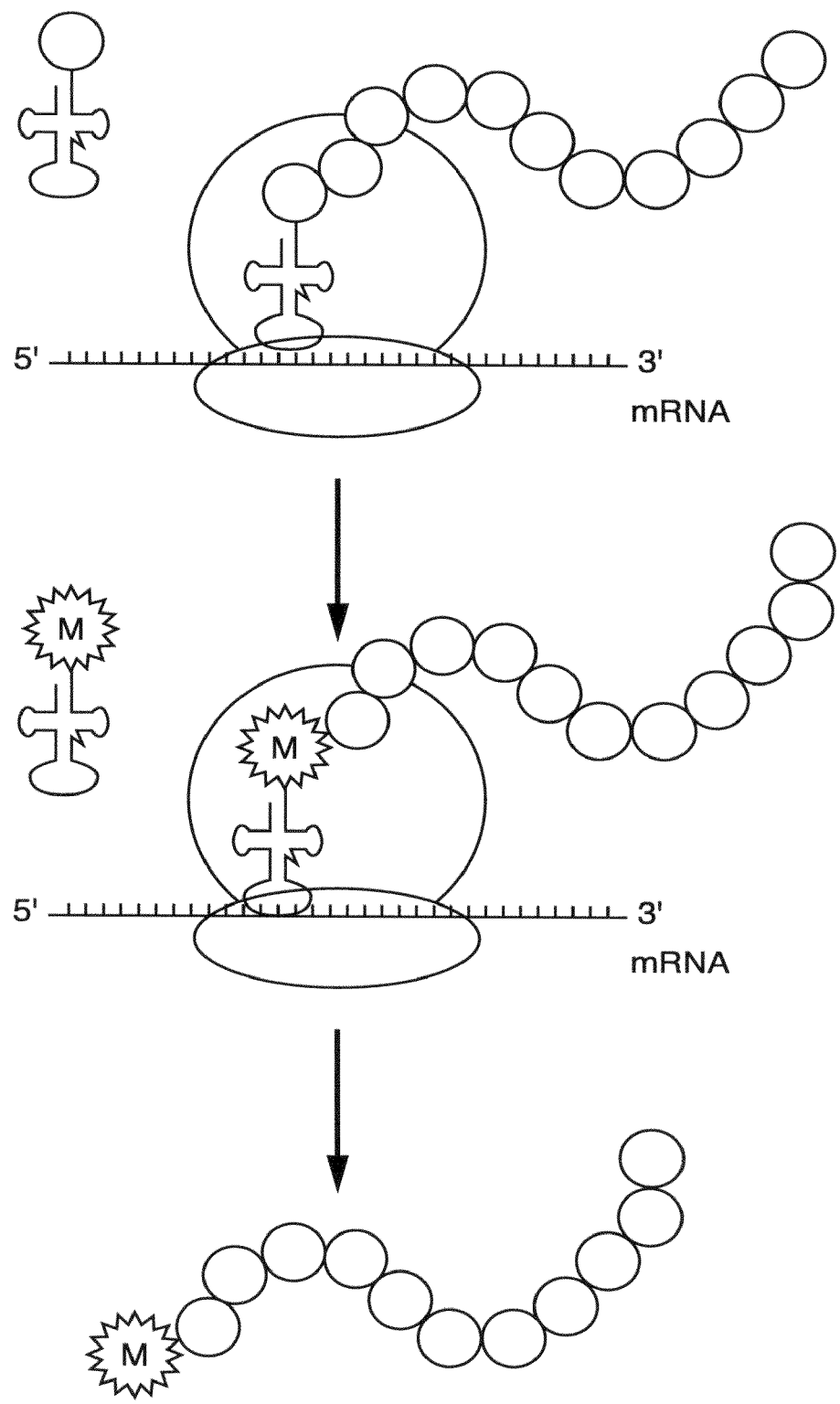
FIG. 2 shows protein synthesis in a cellular or cell-free system, wherein tRNA delivers a marker molecule "M" into a nascent protein.
Figure 3:
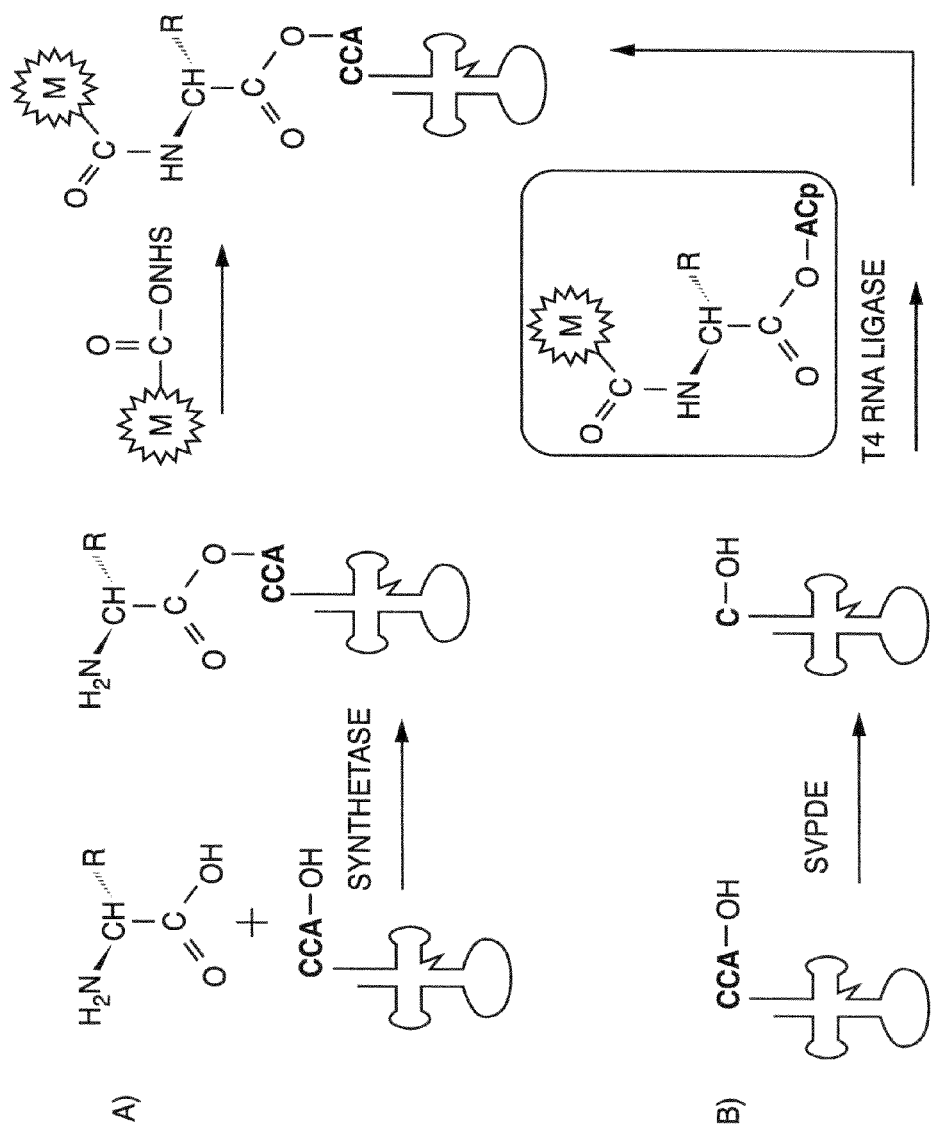
FIG. 3 shows one approach for preparation of marker-carrying tRNA molecules by chemical aminoacylation wherein two nucleotides from the 3'-terminus of tRNA are removed using enzymes (e.g. SVPDE) followed by ligation to chemically prepared (2') 3'-O-aminoacyl-pdCpA (dinucleotide) comprising a marker moiety.
Figure 4A:
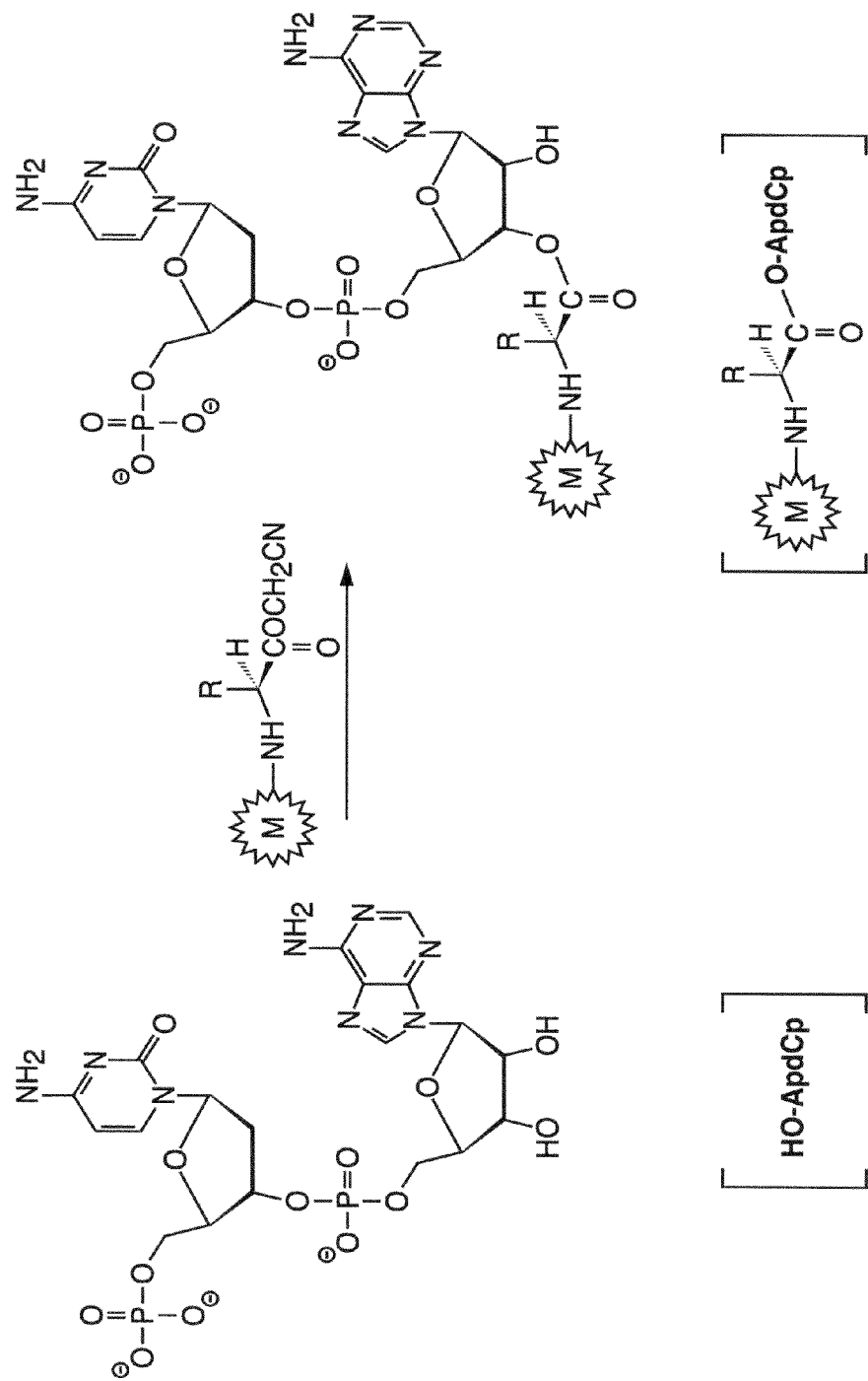
FIG. 4A shows one method for the chemical aminoacylation process of a pdCpA dinucleotide. Amino acid modified with a marker molecule is converted into active ester (such as cyanomethyl ester) and then specifically reacted with the (2') 3'-OH groups on the ribose ring.
Figure 4B:
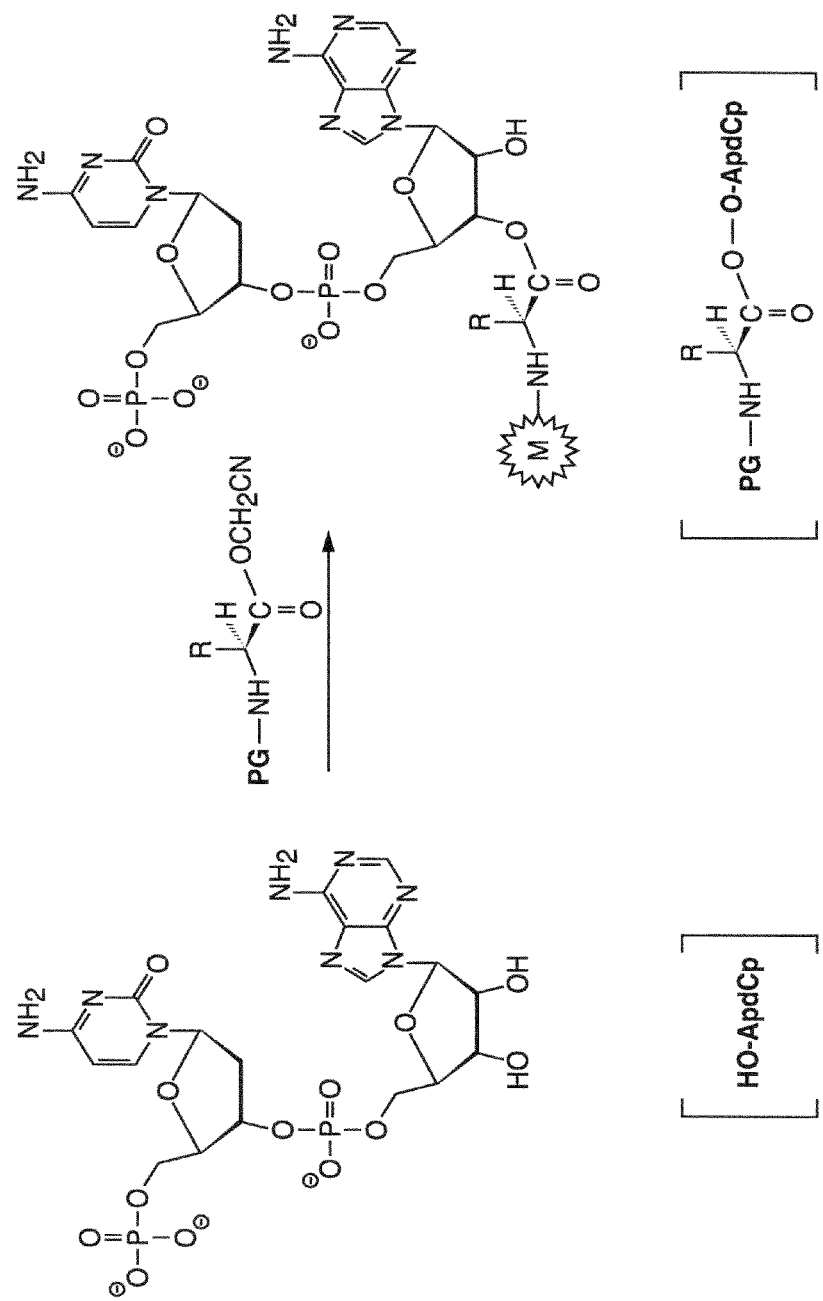
FIG. 4B shows one embodiment for the chemical aminoacylation of a pdCpA dinucleotide wherein an amino acid (e.g. native or non-native), carrying protective group PG is converted into cyanomethyl ester and reacted with the (2') 3'-OH groups on the ribose ring of the pdCpA dinucleotide. This figure provides more structural detail to Step (a) of FIG. 5.

The present invention is directed to methods for the preparation of chemically aminoacylated tRNAs, carrying fluorescent labels or markers. Markers which are aminoacylated to tRNA molecules, may comprise native amino acids, non-native (i.e. unnatural) amino acids, amino acid analogs or derivatives, or chemical moieties. These markers are introduced into nascent proteins from the resulting misaminoacylated tRNAs during the translation process. Aminoacylation is the process whereby a tRNA molecule becomes charged. When this process occurs in vivo, it is referred to as natural aminoacylation and the resulting product is an aminoacylated tRNA charged with a native amino acid. When this process occurs through artificial means, it is called misaminoacylation and a tRNA charged with anything but a native amino acid molecule is referred to as a misaminoacylated tRNA. The principal of chemical aminoacylation is shown in FIG. 3.

The misaminoacylated tRNA can be formed by natural aminoacylation using cellular enzymes, or by misaminoacylation such as chemical misaminoacylation. One type of chemical misaminoacylation involves truncation of the tRNA molecule to permit attachment of the marker or marker precursor. For example, successive treatments with periodate plus lysine, pH 8.0, and alkaline phosphatase removes 3'-terminal residues of any tRNA molecule generating tRNA-OH-3' with a mononucleotide or dinucleotide deletion from the 3'-terminus (Neu & Heppel, *J. Biol. Chem.*, 239: 2927-34 (1964)). Alternatively, tRNA molecules may be genetically manipulated to delete specific portions of the tRNA gene. The resulting gene is transcribed producing truncated tRNA molecules (Sampson and Uhlenbeck, *Proc. Natl. Acad. Sci., USA*, 85: 1033-37 (1988)). Next, a dinucleotide is chemically linked to a modified amino acid or other marker by, for example, acylation. Using this procedure, markers can be synthesized and acylated to dinucleotides in high yield (Hudson, *J. Org. Chem.*, 53: 617-624 (1988); Happ et al., *J. Org. Chem.*, 52: 5387-91, (1987)). These modified groups are bound together and linked via the dinucleotide to the truncated tRNA molecules in a process referred to as ligase coupling.

tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wis.; Roche Biochemicals; Indianapolis, Ind.). Their isolation and purification mainly involves cell-lysis, phenol extraction followed by chromatography on DEAE-cellulose. Amino-acid specific tRNA, for example tRNA$^{fMet}$, can be isolated by expression from cloned genes and overexpressed in host cells and separated from total tRNA by techniques such as preparative polyacrylamide gel electrophoresis followed by band excision and elution in high yield and purity (Seong & RajBhandary, *Proc. Natl. Acad. Sci. USA*, 84: 334-338 (1987)). Run-off transcription allows for the production of any specific tRNA in high purity, but its applications can be limited due to lack of post-transcriptional modifications (Bruce & Uhlenbeck, *Biochemistry*, 21: 3921 (1982)).

In one embodiment of the present invention, tRNA is aminoacylated as follows. Specifically, the tRNA of interest is first treated chemically (for example, using periodate) or enzymatically (for example, using Snake Venom Phosphodiesterase (SVPDE)) to selectively remove last two nucleotides from the 3'-end (i.e. the "-CA" moiety). (See Examples 18 & 19). The 5'-phosphorylated dinucleotide hybrid (pdCpA) is then synthesized chemically and the 2'(3') OH group of the adenosine moiety is selectively aminoacylated using amino-acid-marker conjugate. (See FIGS. 3 & 18, and Examples 1-6, 18).

This approach, although very useful, has many limitations. First, for each marker-aminoacid conjugate, a separate synthesis involving several protection/deprotection steps needs to be carried out. Such a synthesis scheme is problematic, especially in the case of fluorescent dyes which often carry many reactive groups that need to be protected in order to be used in the chemical aminoacylation approach. Second, certain fluorescent markers are sensitive to the chemical steps utilized in the preparation of activated marker-amino acid conjugates, and attempts to prepare said conjugates using traditional methods fail. For example, an attempt to first conjugate BODIPY-FL to methionine or valine via an amino group, followed by a conversion to active cyanomethyl ester (typically used in the chemical aminoacylation approach) results in destruction of the BODIPY-FL fluorophore at this stage.

The present invention contemplates approaches that overcome this problem. For example, in some embodiments, labeling is performed after chemical aminoacylation using markers and dyes that are available in the chemically reactive form (such as NHS esters, maleimide derivatives, hydrazides, thiosemicarbazides) with reactivity selectively directed at specific entities, such as amino, sulfhydryl, aldehyde or ketone groups. These reactions usually occur at very mild conditions and are relatively fast.

In addition to chemically reactive markers, a variety of molecules capable of forming stable covalent (or non-covalent) complexes exist (e.g. biotin-streptavidin, antigen-antibody, chelates-metal ions, salicylhydroxamic acid-phenyldiboronic acid complexes). (See, e.g., FIGS. 14 & 15 and U.S. Pat. No. 6,156,884 to Ahlem et al. and U.S. Pat. No. 6,124,471 to Stolowitz et al., herein incorporated by reference). In such cases, these so-called "stealth" or "binary" markers are initially incorporated into protein via aminoacyl tRNAs and the "detection complexes" are formed after the translation is finished by incubation of the protein containing the "first" maker with a solution containing the second "half" of the binary marker. This method is advantageous, since the efficiency of incorporation of modified amino acids into proteins in the cell-free systems decreases rapidly as the size of the fluorophore increases. The detection complex is formed by a specific interaction between two markers and the complex is detected by, for example, fluorescence.

Figure 17:
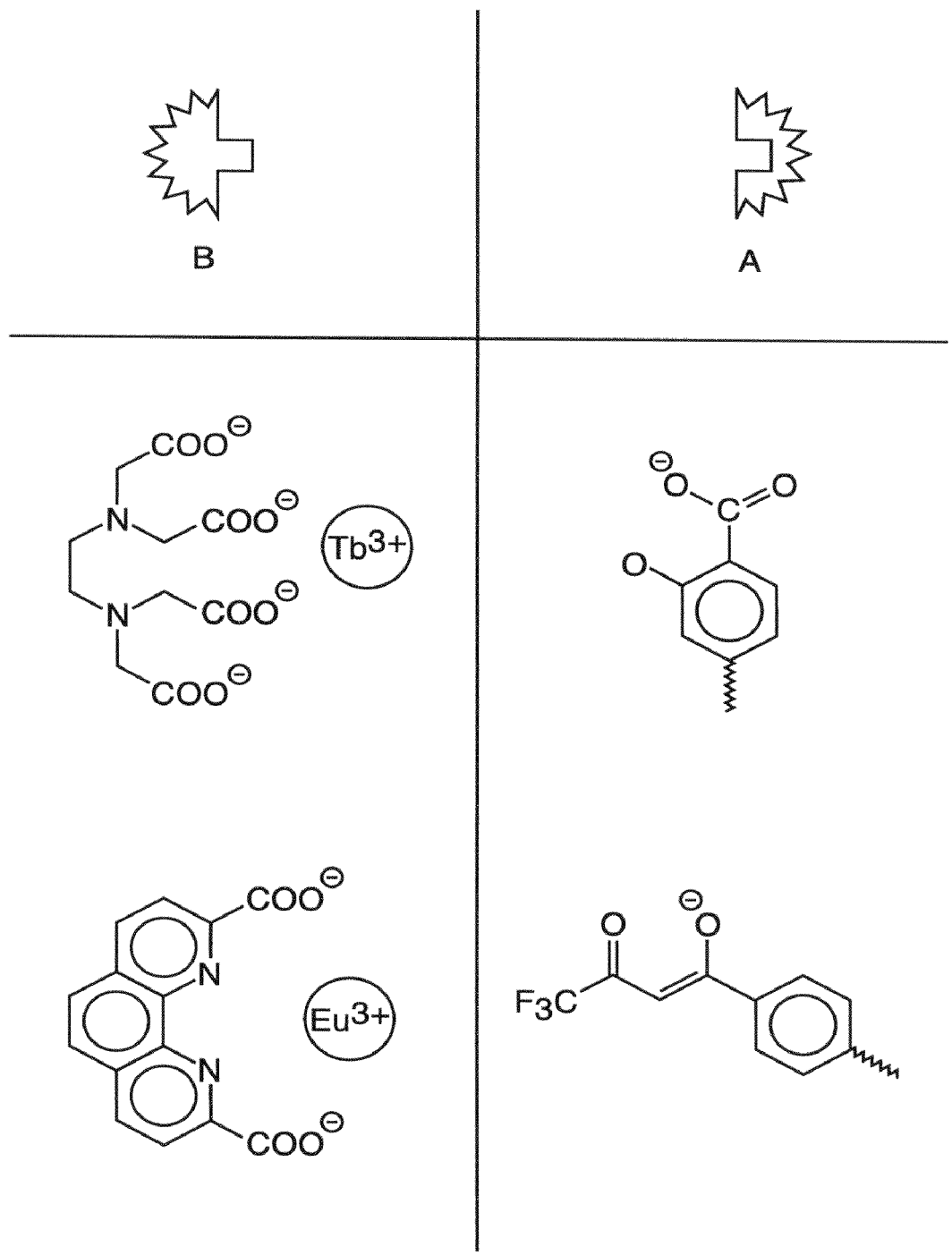
FIG. 17 depicts examples of linkers A and B that are capable of forming detectable marker molecules upon interaction: EDTA-Tb-salicylic acid, 2,9-dicarboxy, 1,10-phenantroline-Eu-benzoyltrifluoroacetone.

Some preferred embodiments of the present invention utilize chelators. (See FIG. 17). For example, in one embodiment, a first chelator is incorporated into tRNA. Next, a second chelator is added free in solution, together with metal ion, and the luminescent complex is then formed. The first and second chelators may be the same or different. Table 1 below summarizes particularly useful embodiments involving chelators and metal ions:

TABLE 1

| First Chelator | Second Chelator | Metal Ion(s) |
| --- | --- | --- |
| salicylic acid | EDTA | $Tb^{3+}$ |
| 3-hydroxypyridine | 1,10-phenantroline | $Eu^{3+}$ |
| β-diketone (β-naphthoyl-trifluoroacetone, NTA) | EDTA | $Tb^{3+}$, $Eu^{3+}$, or $Sm^{3+}$ |
| β-diketone (β-pivaloyl-trifluoroacetone, PTA) | EDTA | $Tb^{3+}$ or $Eu^{3+}$ |
| 2,2'-bipyridine (Bipy) | EDTA or 2,2'-bipyridine | $Ru^{3+}$ |

Figure 11:
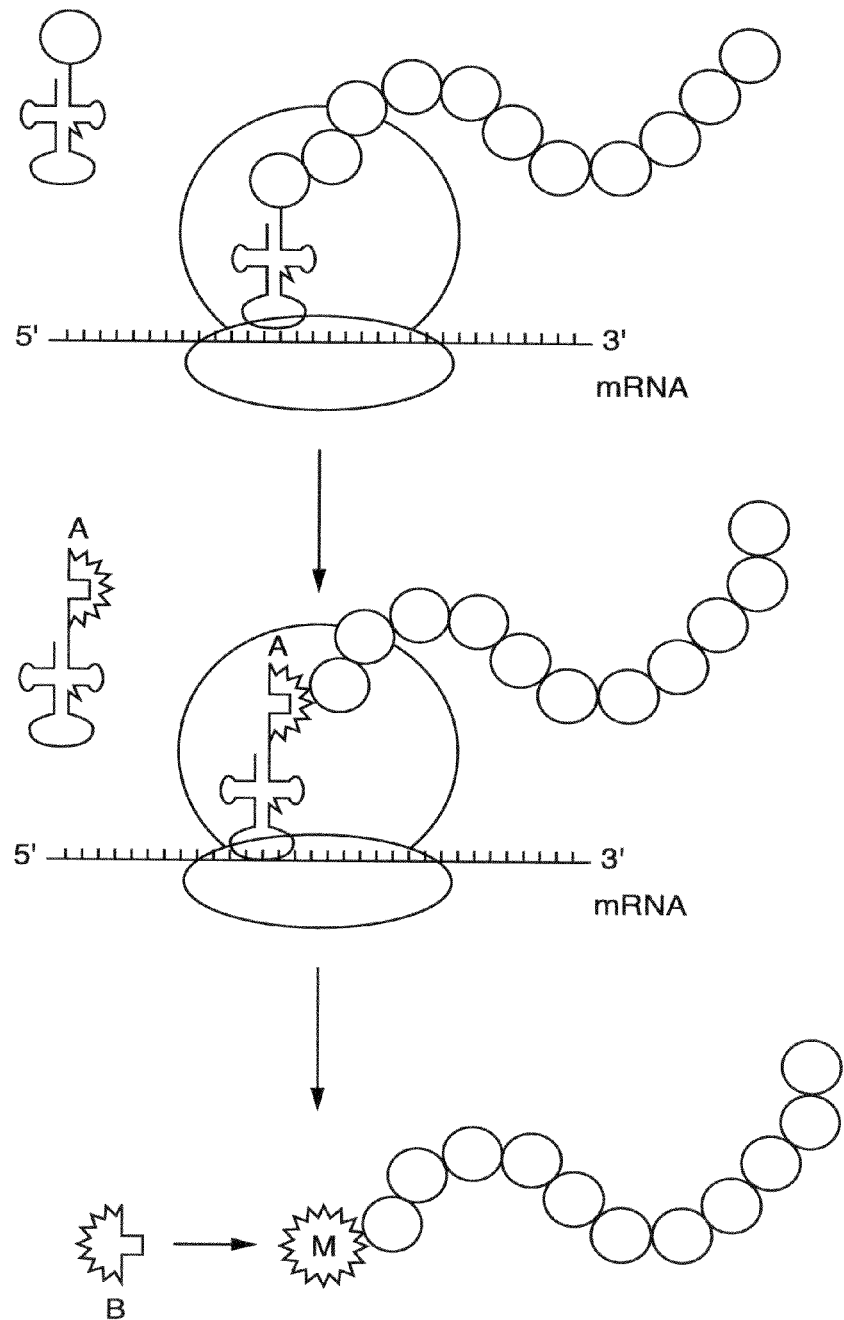
FIG. 11 shows one example of the introduction of linker molecule A into the nascent protein via the tRNA. In the next step, the nascent protein with linker molecule A incorporated in a site-specific manner interacts with linker molecule B in solution, which results in formation of detectable marker molecule M.
Figure 12:
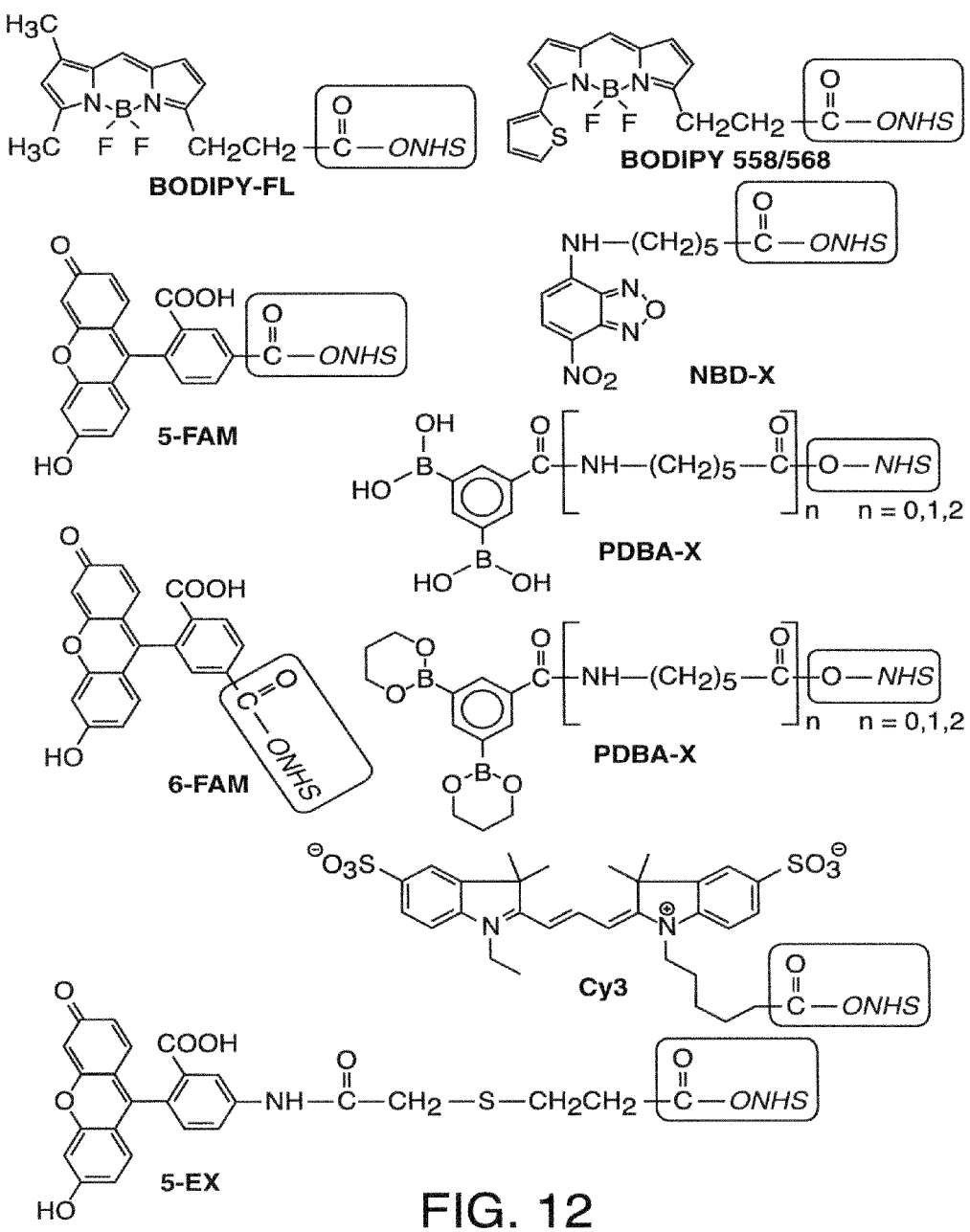
FIG. 12 shows several examples of marker molecules: BODIPY-FL, BODIPY 558/568, fluorescein (5-FAM, 6-FAM, 5-EX), NBD-X, phenyldiboronic acid (PDBA)-X, cyanine 3 (Cy3) in the form of reactive NHS esters.
Figure 14:
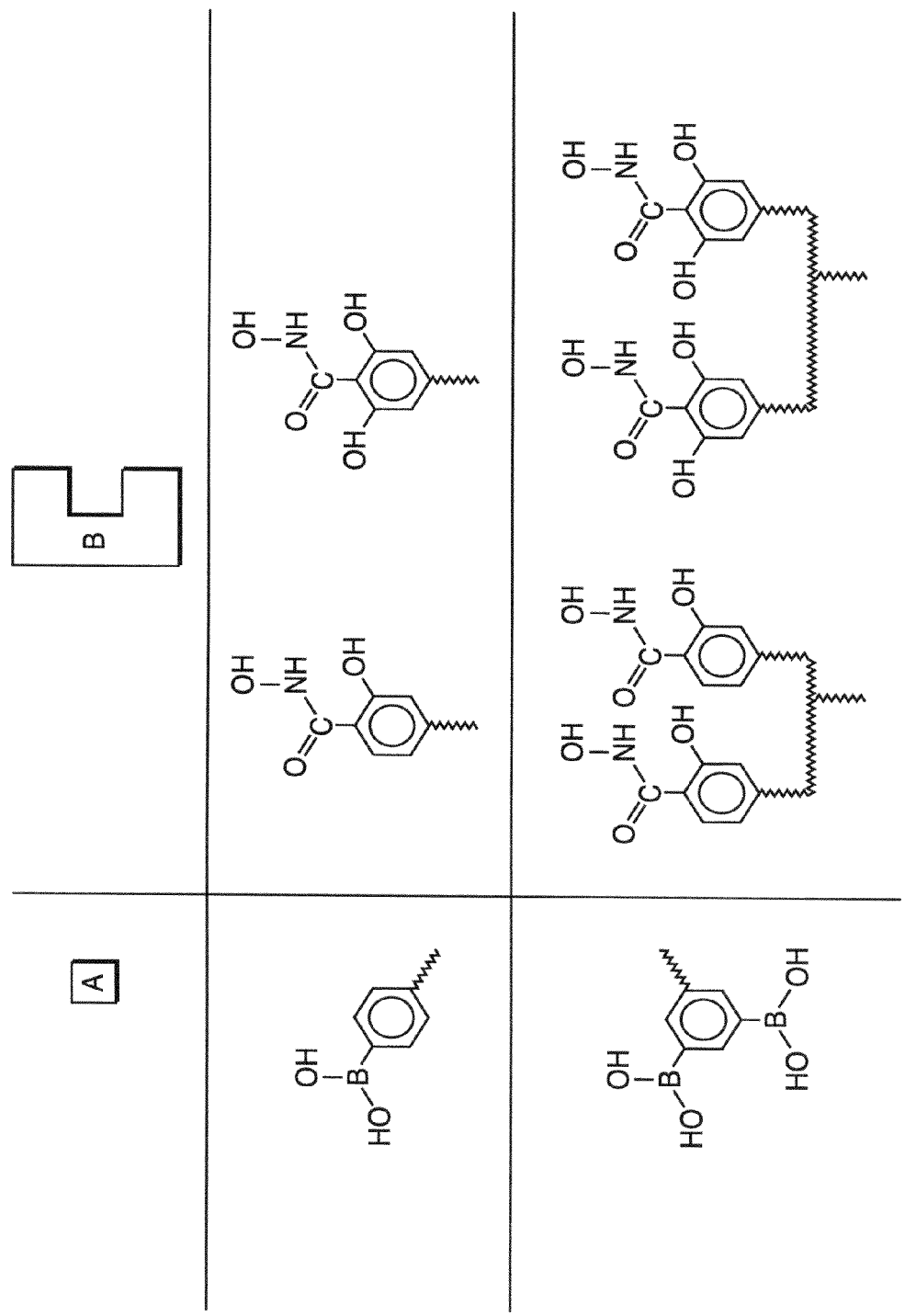
FIG. 14 shows examples of linker molecules A (e.g. phenylboronic acid, phenyldiboronic acid) and B (e.g. salicylhydroxamic acid, 2,6-dihydroxybenzhydroxamic acid, bis(salicylhydroxamic) acid, bis(2,6-dihydroxybenzhydroxamic) acid).
Figure 15:
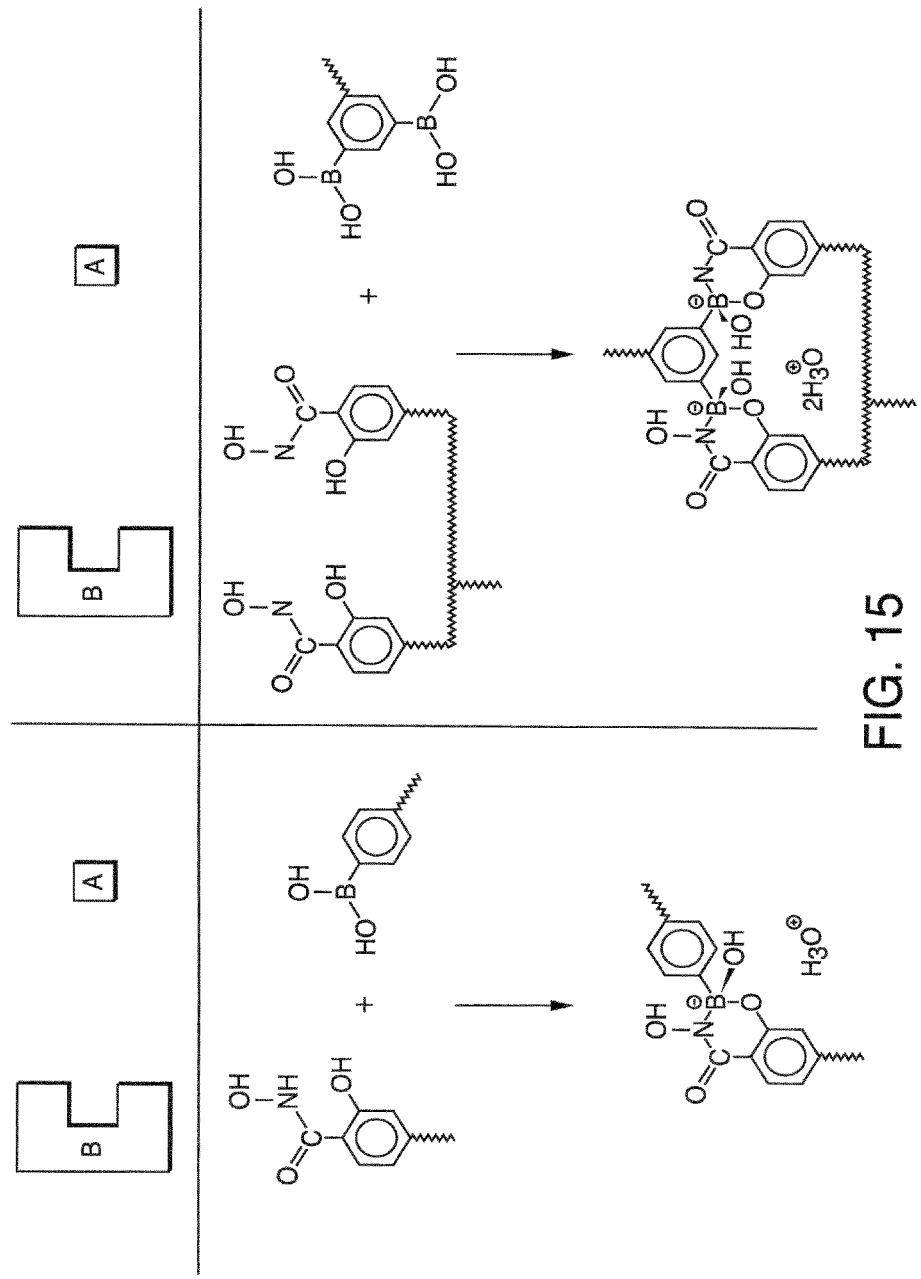
FIG. 15 shows one example of the interaction between linkers A and B and formation of stable complexes. Left—interaction between salicylhydroxamic acid and phenylboronic acid; Right—interaction between bis(salicylhydroxamic) acid and phenyldiboronic acid.
Figure 16:
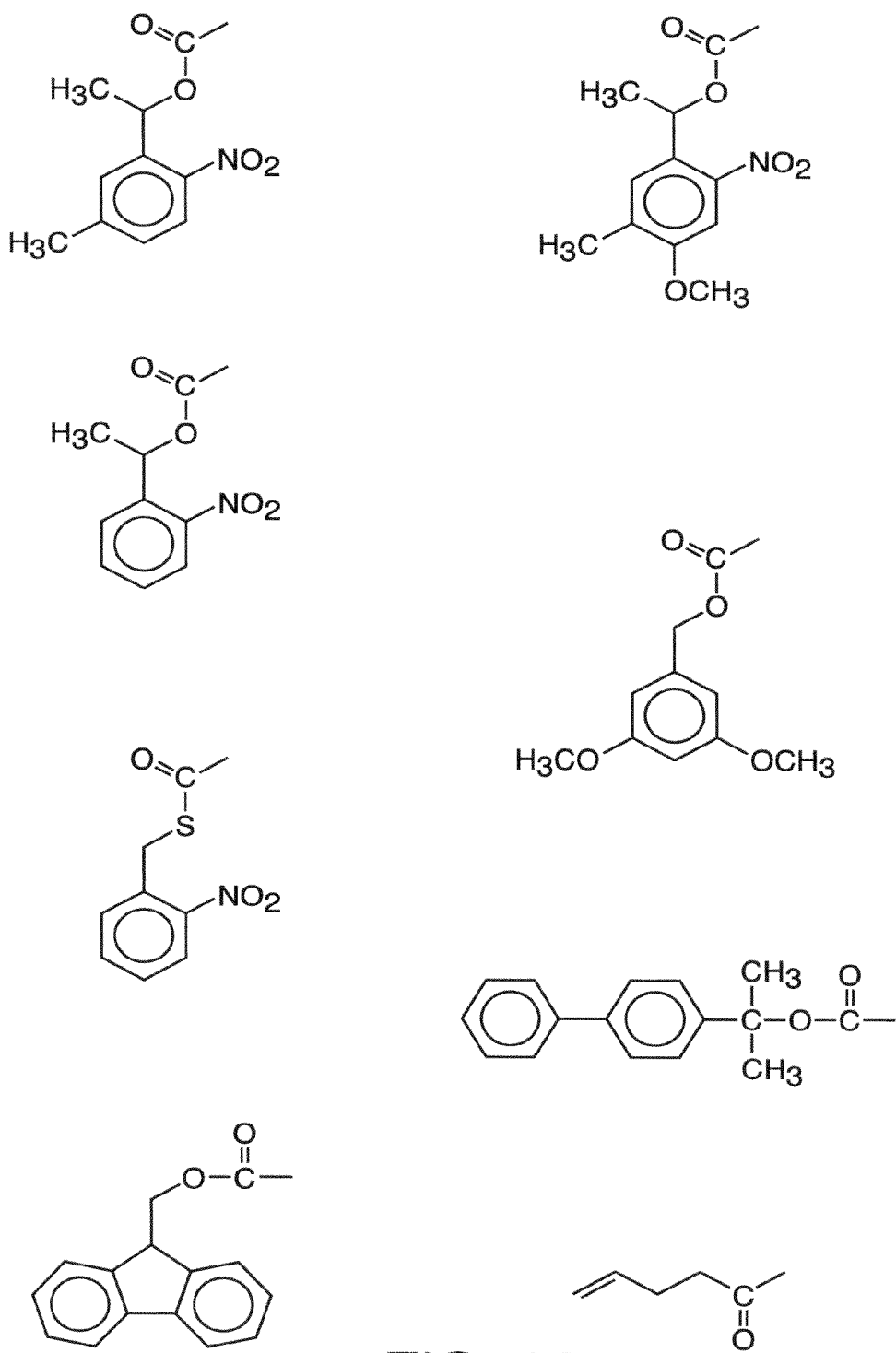
FIG. 16 shows several examples of protective groups useful in the preparation of marker-amino acid-tRNA conjugates via the protective group replacement strategy of the present invention. Photocleavable protective groups: 1-(2-nitrophenyl-5-methyl)ethyloxycarbonyl (Npe), 1-(2-nitrophenyl-4,5-dimethoxy)ethyloxycarbonyl (NVOC), 1-(2-nitrophenyl)ethyloxycarbonyl, 3,5-(dimethoxy)benzyloxycarbonyl, 2-nitrophenylsulfenyloxycarbonyl, biphenylylisopropyloxycarbonyl (Bpoc), 9-fluorenylmethyloxycarbonyl (Fmoc), pent-4-enoyl (Pent).

In another embodiment, the first chelator is incorporated into protein, the second chelator and metal ion are added, and the complex is formed. (See FIG. 11). Excess of the second chelator and metal ion are washed away and the complex is either detected by luminescence assay or a dissociation is performed by adding excess of competing chelator (such as 4,7-bis(chlorosulfophenyl)-1,10-phenantroline-2,9-dicarboxylic acid, "BCPDA") and enhancing agents (such as detergents) and luminescence is detected in solution. (See "Applications of Fluorescence in Immunoassays," by I. Hemmila, Wiley-Interscience, New York, 1991.). In another embodiment, chelators and metal ions can be introduced into the nascent proteins via the use of linkers and the formation of stable complexes such as depicted in FIGS. 14 and 15.

It is therefore desirable to devise a method that would take advantage of the available markers, but would not suffer the limitations of classical approach. One of the ways to achieve this goal, as contemplated by a preferred embodiment of the present invention, is to use an amino acid with an amino group (and any side chain reactive groups) protected (i.e. by a protective group), convert it into an active ester and prepare the aminoacyl-pdCpA conjugate. (See FIG. 5 & Example 18). In the next step, the protective group from the amino group of the amino acid is removed, under such conditions, so that the integrity of the aminoacyl-pdCpA is preserved. (See FIG. 5 & Example 18). The main problems with this approach are: 1) 2'(3')-O-aminoacyl-pdCpA is very base labile, 2) the nucleotide backbone is acid labile (depurination), and 3) the deoxycytidine moiety is sensitive to reducing conditions.

The above factors somewhat limit the choice of protective groups that can be used in this approach to, for example, the following protective groups:

1) acid labile protective groups (mild acid treatment) such as a Bpoc group;
2) base labile (under anhydrous conditions) protective groups such as Fmoc and anhydrous tetramethylguanidine;
3) photolabile groups protective groups such as NVOC (1-(2-nitrophenyl-4,5-dimethoxy)ethyloxycarbonyl) and Npe (1-(2-nitrophenyl-5-methyl)ethyloxycarbonyl);
4) protective groups that are removable by other agents such as pent-4-enoyl (Pent) and its treatment with iodine.

The present invention provides certain advantages of the methods of the prior art (e.g. U.S. Pat. Nos. 5,922,858 and 5,643,722 to Rotschild et al.). For example, as noted above, the methods of the present invention: 1) use an unprotected dinucleotide (or polynucleotide), and 2) allow for labeling of the nascent protein after the nascent protein is formed.

II. Preparation of Aminoacyl-pdCpA Conjugates and Aminoacyl-tRNAs

Figure 5:
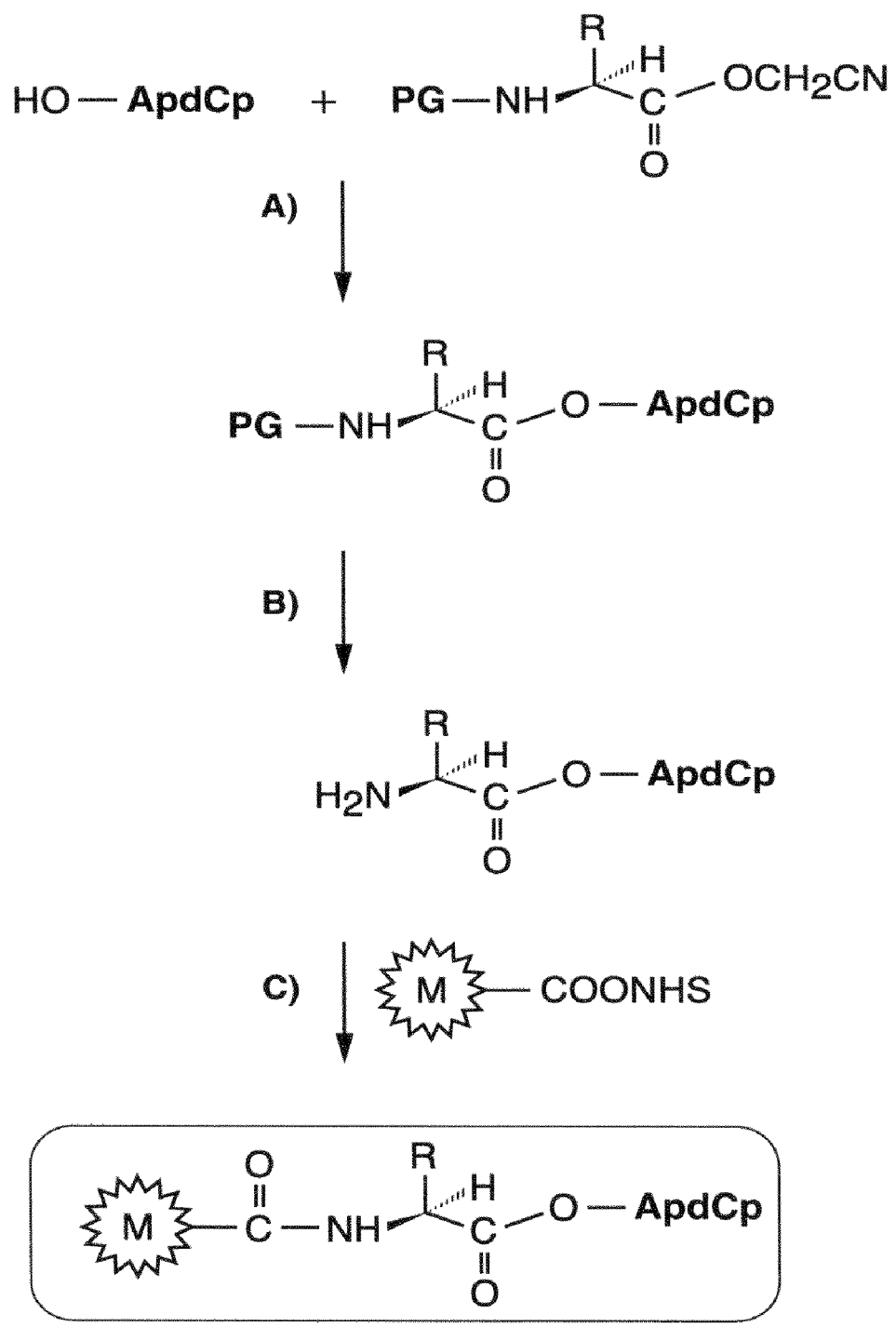
FIG. 5 shows one embodiment for the chemical aminoacylation of pdCpA dinucleotide wherein the amino acid, carrying protective group PG is converted into cyanomethyl ester and reacted with the (2') 3'-OH groups on the ribose ring of the pdCpA dinucleotide in step (a). This is followed by step (b) in which the protective group from the alpha amino group of amino acid is removed under such conditions, that the integrity of the aminoacyl-pdCpA conjugate is preserved. In the next step (c), a specific reaction between the exposed amino group on the amino acid and marker molecule (in the form of N-hydroxy succinimidyl ester (NHS)) is carried out which result in the introduction of marker molecule "M" into the aminoacyl-pdCpA conjugate. A variety of such esters are available (see Table 7).

The present invention relates to the preparation of aminoacyl-pdCpA conjugates. For example, FIG. 5 provides a detailed depiction of one embodiment of the methods of the present invention. In said embodiment, the present invention contemplates a method for the chemical aminoacylation of a pdCpA dinucleotide wherein the amino acid, carrying protective group PG is converted into cyanomethyl ester and reacted with the (2') 3'-OH groups on the ribose ring of the pdCpA dinucleotide in the first step. In the next step, the protective group from the alpha amino group of an amino acid is removed under such conditions, that the integrity of the aminoacyl-pdCpA conjugate is preserved. In the next step, a specific reaction between the exposed amino group on the amino acid and marker molecule (in the form of N-hydroxy succinimidyl ester (NHS)) is carried out which result in the introduction of marker molecule into the aminoacyl-pdCpA conjugate (forming a marker-aminoacyl-dinucleotide conjugate). Finally, said conjugate is ligated to a truncated tRNA molecule to produce a misaminoacylated tRNA that may be subjected to translation (i.e. protein synthesis) to produce a peptide comprising said marker molecule.

In another embodiment, the present invention contemplates a method for the chemical aminoacylation of a pdCpA dinucleotide wherein the amino acid, carrying a protective group ("PG") is converted into cyanomethyl ester and reacted with the (2') 3'-OH groups on the ribose ring of the pdCpA dinucleotide in the first step (forming an aminoacyl-dinucleotide conjugate). In the next step, the protective group from the alpha amino group of an amino acid is removed under such conditions, that the integrity of the aminoacyl-pdCpA conjugate is preserved. In the next step, said conjugate is ligated to a truncated tRNA molecule. Finally, a specific reaction between the exposed amino group on the amino acid and marker molecule (in the form of N-hydroxy succinimidyl ester (NHS)) is carried out which result in the introduction of marker molecule into the aminoacyl-pdCpA conjugate (forming a marker-aminoacyl-dinucleotide conjugate). As noted above, the end product is a misaminoacylated tRNA that may be subjected to translation (i.e. protein synthesis) to produce a peptide comprising said marker molecule.

Figure 6:
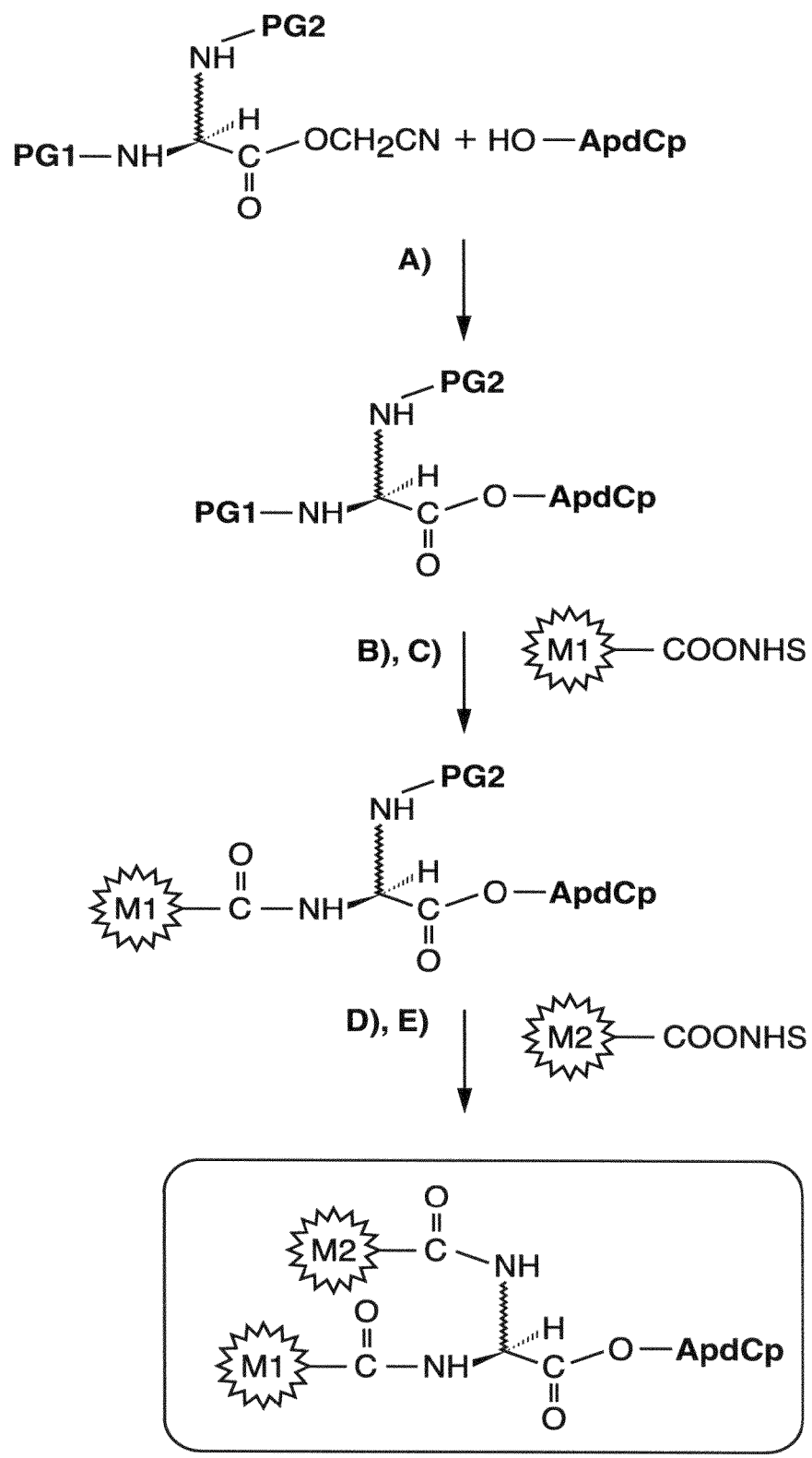
FIG. 6 shows one embodiment for the chemical aminoacylation of pdCpA dinucleotide wherein the amino acid, carrying two protective groups, PG1 and PG2, is converted into cyanomethyl ester and reacted with the (2') 3'-OH groups on the ribose ring of the pdCpA dinucleotide in step (a). This is followed by step (b) during which the protective group PG1 from the alpha amino group of amino acid is removed under conditions such that the integrity of the aminoacyl-pdCpA conjugate is preserved. This is followed by step (c) wherein a specific reaction between the exposed amino group on the amino acid and marker molecule M1 occurs. In the next steps (d & e), protective group PG2 is removed under conditions such that the integrity of the aminoacyl-pdCpA conjugate is preserved followed by a specific reaction between the exposed amino group on the amino acid and marker molecule M2 (i.e. a second marker is introduced).
Figure 7:
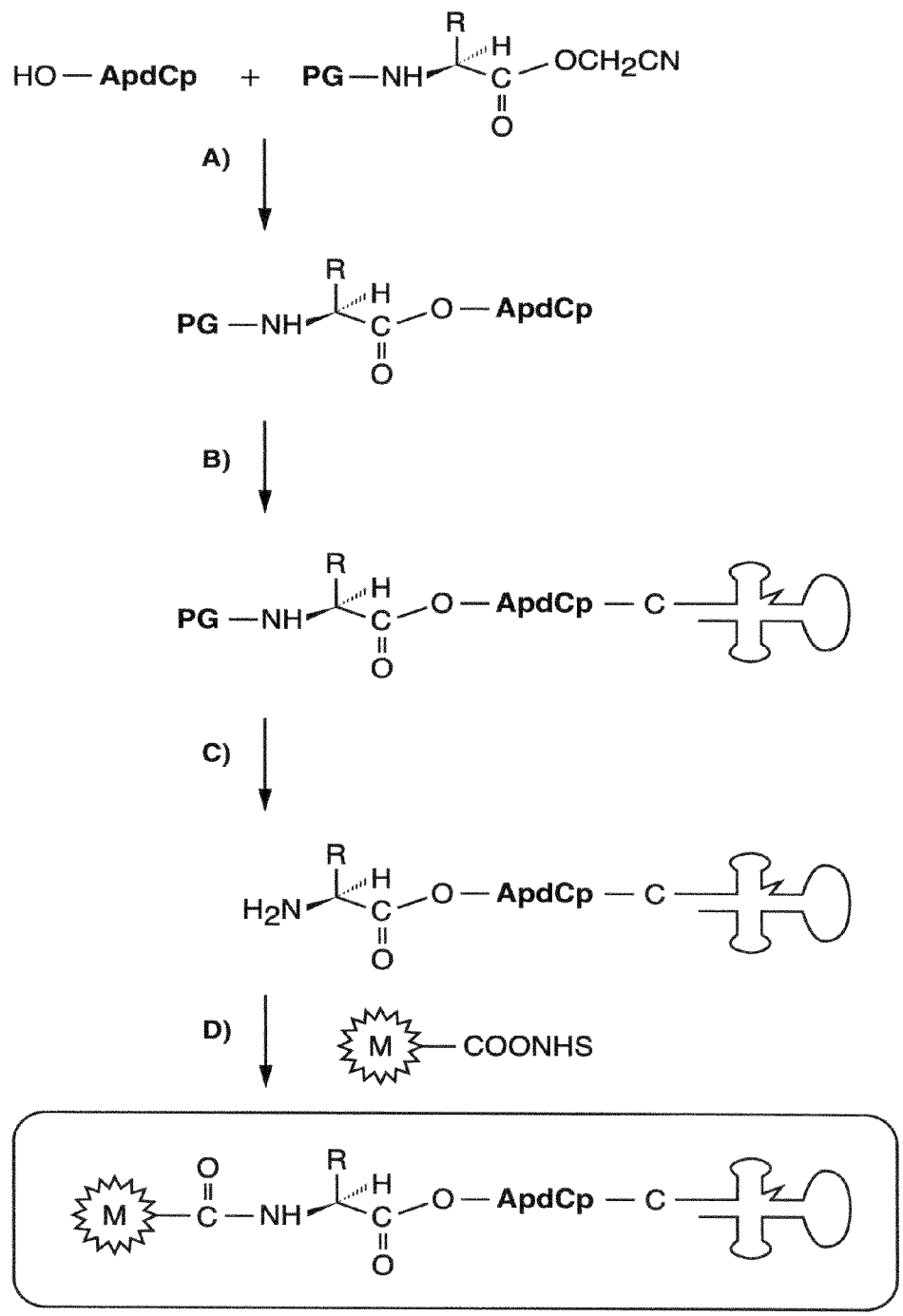
FIG. 7 shows one embodiment for the chemical aminoacylation of pdCpA dinucleotide wherein the amino acid, carrying protective group PG, is converted into cyanomethyl ester and reacted with the (2') 3'-OH groups on the ribose ring of the pdCpA dinucleotide in step (a). This is followed by step (b) in which the aminoacyl-pdCpA carrying the protective group PG is ligated to the truncated (-CA) tRNA molecule. In the next step (c), the protective group (PG) from the alpha amino group of amino acid is removed under such conditions, that the integrity of the aminoacyl-tRNA conjugate is preserved. In the next step (d) a specific reaction between the exposed amino group on the amino acid and marker molecule in the form of N-hydroxysuccinimidyl ester (NHS) is carried out which result in the introduction of marker molecule into the aminoacyl-tRNA conjugate.
Figure 8:
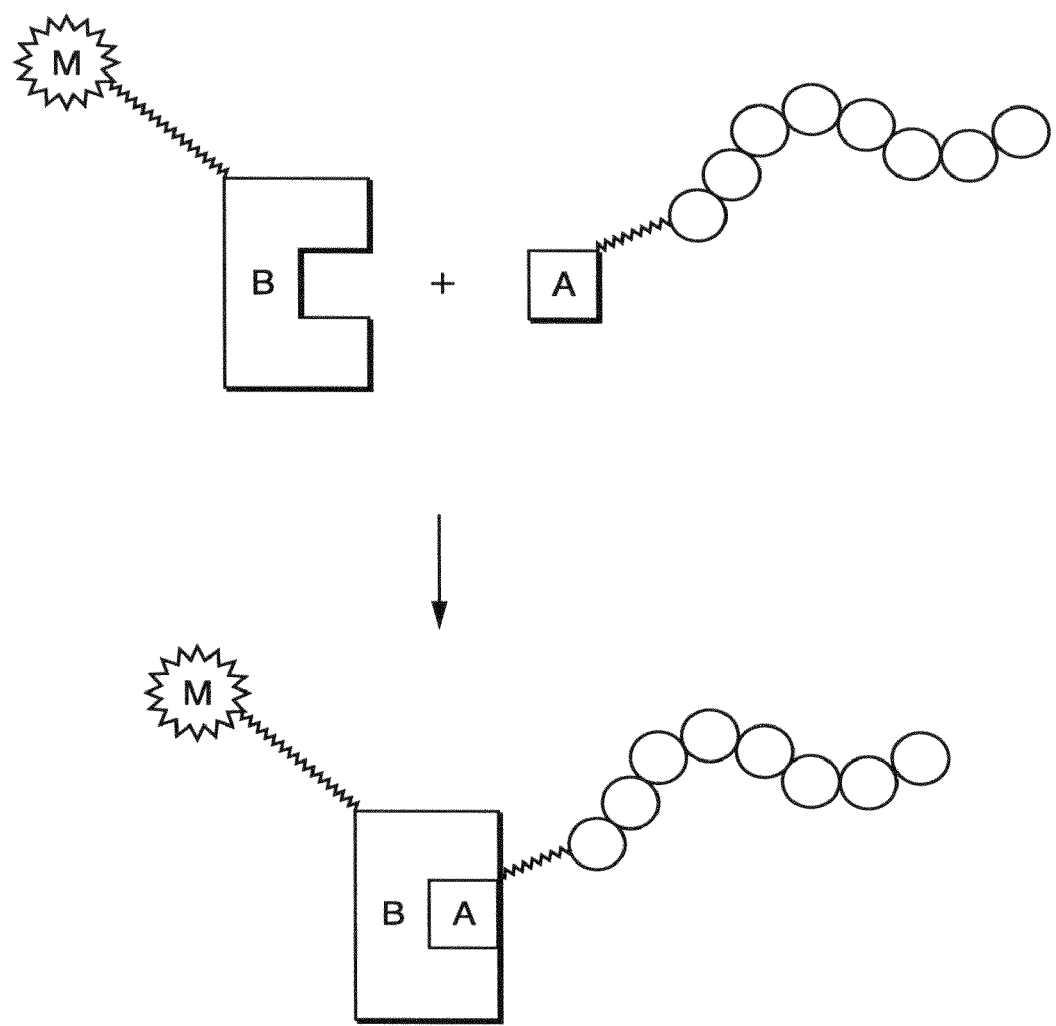
FIG. 8 shows the interaction between nascent protein modified with linker molecule A with linker molecule B conjugated to the marker molecule M. Linker A is introduced into protein molecule via the tRNA. Once protein is produced, it is incubated with the linker B-marker M conjugate which results in the formation of marker M-linker AB-protein conjugate.
Figure 9:
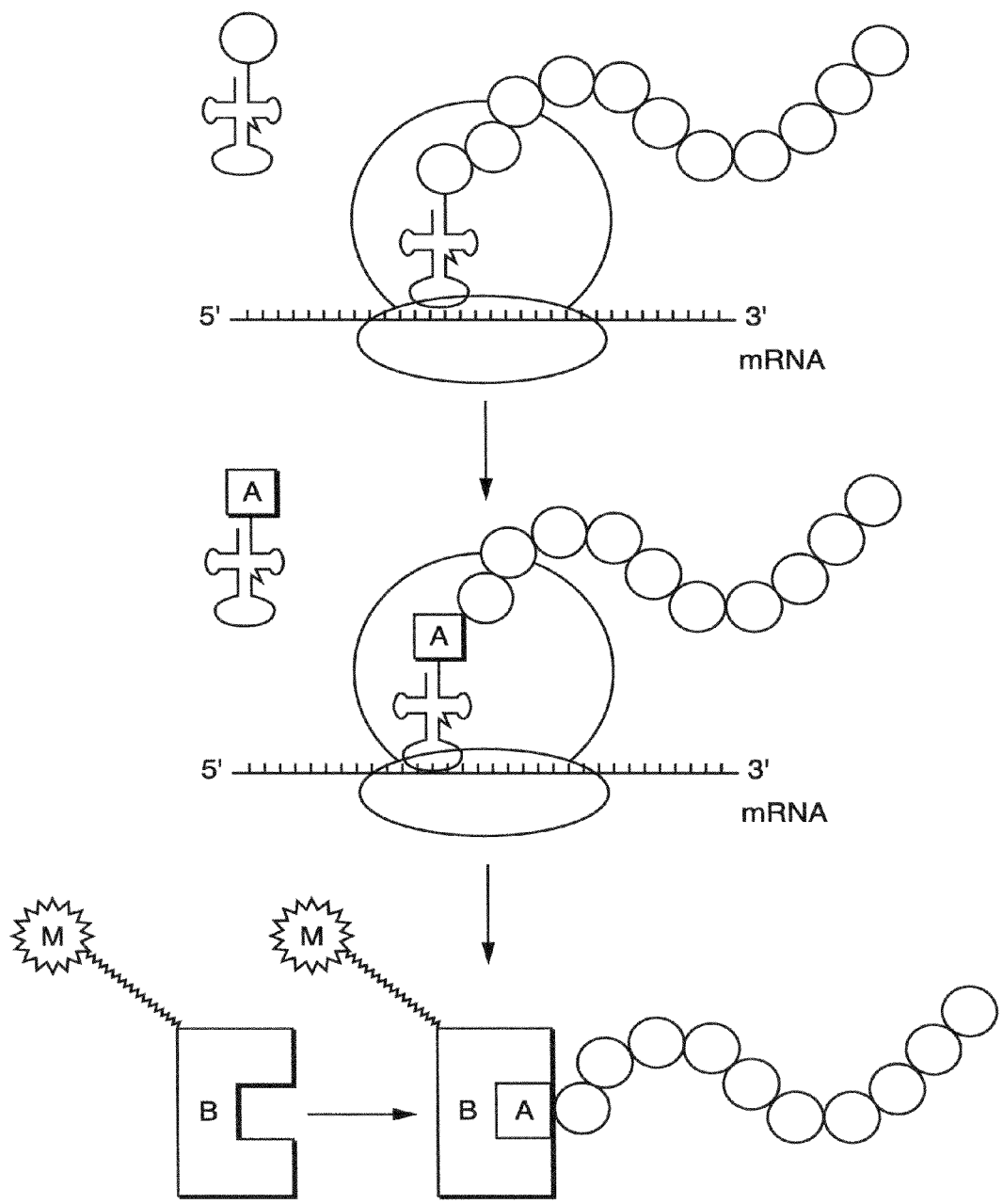
FIG. 9 shows one example of the introduction of linker A into nascent protein via the tRNA in a site-specific manner. This is followed by incubation with linker B-marker M conjugate, which due to specific interaction between linker molecules A and B, produces marker M-linker AB-protein conjugate.
Figure 10:
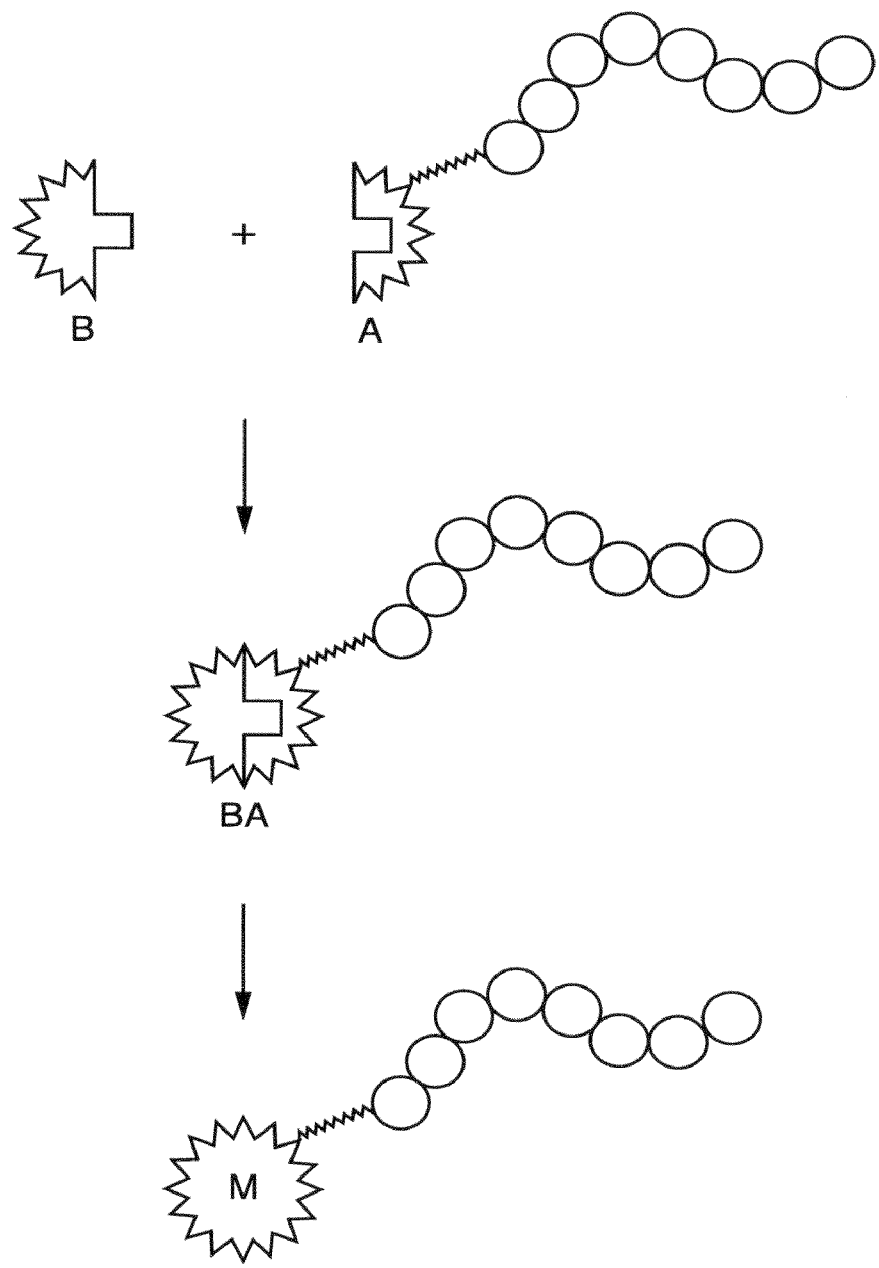
FIG. 10 shows one example of the formation of the marker molecule "M" as a result of specific interaction between linker A (on nascent protein) and linker B (free in solution).

The present invention is also directed at the preparation of aminoacyl-pdCpA conjugates and aminoacyl-tRNAs wherein the amino acid is bifunctional and carries, for example a fluorophore (detectable marker) and a second marker that can serve as an affinity purification handle. (See Part III below and FIG. 6 & Example 17). This can be achieved utilizing amino acids possessing reactive side chains (in addition to the alpha-amino group) which allow the attachment of a second marker. In some embodiments, it is desirable to remove the incorporated marker from the target protein after affinity purification. Said removal may be achieved, for example, by utilizing a photocleavable affinity tag such as photocleavable biotin (PC-biotin).

Another embodiment of this invention is directed at utilization of specific fluorescent markers for direct incorporation into proteins via aminoacyl-tRNAs. In particular, methods are described to prepare aminoacylated tRNAs carrying fluorescein and its derivatives. (See Examples 13 & 14). Markers are basically molecules which will be recognized by the enzymes of the translation process and transferred from a charged tRNA into a growing peptide chain. To be useful, markers must also possess certain physical and physiochemical properties. Therefore, there are multiple criteria which can be used to identify a useful marker. First, a marker must be suitable for incorporation into a growing peptide chain. This may be determined by the presence of chemical groups which will participate in peptide bond formation. Second, markers should be attachable to a tRNA molecule. Attachment is a covalent interaction between the 3'-terminus of the tRNA molecule and the carboxy group of the marker or a linking group attached to the marker and to a truncated tRNA molecule. Linking groups may be nucleotides, short oligonucleotides or other similar molecules and are preferably dinucleotides and more preferably the dinucleotide CA. Third, markers should have one or more physical properties that facilitate detection and possibly isolation of nascent proteins. Useful physical properties include a characteristic electromagnetic spectral property such as emission or absorbance, magnetism, electron spin resonance, electrical capacitance, dielectric constant or electrical conductivity.

Useful markers include (but are not limited to) native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent or chromatic. Fluorescent moieties which are useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., *BioTechniques,* 15: 152-59 (1993)). These markers are detectable at the femtomolar ranges and below.

In addition to fluorescent markers, a variety of other markers possessing specific physical properties can be used to detect nascent protein production. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity and nuclear magnetic resonances. These electromagnetic spectroscopic properties are preferably not possessed by native amino acids or are readily distinguishable from the properties of native amino acids. For example, the amino acid tryptophan absorbs near 290 nm, and has fluorescent emission near 340 nm when excited with light near 290 nm. Thus, tryptophan analogs with absorption and/or fluorescence properties that are sufficiently different from tryptophan can be used to facilitate their detection in proteins.

Many different modified amino acids which can be used as markers are commercially available (Sigma Chemical; St. Louis, Mo.; Molecular Probes; Eugene, Oreg.). One such marker is N-epsilon-dansyllysine. Another such marker is a fluorescent amino acid analog based on the highly fluorescent molecule coumarin. This fluorophore has a much higher fluorescence quantum yield than dansyl chloride and can facilitate detection of much lower levels of nascent protein. In addition, this coumarin derivative has a structure similar to the native amino acid tryptophan. These structural similarities are useful where maintenance of the nascent proteins' native structure or function are important or desired. Coumarin is synthesized by the alkylation of acetamidomalonate with a slight excess of 4-bromomethyl coumarin (Aldrich Chemicals; Milwaukee; Wis.) in the presence of sodium ethoxide, followed by acid hydrolysis. The corresponding amino acid as a hydrochloride salt that can be converted to the free amino acid analog.

The coumarin derivative can be used most advantageously if it misaminoacylates the tryptophan-tRNA, either enzymatically or chemically. When introduced in the form of the misaminoacylated tryptophan-tRNA, the coumarin amino acid will be incorporated only into tryptophan positions. By controlling the concentration of misaminoacylated tRNAs or free coumarin derivatives in the cell-free synthesis system, the number of coumarin amino acids incorporated into the nascent protein can also be controlled. This procedure can be utilized to control the amount of most any markers in nascent proteins.

Markers can be chemically synthesized from a native amino acid and a molecule with marker properties which cannot normally function as an amino acid. For example a highly fluorescent molecule can be chemically linked to a native amino acid group. The chemical modification occurs on the amino acid side-chain, leaving the carboxyl and amino functionalities free to participate in a polypeptide bond formation. Highly fluorescent dansyl chloride can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing the normal incorporation of dansyllysine into a protein.

A marker can also be modified after the tRNA molecule is aminoacylated or misaminoacylated using chemical reactions which specifically modify the marker without significantly altering the functional activity of the aminoacylated tRNA. These types of post-aminoacylation modifications may facilitate detection, isolation or purification, and can sometimes be used where the modification allow the nascent protein to attain a native or more functional configuration.

Fluorescent and other markers which have detectable electromagnetic spectral properties that can be detected by spectrometers and distinguished from the electromagnetic spectral properties on native amino acids. Spectrometers which are most useful include fluorescence, Raman, absorption, electron spin resonance, visible, infrared and ultraviolet spectrometers. Other markers, such as markers with distinct electrical properties can be detected by an apparatus such as an ammeter, voltmeter or other spectrometer. Physical properties of markers which relate to the distinctive interaction of the marker with an electromagnetic field is readily detectable using instruments such as fluorescence, Raman, absorption, electron spin resonance spectrometers. Markers may also undergo a chemical, biochemical, electrochemical or photochemical reaction such as a color change in response to external forces or agents such as an electromagnetic field or reactant molecules which allows its detection.

Another embodiment of the present invention is directed specifically at lysine and its analogs modified at single or both amino groups. (See FIG. 20 and Examples 7-12). Incorporation of dual marker at the N-terminus of proteins can be achieved with these amino acids. The preparation of these conjugates by using the protective group replacement strategy is more complex, since the two amino groups need to be differentially protected, these protective groups should be orthogonal, finally deprotection process should preserve the integrity of the aminoacyl-bond as well as nucleic acid bases and backbone.

Another embodiment of this invention is directed at the preparation of aminoacyl-tRNAs lacking amino acid specificity. This is very useful for introduction of fluorophores (i.e. markers) when the goal is to achieve trace labeling and visualize translation products on a gel (e.g. agarose or polyacrylamide) by fluorescent scanning. In this case the incorporation of the label is independent of the amino acid composition of the translation product. The preparation of this tRNA is achieved by utilizing crude mixture of tRNAs, that have not been separated with the regard to amino acid acceptor activity. The whole mixture is initially processed to remove the last two nucleotides from the 3'-terminus (i.e. such that the tRNA is truncated) and ligated to an aminoacyl-pdCpA molecule carrying the fluorophore. In one embodiment, said aminoacyl-tRNAs lacking amino acid specificity comprise diaminopropionic acid ("Dpr-COOH") derivatives as described in Example 16. In one embodiment said aminoacyl-tRNAs lacking amino acid specificity comprising diamino propionic acid derivatives are prepared as described in Examples 19-21.

III. Translation and Detection of Aminoacylated tRNAs

A. Protein Synthesis to Incorporate Marker-Aminoacyl-Polynucleotide Conjugates

The aminoacylated tRNAs (i.e. marker-aminoacyl-dinucleotide conjugates) produced by the methods of the present invention may be incorporated or translated into protein. For example, according to the method described in U.S. Pat. Nos. 5,922,858 and 5,643,722 to Rotschild et al. (hereby incorporated by reference), misaminoacylated tRNAs may be introduced into a cellular or cell-free protein synthesis system (i.e. the translation system), where they function in protein synthesis to incorporate detectable marker in place of a native amino acid in the growing peptide chain. Such a translation system comprises macromolecules including RNA and enzymes, translation, initiation and elongation factors, and chemical reagents. RNA of the system is required in three molecular forms, ribosomal RNA (rRNA), messenger RNA (mRNA) and transfer RNA (tRNA). mRNA carries the genetic instructions for building a peptide encoded within its codon sequence. tRNAs contain specific anti-codons which decode the mRNA and individually carry amino acids into position along the growing peptide chain. Ribosomes, complexes of rRNA and protein, provide a dynamic structural framework on which the translation process, including translocation, can proceed. Within the cell, individualized aminoacyl tRNA synthetases bind specific amino acids to tRNA molecules carrying the matching anti-codon creating aminoacylated or charged tRNAs by the process of aminoacylation. The process of translation including the aminoacylation or charging of a tRNA molecule is described in "Molecular Cell Biology" (Darnell et al. Editors, Scientific American Books, N.Y., N.Y. (1991)), which is hereby specifically incorporated by reference. Aminoacylation may be natural or by artificial means utilizing native amino acids, non-native amino acid, amino acid analogs or derivatives, or other molecules such as detectable chemicals or coupling agents. The resulting misaminoacylated tRNA comprises a native amino acid coupled with a chemical moiety, non-native amino acid, amino acid derivative or analog, or other detectable chemicals. These misaminoacylated tRNAs incorporate their markers into the growing peptide chain during translation forming labeled nascent proteins which can be detected and isolated by the presence or absence of the marker.

Any proteins that can be expressed by translation in a cellular or cell-free translation system may be nascent proteins and consequently, labeled, detected and isolated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known. Examples of cell-free systems include prokaryotic lysates such as $Escherichia$ $coli$ lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1, IF-2, IF-3 (alpha or beta)), elongation factor T (EF-Tu), or termination factors.

Cell-free systems may also be coupled transcription/translation systems wherein DNA is introduced to the system, transcribed into mRNA and the mRNA translated as described in "Current Protocols in Molecular Biology" (Ausubel et al., Editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), are not required.

Site-directed incorporation of the non-native analogs into the protein during translation is also not required. Incorporation of markers can occur anywhere in the polypeptide and can also occur at multiple locations. This eliminates the need for prior information about the genetic sequence of the translated mRNA or the need for modifying this genetic sequence.

In some cases, it may be desirable to preserve the functional properties of the nascent protein. A subset of tRNAs which will incorporate markers at sites which do not interfere with protein function or structure can be chosen. Amino acids at the amino or carboxyl terminus of a polypeptide do not alter significantly the function or structure. tRNA molecules which recognize the universal codon for the initiation of protein translation (AUG), when misaminoacylated with marker, will place marker at the amino terminus. Prokaryotic protein synthesizing systems utilize initiator $tRNA^{fMet}$ molecules and eukaryotic systems initiator $tRNA^{Met}$ molecules. In either system, the initiator tRNA molecules are aminoacylated with markers which may be non-native amino acids or amino acid analogs or derivatives that possess marker, reporter or affinity properties. The resulting nascent proteins will be exclusively labeled at their amino terminus, although markers placed internally do not necessarily destroy structural or functional aspects of a protein. For example, a tRNA$^{Lys}$, may be misaminoacylated with the amino acid derivative dansyllysine which does not interfere with protein function or structure. In addition, using limiting amounts of misaminoacylated tRNAs, it is possible to detect and isolate nascent proteins having only a very small fraction labeled with marker which can be very useful for isolating proteins when the effects of large quantities of marker would be detrimental or are unknown.

It is not intended that the tRNA be limited to a single misaminoacylated tRNA (i.e., for example, lysine). The present invention contemplates the misaminoacylation of all amino acid tRNA's with a marker (i.e., the "total tRNA" embodiment or tRNA$^{TOTAL}$). This approach uniformly labels any length of any nascent protein with the affinity marker. Importantly, even if an amino acid in the C-terminal or N-terminal epitope receives a marker, the expected 1% incorporation rate (i.e., due to a low misaminoacylated tRNA concentration) will not reduce the ability to detect the affected epitope.

Misaminoacylated tRNAs are introduced into the cellular- or cell-free protein synthesis system. In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, E. coli (S-30), red blood cells (reticulocyte lysate), and oocytes. Once created, said reaction mixtures can be stored as aliquots at about +4° C. to −70° C. The method of preparing such reaction mixtures is described by J. M. Pratt ("Transcription and Translation," B. D. Hames and S. J. Higgins, Editors, p. 209, IRL Press, Oxford (1984)) which is hereby incorporated by reference.

The misaminoacylated tRNA is added directly to the reaction mixture as a solution of predetermined volume and concentration. This can be done directly prior to storing the reaction mixture at −70° C. in which case the entire mixture is thawed prior to initiation of protein synthesis or prior to the initiation of protein synthesis. Efficient incorporation of markers into nascent proteins is sensitive to the final pH and magnesium ion concentration. Reaction mixtures are normally about pH 6.8 and contain a magnesium ion concentration of about 3 mM. These conditions impart stability to the base-labile aminoacyl linkage of the misaminoacylated tRNA. Aminoacylated tRNAs are available in sufficient quantities from the translation extract. Misaminoacylated tRNAs charged with markers are added at between about 1.0 µg/ml to about 1.0 mg/ml, preferably at between about 10 µg/ml to about 500 µg/ml, and more preferably at about 150 µg/ml.

Initiation of protein synthesis occurs upon addition of a quantity of mRNA or DNA to the reaction mixture containing the misaminoacylated tRNAs. mRNA molecules may be prepared or obtained from recombinant sources, or purified from other cells by procedure such as poly-dT chromatography. One method of assuring that the proper ratio of the reaction mixture components is to use predetermined volumes that are stored in convenient containers such as vials or standard microcentrifuge tubes. For example, DNA and/or mRNA coding for the nascent proteins and the misaminoacylated tRNA solution are premixed in proper amounts and stored separately in tubes. Tubes are mixed when needed to initiate protein synthesis.

Translations in cell-free systems generally require incubation of the ingredients for a period of time. Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (Spirin et al., Science, 242: 1162-64 (1988)). This process may be desirable for large scale production of nascent proteins. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C., and even more preferably at about 25° C. or about 37° C. Certain markers may be sensitive to temperature fluctuations and in such cases, it is preferable to conduct those incubations in the non-sensitive ranges. Translation mixes will typically comprise buffers such as Tris-HCl, HEPES or another suitable buffering agent to maintain the pH of the solution between about 6.0 to 8.0, and preferably at about 7.0. Again, certain markers may be pH sensitive and in such cases, it is preferable to conduct incubations outside of the sensitive ranges for the marker. Translation efficiency may not be optimal, but marker utility will be enhanced. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

In cellular protein synthesis, it is necessary to introduce misaminoacylated tRNAs or markers into intact cells, cell organelles, cell envelopes and other discrete volumes bounded by an intact biological membrane, which contain a protein synthesizing system. This can be accomplished through a variety of methods that have been previously established such as sealing the tRNA solution into liposomes or vesicles which have the characteristic that they can be induced to fuse with cells. Fusion introduces the liposome or vesicle interior solution containing the tRNA into the cell. Alternatively, some cells will actively incorporate liposomes into their interior cytoplasm through phagocytosis. The tRNA solution could also be introduced through the process of cationic detergent mediated lipofection (Felgner et al., Proc. Natl. Acad. Sci. USA, 84: 7413-17 (1987)), or injected into large cells such as oocytes. Injection may be through direct perfusion with micropipettes or through the method of electroporation.

Alternatively, cells can be permeabilized by incubation for a short period of time in a solution containing low concentrations of detergents in a hypotonic media. Useful detergents include Nonidet-P 40 (NP-40), Triton X-100 (TX-100) or deoxycholate at concentrations of about 0.01 nM to 1.0 mM, preferably between about 0.1 µM to about 0.01 mM, and more preferably about 1 µM. Permeabilized cells allow marker to pass through cellular membranes unaltered and be incorporated into nascent proteins by host cell enzymes. Such systems can be formed from intact cells in culture such as bacterial cells, primary cells, immortalized cell lines, human cells or mixed cell populations. These cells may, for example, be transfected with an appropriate vector containing the gene of interest, under the control of a strong and possibly regulated promoter. Messages are expressed from these vectors and subsequently translated within cells. Intact misaminoacylated tRNA molecules, already charged with a non-radioactive marker could be introduced to cells and incorporated into translated product.

One example of the use of misaminoacylation to detect nascent protein is as follows. A tRNA molecule is misaminoacylated with the marker which is highly fluorescent when excited with UV (ultraviolet) radiation. The misaminoacylated tRNA is then introduced into a cell-free protein synthesis extract and the nascent proteins containing the marker analog produced. Proteins in the cell-free extract are separated by polyacrylamide gel electrophoresis (PAGE). The resulting gel contains bands which correspond to all of the proteins present in the cell-free extract. The nascent protein is identified upon UV illumination of the gel by detection of fluorescence from the band corresponding to proteins containing marker. Detection can be through visual observation or by other conventional means of fluorescence detection.

B. Detection and Purification Methods

Normally detection first involves physical separation of the nascent proteins from other biomolecules present in the cellular or cell-free protein synthesis system. Protein separation can be performed using, for example, gel electrophoresis or column chromatography and can be further facilitated with affinity markers which uniquely bind acceptor groups. Detection of a marker containing a fluorophore by gel electrophoresis can be accomplished using conventional fluorescence detection methods.

For example, after protein synthesis in a cell-free system, the reaction mixture, which contains all of the biomolecules necessary for protein synthesis as well as nascent proteins, is loaded onto a gel which may be composed of polyacrylamide or agarose (R. C. Allen et al., "Gel Electrophoresis and Isoelectric Focusing of Proteins," Walter de Gruyter, New York, N.Y. (1984)). This mixture also contains the misaminoacylated tRNAs bearing the marker as well as uncharged tRNAs. Subsequent to loading the reaction mixture, a voltage is applied which spatially separates the proteins on the gel in the direction of the applied electric field. The proteins separate and appear as a set of discrete or overlapping bands which can be visualized using a pre- or post-gel staining technique such as Coomasie blue staining. The migration of the protein band on the gel is a function of the molecular weight of the protein with increasing distance from the loading position being a function of decreasing molecular weight. Bands on the gel which contain nascent proteins will exhibit fluorescence when excited at a suitable wavelength. These bands can be detected visually (i.e. photographically or spectroscopically) and, if desired, the nascent proteins purified from gel sections.

For example, if using dansyllysine as a marker, nascent proteins will fluoresce at 470 nm when excited by UV illumination. This fluorescence can be detected visually by simply using a standard hand-held UV illuminator or a transilluminator. Approximately 10 nanograms (ng) of the protein bacteriorhodopsin is detectable using this method. Also useful are electronic imaging devices (e.g. FluorImager or a fluorescence plate reader) which can rapidly screen and identify very low concentrations of markers. When using fluorescein-based marker (e.g. 5-FAM, 6-FAM, and EX-5) or BODIPY-FL, nascent proteins will fluoresce upon excitation in the UV range (300-365 nm). The detection can be achieved by the use of a transilluminator and a CCD camera. In addition, fluorescein and BODIPY-FL labeled proteins can be detected using the 488 nm line of the argon laser used by FluorImager (Molecular Dynamics) or a fluorescent plate reader.

The molecular weight and quantity of the nascent protein can be determined by comparison of its band-position on the gel with a set of bands of proteins of predetermined molecular weight. For example, a nascent protein of molecular weight 25,000 could be determined because of its relative position on the gel relative to a calibration gel containing the commercially available standard marker proteins of known quantities and with known molecular weights (bovine serum albumin, 66 kD; porcine heart fumarase, 48.5 kD; carbonic anhydrase, 29 kD; β-lactoglobulin, 18.4 kD; α-lactoglobulin, 14.2 kD; Sigma Chemical; St. Louis, Mo.).

Calibration proteins may also contain a similar markers for convenient detection using the same method as the gel bearing the nascent protein. This can be accomplished in many cases by directly reacting the calibration proteins with a molecule similar to the marker. For example, the calibration proteins can be modified with dansyl chloride so as to obtain their fluorescent derivatives (R. E. Stephens, *Anal. Biochem.* 65: 369-79 (1975)). These fluorescent proteins can be analyzed using PAGE. Combined detection of these fluorescent calibration proteins along with that of nascent protein which contains fluorescent marker analog will accurately determine both the molecular weight and quantity of the nascent protein synthesized. If necessary, the amounts of marker within each calibration and nascent protein can be determined to provide an accurate quantitation.

Other methods of protein separation are also useful for detection and subsequent isolation and purification of nascent proteins containing markers. For example, proteins can be separated using capillary electrophoresis, isoelectric focusing, low pressure chromatography and high-performance, or fast-pressure, liquid chromatography (HPLC or FPLC). In these cases, the individual proteins are separated into fractions which can be individually analyzed by fluorescent detectors at the emission wavelengths of the markers. Alternatively, on-line fluorescence detection can be used to detect nascent proteins as they emerge from the column fractionation system. A graph of fluorescence as a function of retention time provides information on both the quantity and purity of nascent proteins produced.

Another embodiment of the invention is directed to a method for labeling, detecting and, if desired, isolating and purifying nascent proteins, as described above, containing cleavable markers. Cleavable markers comprise a chemical structure which is sensitive to external effects such as physical or enzymatic treatments, chemical or thermal treatments, electromagnetic radiation such as gamma rays, x-rays, ultraviolet light, visible light, infrared light, microwaves, radio waves or electric fields. The marker is aminoacylated to tRNA molecules as before using conventional technology or misaminoacylated and added to a translation system. After incubation and production of nascent proteins, marker can be cleaved by the application of specified treatments and nascent proteins detected. Alternatively, nascent proteins may also be detected and isolated by the presence or absence of the cleaved marker or the chemical moiety removed from the marker.

In addition to antibodies, other biological molecules exist which exhibit equally strong interaction with target molecules or chemical moieties. An example is the interaction of biotin and avidin. In this case, an affinity analog which contains the biotin moiety would be incorporated into the protein using the methods which are part of the present invention. Biotin-lysine amino acid analogs are commercially available (Molecular Probes; Eugene, Oreg.).

Many devices designed to detect proteins are based on the interaction of a target protein with specific immobilized acceptor molecule. Such devices can also be used to detect nascent proteins once they contain affinity markers such as biodetectors based on sensing changes in surface plasmons, light scattering and electronic properties of materials that are altered due to the interaction of the target molecule with the immobilized acceptor group.

Nascent proteins, including those which do not contain affinity-type markers, may be isolated by more conventional isolation techniques. Some of the more useful isolation techniques which can be applied or combined to isolate and purify nascent proteins include chemical extraction, such as phenol or chloroform extract, dialysis, precipitation such as ammonium sulfate cuts, electrophoresis, and chromatographic techniques. Chemical isolation techniques generally do not provide specific isolation of individual proteins, but are useful for removal of bulk quantities of non-proteinaceous material. Electrophoretic separation involves placing the translation mixture containing nascent proteins into wells of a gel which may be a denaturing or non-denaturing polyacrylamide or agarose gel. Direct or pulsed current is applied to the gel and the various components of the system separate according to molecular size, configuration, charge or a combination of their physical properties. Once distinguished on the gel, the portion containing the isolated proteins removed and the nascent proteins purified from the gel. Methods for the purification of protein from acrylamide and agarose gels are known and commercially available.

Chromatographic techniques which are useful for the isolation and purification of proteins include gel filtration, fast-pressure or high-pressure liquid chromatography, reverse-phase chromatography, affinity chromatography and ion exchange chromatography. These techniques are very useful for isolation and purification of proteins species containing selected markers.

Another embodiment of the invention is directed to the use of markers that facilitate the detection or separation of nascent proteins produced in a cellular or cell-free protein synthesis system. Such markers are termed "affinity markers" and have the property that they selectively interact with molecules and/or materials containing acceptor groups. The affinity markers are linked by aminoacylation to tRNA molecules in an identical manner as other markers of non-native amino acid analogs and derivatives and reporter-type markers as described. These affinity markers are incorporated into nascent proteins once the misaminoacylated tRNAs are introduced into a translation system. Examples of affinity markers contemplated by the present invention may be found in U.S. Pat. Nos. 5,922,858 and 5,643,722 to Rotschild et al. (hereby incorporated by reference).

An affinity marker facilities the separation of nascent proteins because of its selective interaction with other molecules which may be biological or non-biological in origin through a coupling agent. For example, the specific molecule to which the affinity marker interacts, referred to as the "acceptor molecule," could be a small organic molecule or chemical group such as a sulphydryl group (—SH) or a large biomolecule such as an antibody. The binding is normally chemical in nature and may involve the formation of covalent or non-covalent bonds or interactions such as ionic or hydrogen bonding. The binding molecule or moiety might be free in solution or itself bound to a surface, a polymer matrix, or a reside on the surface of a substrate. The interaction may also be triggered by an external agent such as light, temperature, pressure or the addition of a chemical or biological molecule which acts as a catalyst.

The detection and/or separation of the nascent protein and other pre-existing proteins in the reaction mixture occurs because of the interaction, normally a type of binding, between the affinity marker and the acceptor molecule. Although, in some cases some incorporated affinity marker will be buried inside the interior of the nascent protein, the interaction between the affinity marker and the acceptor molecule will still occur as long as some affinity markers are exposed on the surface of the nascent protein. This is not normally a problem because the affinity marker is distributed over several locations in the protein sequence.

Affinity markers include native amino acids, non-native amino acids, amino acid derivatives or amino acid analogs in which a coupling agent is attached or incorporated. Attachment of the coupling agent to, for example, a non-native amino acid may occur through covalent interactions, although non-covalent interactions such as hydrophilic or hydrophobic interactions, hydrogen bonds, electrostatic interactions or a combination of these forces are also possible. Examples of useful coupling agents include molecules such as haptens, immunogenic molecules, biotin and biotin derivatives, and fragments and combinations of these molecules. Coupling agents enable the selective binding or attachment of newly formed nascent proteins to facilitate their detection or isolation. Coupling agents may contain antigenic sites for a specific antibody, or comprise molecules such as biotin which is known to have strong binding to acceptor groups such as streptavidin. For example, biotin may be covalently linked to an amino acid which is incorporated into a protein chain. The presence of the biotin will selectively bind only nascent proteins which incorporated such markers to avidin molecules coated onto a surface. Suitable surfaces include resins for chromatographic separation, plastics such as tissue culture surfaces for binding plates, microtiter dishes and beads, ceramics and glasses, particles including magnetic particles, polymers and other matrices. The treated surface is washed with, for example, phosphate buffered saline (PBS), to remove non-nascent proteins and other translation reagents and the nascent proteins isolated. In some case these materials may be part of biomolecular sensing devices such as optical fibers, chemfets, and plasmon detectors.

Affinity markers can also comprise cleavable markers incorporating a coupling agent. This property is important in cases where removal of the coupled agent is required to preserve the native structure and function of the protein and to release nascent protein from acceptor groups. In some cases, cleavage and removal of the coupling agent results in production of a native amino acid. One such example is photocleavable biotin coupled to an amino acid.

Figure 13:
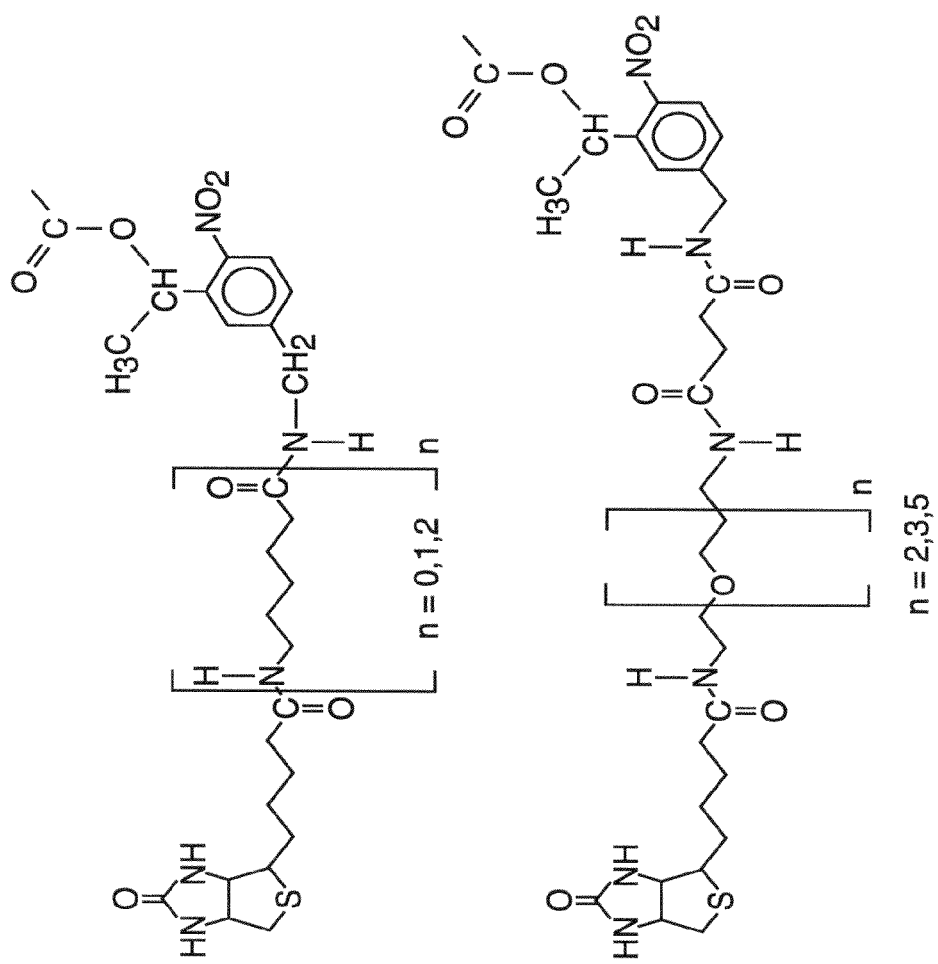
FIG. 13 shows several examples of markers comprising photocleavable biotin.

Photocleavable biotin ("PCB") contains a photoreactive moiety which comprises a phenyl ring derivatized with functional groups as represented in FIG. 13. One of such groups allows the linkage of the cross-linker moiety to the photoreactive moiety. The photoreactive moiety has the property that upon illumination, it undergoes a photoreaction that results in cleavage of the PCB molecule from the substrate.

In one embodiment, a lysine-tRNA is misaminoacylated with a marker-aminoacyl-dinucleotide conjugate comprising photocleavable biotin. The misaminoacylated tRNA is introduced into a cell-free protein synthesizing system and nascent proteins produced. The nascent proteins can be separated from other components of the system by streptavidin-coated magnetic beads using conventional methods which rely on the interaction of beads with a magnetic field. Nascent proteins are released then from beads by irradiation with UV light of approximately 280 nm wavelength.

IV. Proteome Microarray Applications Using Misaminoacylated tRNAs

As noted above, the present invention contemplates the incorporation of detectable markers, fluorophores and affinity linkers into nascent proteins by the production of chemically misaminoacylated tRNAs by protective group replacement. The present invention also contemplates the post-labelling attachment of affinity linkers and binding partners to surfaces (e.g. a microarray or microtiter plate) for the purpose of detection and purification of nascent proteins produced by chemical misaminoacylation (as described herein).

A. Custom Affinity Linkers and their Incorporation into Nascent Proteins

The present invention contemplates a variety of specially designed affinity linkers and complementary binding molecules for the ability to attach proteins to chip surfaces, removal of non-specific binders, and the stability of array including preserving functionality of array elements. In some cases, it will be highly desirable to be able to remove proteins at specific spots attached to a surface (e.g. a microarray chip) in order to perform quality control, to perform off-chip analysis of interacting proteins or for photolithographic patterning of the array. One class of compounds for this purpose are photocleavable biotins (PC-Biotins). PC-Biotin-NHS esters (FIG. 13) consist of a biotinyl moiety linked through a variable spacer arm (e.g. 5-aminocaproic acid) to an α-substituted 2-nitrobenzyl nucleus bearing an N-hydroxysuccinimidyl reactive group (NHS-carbonate). A second version of a biotin linker incorporates a non-photocleavable fluorescent label. This linker, termed double tag (FIG. 6), provides a means to detect a protein on the array surface as well as before and after photocleavage from the array. Finally, a new class of linkers based on PDBA-SHA binding pair (or partner) interactions as described below has also shown to be useful. (See FIGS. 14 & 15).

Site-Specific Incorporation of Affinity Linkers

In many cases, it is highly desirable to attach the affinity linker at a specific location in the protein. For this purpose, the present invention contemplates an approach known as N-terminal tagging. Such tags, which incorporate only at the N-terminal end of a protein, are advantageous because they have a higher probability of binding to an affinity medium (e.g. biotin to streptavidin) compared to labeling of random internal lysines. N-terminal tags also better ensure that the labeled protein remains functional compared to internal labels. Lastly, as opposed to lysine labeling for example, N-terminal labels do not depend on the amino acid composition of a protein, thereby eliminating protein to protein variation and providing quantitative label incorporation.

In an initial demonstration of this approach, a variety of biotin based affinity linkers were incorporated at either random lysines positions or selectively at the N-terminus of a set of proteins expressed in vitro which were then arrayed on NeutrAvidin-coated glass slides. The proteins were labeled using tRNAs prepared as described in the caption of FIG. 6. Conditions are designed to optimize the selective binding and removal of non-specific proteins present in the cell-free extract from the surface. Potential interference with binding can occur from endogenous biotinylated proteins in the extract and from competition with residual misaminoacylated tRNA containing biotin. Procedures for removal of both of these molecules are based on affinity purification of the extract before or after expression.

Although the use of tRNAs to incorporate fluorescent labels and photocleavable affinity tags directly into nascent proteins at both the N-terminal position and at specific amino acid residues has been demonstrated, there are possible limitations to this approach due to structural restrictions imposed by the protein synthesis machinery. (See Rothschild & Gite, *Curr. Opin. Biotech.*, 10: 64-70 (1999)). Overcoming this restriction is highly desirable in order to broaden the type of affinity linkers and fluorescent labels used for proteome array fabrication and readout. It would allow for "bar-coding" of individual proteins using encoding molecules such as DNA. Importantly, this would also facilitate "multiplex mapping" of proteome interactions as described below.

For this purpose, the present invention contemplates a methodology that relies on the incorporation of relatively small molecules with unique "chemically addressable" properties. Such properties facilitate selective modification of the protein with a wide variety of labels or tags after the protein is synthesized and folded. As an example of this approach, the present invention contemplates the incorporation of 1,3-phenyldiboronic acid (PDBA), using bis-salicylhydroxamic acid (bis(SHA)) as an affinity partner to post-translationally attach a much larger tag, such as DNA (FIG. 13).

In one embodiment using PDBA-bis(SHA) chemistry, DNA coding tags are attached to either the N-terminus of proteins, or alternatively through specific residues such as lysine. The present invention contemplates a bis(SHA) linker molecule (prepared as described in Example 23) with an amine handle suitable for attaching a variety of molecules, including DNA. For example, the desired protein-DNA conjugate can be created by first cross-linking amine group on the bis(SHA) moiety with 5'-SH modified DNA. (See FIG. 13). This DNA molecule would then bind specifically to PDBA-modified proteins. Several model proteins may be labeled at the N-terminus with a PDBA-conjugated amino acid. Following purification, these proteins may be incubated with a bis (SHA) modified surface (e.g. sepharose beads, microarray chip, microtiter plate). (See Example 25). The attachment is then verified by C-terminal epitope tag detection and the resultant signal intensity is compared to that achieved using a biotin-streptavidin attachment system In separate experiments, the same set of PDBA-proteins may be incubated with a fluorophore-bis(SHA) conjugate to create fluorescently labeled proteins. After a purification step to remove the excess fluorophore-bis(SHA) conjugate, formation and stability of the fluorophore-bis(SHA)-PDBA-protein conjugates may be evaluated using capture on a microarray-immobilized antibody directed at the C-terminal epitope.

EXPERIMENTAL

The following examples serve to illustrate certain preferred embodiments and aspects of the present invention and are not to be construed as limiting the scope thereof.

In the experimental disclosure which follows, the following abbreviations apply: eq. or eqs. (equivalents); M (Molar); μM (micromolar); N (Normal); mol (moles); mmol (millimoles); μmol (micromoles); nmol (nanomoles); g (grams); mg (milligrams); μg (micrograms); ng (nanogram); L (liters); ml (milliliters); μl (microliters); cm (centimeters); mm (millimeters); μm (micrometers); nm (nanometers); C (degrees Centigrade); rpm (revolutions per minute); EDTA (ethylenediaminetetracetic acid); O.D. (Optical Density units); DMF (dimethylformamide); dCTP (2'-deoxycytidine 5'-triphosphate); dUTP (2'-deoxyuridine 5'-triphosphate); RP-HPLC (Reverse Phase High Performance Liquid Chromatography); Roche Molecular (Roche Molecular Biochemicals, Indianapolis, Ind.); Gibco-BRL (Gibco-BRL Life Technologies, Inc., Rockville, Md.); Molecular Probes (Molecular Probes, Eugene, Oreg.); Sigma (Sigma Chemical Co., St. Louis, Mo.); Promega (Promega Corp., Madison, Wis.); AB (Applied Biosystems, Foster City, Calif.); DME (N,N-dimethylformamide); THF (tetrahydrofuran); TEAA (triethylammonium acetate).

EXAMPLE 1

In this example, a method for the preparation of 5-Methyl-1 (2-Nitrophenyl)ethanol (FIG. 18, Compound 2) is provided. Briefly, 5-Methyl-2-nitroacetophenone (FIG. 18, Compound 1)(Olejnik et al., 1995, *Proc. Nat.l Acad. Sci. USA*, 92: 7590-4; Olejnik et al., 1998, *Methods Enzymol.*, 291: 135-54) was dissolved in 5 ml of ethanol. To this solution, 5 mg of sodium borohydride was added in small portions until analytical thin layer chromatography (TLC) showed complete conversion to 5-Methyl-1(2-Nitrophenyl)ethanol. The reaction was terminated by addition of 5 ml acetone and acidified to pH 3.0 with 1 N HCl, followed by extraction with chloroform. The organic layer was dried and evaporated to give the target compound as yellowish oil. The resulting compound was used without any further purification.

EXAMPLE 2

Figure 18:
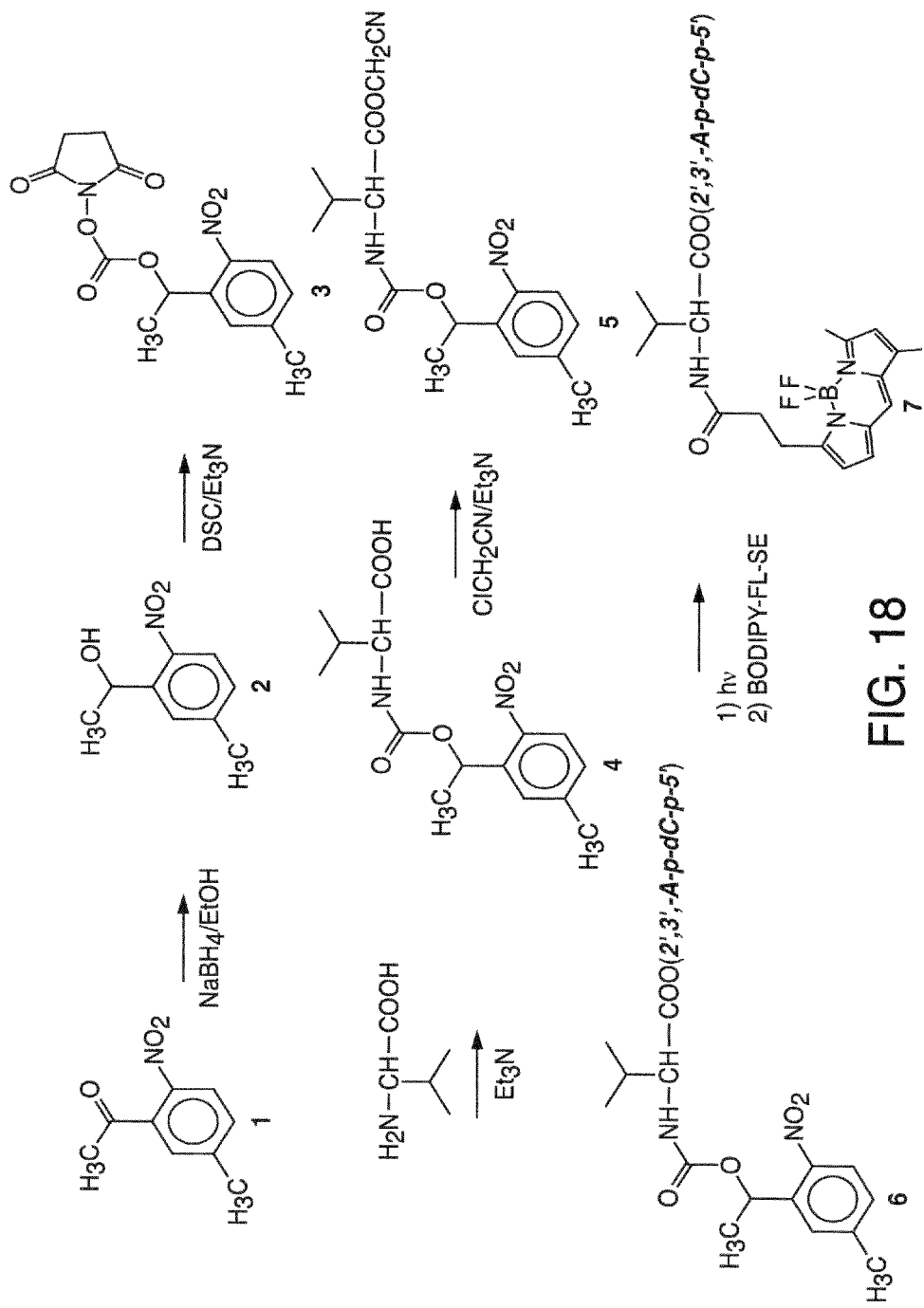
FIG. 18 shows one embodiment of the chemical scheme for the preparation of BODIPY-FL-Val-pdCpA using chemical aminoacylation/protective group replacement strategy.
Figure 19:
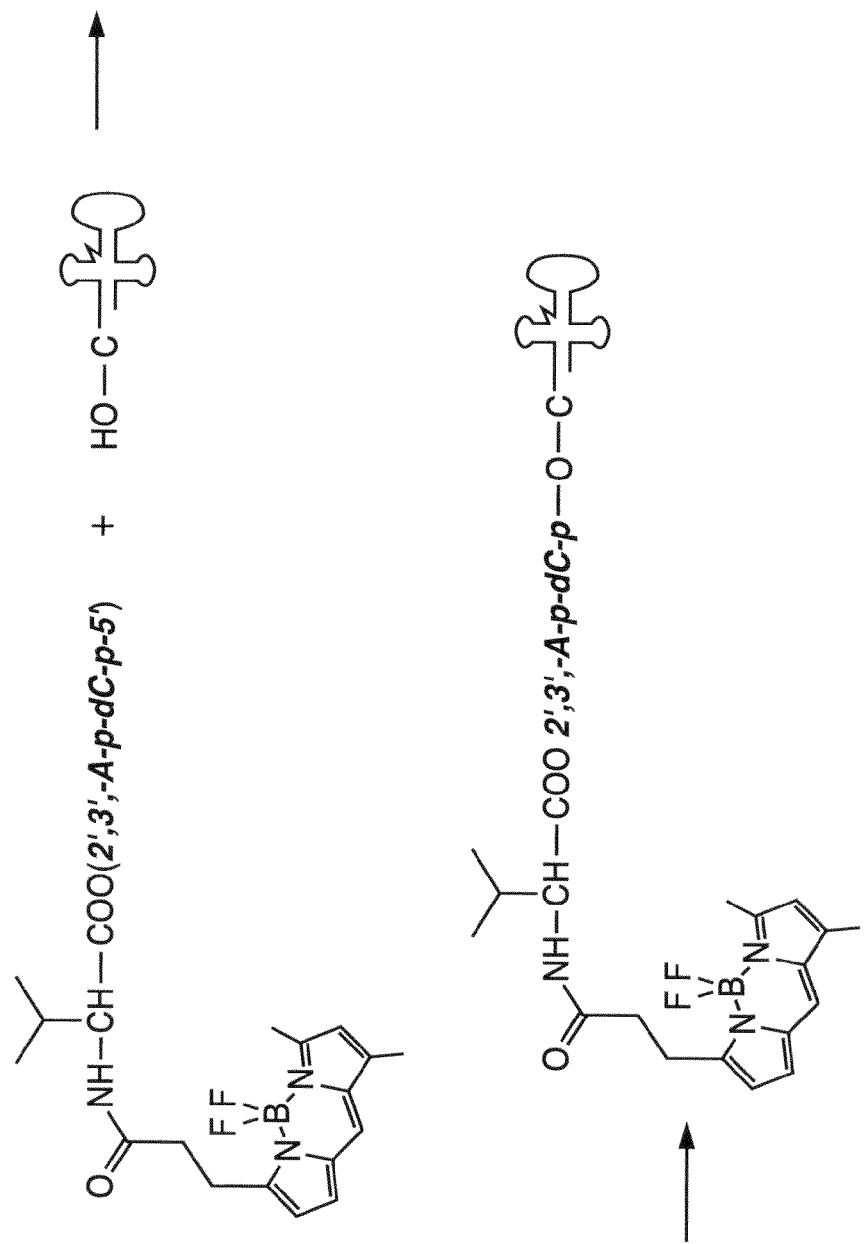
FIG. 19 shows one example of the preparation of chemically aminoacylated tRNA using BODIPY-FL-Val-pdCpA.

In this example, a method for the preparation of 5-Methyl-1(2-Nitrophenyl)ethyloxy-succinimidyl carbonate (FIG. 18, Compound 3) is provided. Briefly, 5-Methyl-1 (2-Nitrophenyl)ethanol (FIG. 18, Compound 2) (Npe-OH)(98 mg; 0.54 mmol) was dissolved in 2.5 ml of anhydrous acetonitrile. To this solution, 122 µl of triethylamine (0.81 mmol, 1.5 eq.) was added, followed by N,N'-disuccinimidyl carbonate (216 mg, 0.81 mmol, 1.5 eq.). The reaction mixture was stirred at room temperature until analytical TLC (98:1:1, chloroform:methanol:AcOH, v/v/v) showed quantitative conversion to active carbonate (Npe-ONHS)(FIG. 18, Compound 3). The resulting solution of active carbonate was used without purification.

EXAMPLE 3

In this example, a method for the preparation of Npe-Val-COOH (FIG. 18, Compound 4) is provided. Briefly, Valine (218 mg; 1.86 mmol) was suspended in 2 ml of water to which was added 260 µl of triethylamine. To this suspension, a solution containing 1.2 eq. of Compound 3 (see Example 2) in acetonitrile was added over 15 min. period, during which pH value of the mixture was adjusted to pH 8.0 if necessary by the addition of triethylamine. The mixture was stirred for 30 minutes and acidified by addition of 10 ml of 0.1 N HCl, followed by extraction with 3×20 ml AcOEt. Organic layers were combined, dried and evaporated to dryness. The crude product was dissolved in 20 ml chloroform and extracted with 4×30 ml of 0.1 N NaHCO$_3$, the aqueous layer acidified and re-extracted by chloroform to give 320 mg of pure target Npe-Val (FIG. 18, Compound 4).

EXAMPLE 4

In this example, a method for the preparation of Npe-Val-COOCH$_2$CN (FIG. 18, Compound 5) is provided. Briefly, Npe-Val (FIG. 18, Compound 4)(320 mg, 1 mmol) was dissolved in 320 µl of acetonitrile. To this solution was added triethylamine (280 µl, 2 eq.) and chloroacetonitrile (190 µl, 3 eq.). The mixture was stirred overnight at room temperature. 20 ml of methylene chloride was added followed by 20 ml of 1N NaHSO$_4$, the mixture was extracted with 4×20 ml methylene chloride. Organics were evaporated to dryness and purified on silica gel column using step gradient of ethyl acetate in hexane (10-50%) to give 300 mg of pure product (FIG. 18, Compound 5).

EXAMPLE 5

In this example, a method for the preparation of Npe-Val-pdCpA (FIG. 18, Compound 6) is provided. Briefly, 20 O.D.$_{A260}$ of pdCpA (Annovis) containing 2.2 equivalents of tetrabutylammonium counterion was dissolved in 40 µl of anhydrous DMF. To this solution was added a solution of 2 eq. of Npe-Val-COOCH$_2$CN (0.66 mg) in 10 µl DMF. The reaction was kept at room temperature for 2 hours. Next, the product was isolated using preparative HPLC to give 15 O.D.$_{A260}$ of compound 6.

EXAMPLE 6

In this example, a method for the preparation of BODIPY-Val-pdCpA (FIG. 18, Compound 7) is provided. Briefly, 15 O.D.$_{A260}$ of Npe-Val-pdCpA was dissolved in 500 µl of 25 mM NaOAc, pH 4.5, and irradiated for 20 minutes using 365 nm light (BlakRay XX-15, UVP). To the irradiated solution, 166 µl of BODIPY-FL-SE ([10 mg/ml]; 7 eq.) followed by 140 µl of 1N NaHCO$_3$. Additional portions of BODIPY-FL-SE solution (2×166 µl; total 21 eq.) were added after 5 and 10 minutes, respectively, and the reaction mixture was vortexed at room temperature for 45 minutes. The product (Compound 7) was isolated using preparative HPLC (Novapak C18, 10×100 mm, linear gradient of acetonitrile in 50 mM TEAA, pH 5.4 over 90 min., flow rate of 2 ml/min) and characterized by absorption at both 260 and 505 nm. The yield of BODIPY-Val-pdCpA was 7.25 O.D.$_{A260}$.

EXAMPLE 7

In this example, a method for the preparation of α-Npe, ε-Fmoc-Lys-COOH (FIG. 20, Compound 2) is provided. Briefly, α-NH$_2$, ε-Fmoc-lysine (FIG. 20, Compound 1)(200 mg, 0.54 mmol) was suspended in the mixture of 5 ml of acetonitrile and 2.5 ml of water. To this suspension, triethylamine (82 µl, 0.54 mmole) was added, and the mixture was gently heated (50° C.) until homogenous. The suspension was cooled down to 20° C., and the solution of Npe-ONHS added in 200 µl portions over a period of 10 minutes. The pH was adjusted to ~8.0 by addition of triethylamine. The mixture was stirred for an additional hour and then acidified to pH ~2.0 with 1N HCl and extracted with chloroform (2×20 ml). Extracts were dried and solvents removed under reduced pressure to give crude product with a yield of 187 mg (FIG. 20, Compound 2), purified on a silica gel column using step gradient of methanol in chloroform (0-4%).

EXAMPLE 8

Figure 20:
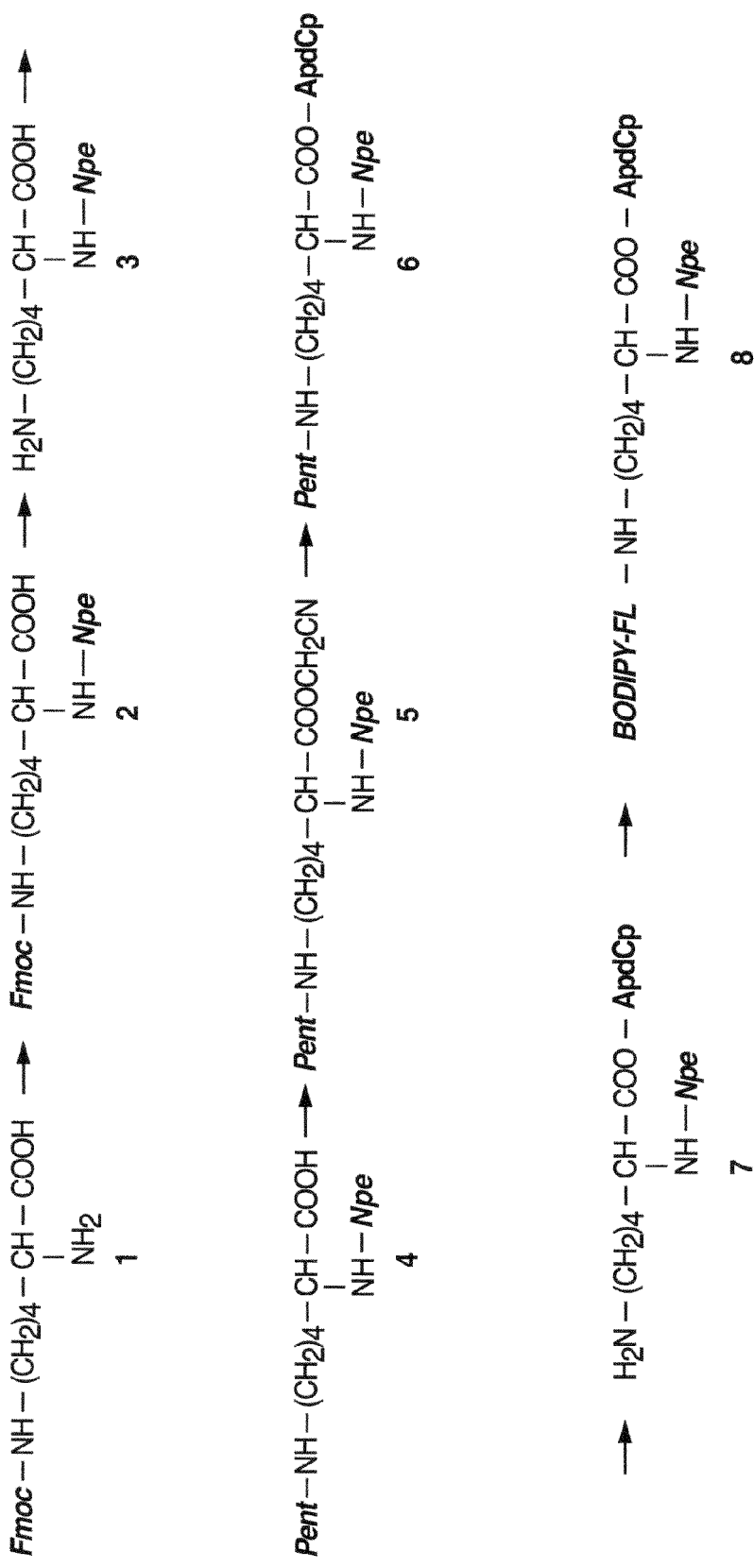
FIG. 20 shows one embodiment of the chemical scheme for the preparation of ε-BODIPY-FL, α-Npe-Lys-pdCpA using chemical aminoacylation/protective group replacement strategy.
Figure 21:
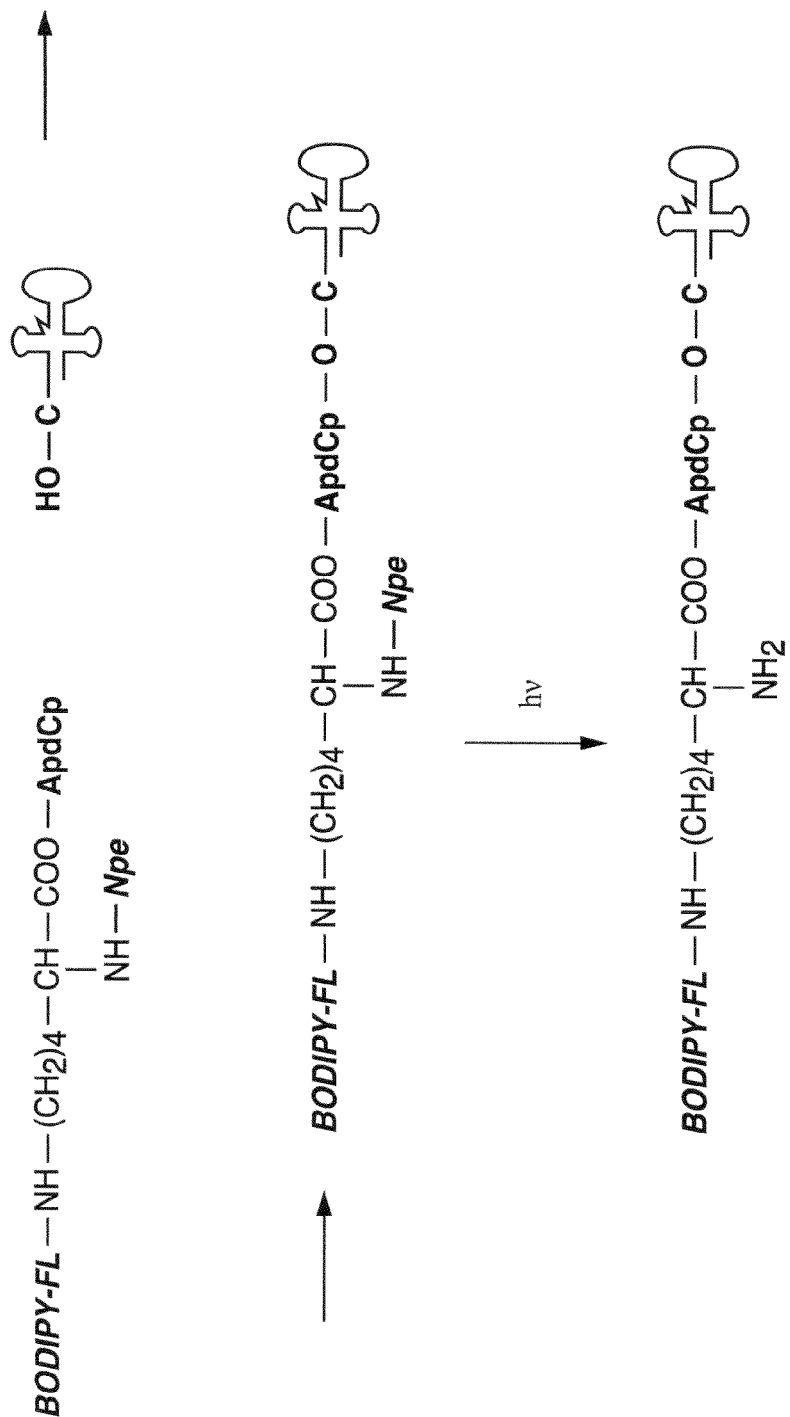
FIG. 21 shows one example of the preparation of chemically aminoacylated tRNA using ε-BODIPY-FL, α-Npe-Lys-pdCpA. An optional step of removing the Npe protective group from the alpha amino group is also shown.
Figure 22:
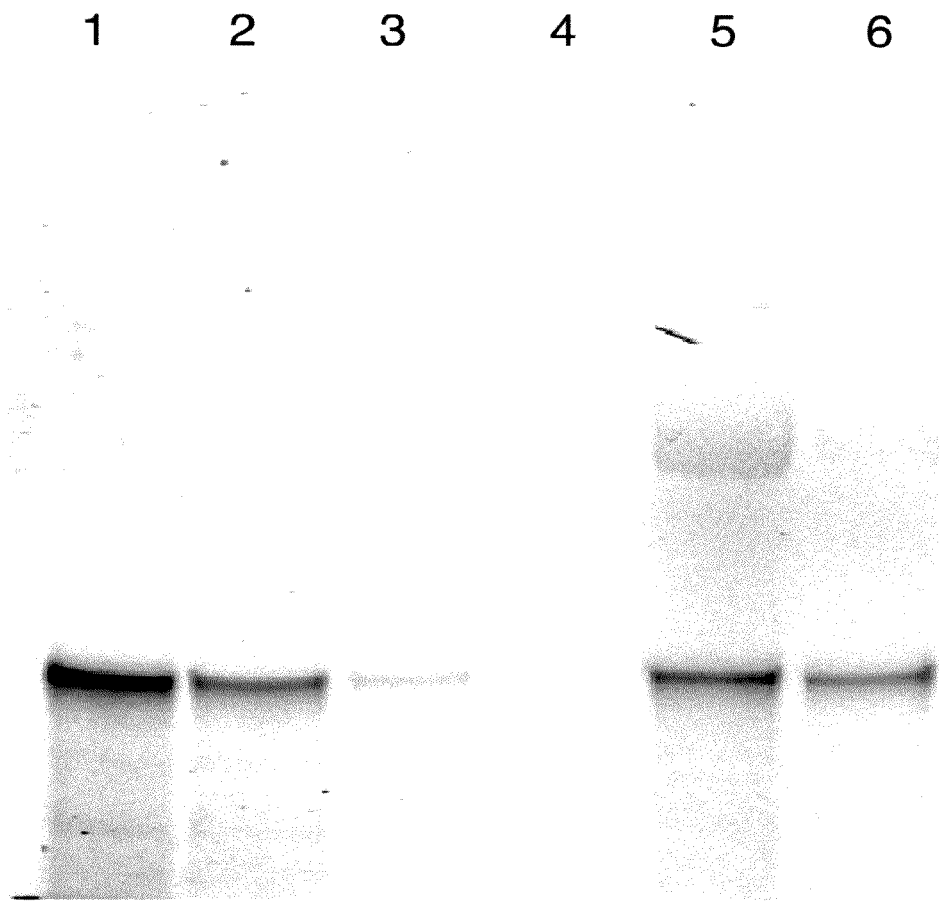
FIG. 22 α-PC-Biotin, ε-BODIPY-FL, α-hemolysin purification using streptavidin-agarose: lane 1 crude translation mixture, lane 2-flow through (unbound material), lane 3,4-wash, lane 5, 6-irradiation/elution.
Figure 23:
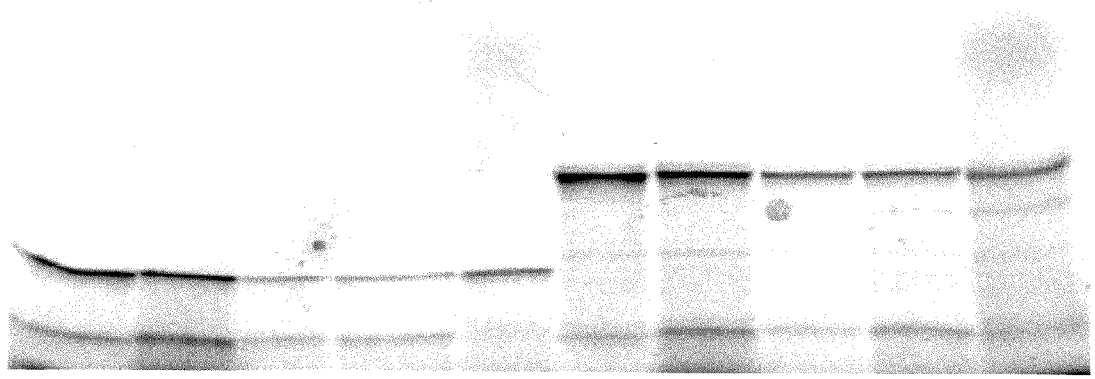
FIG. 23 depicts the results of the translation of Amber-1 proteins in the presence of initiator suppressor tRNA aminoacylated with bifunctional aminoacids. Lanes 1-5: DHFR, lanes 6-10: α-hemolysin. Lanes 1, 6-BODIPY-FL-Val, lanes 2, 7: α-biotin, ε-BODIPY-FL-Lys, lanes 3, 8 α-PC-biotin, ε-BODIPY-FL-Lys (1 µl), lanes 4, 9 α-PC-biotin, ε-BODIPY-FL-Lys (2 µl), lanes 5, 10 α-PC-biotin, ε-BODIPY-FL-Lys (2 µl), irradiated before translation.
Figure 24:
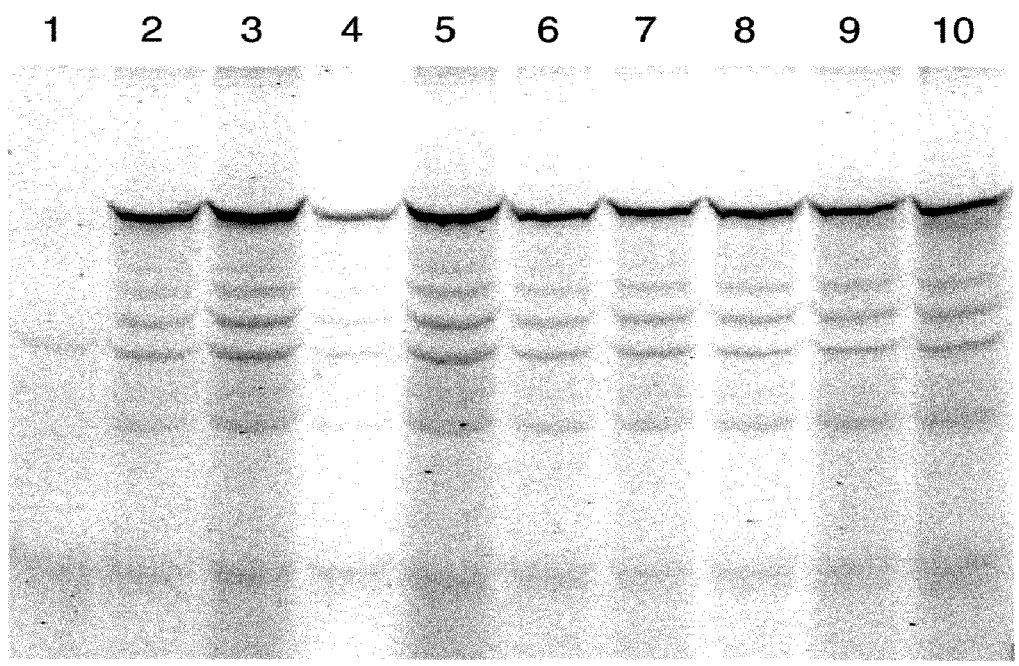
FIG. 24 depicts the results of the translation of luciferase (mRNA, QRR SP6) in rabbit reticulocyte lysate in the presence of chemically aminoacylated Lysine tRNA. TRNA aminoacylated chemically with α-Npe-, ε-BODIPY-FL-Lys. Lane 1: no irradiation, Lanes 2, 3: 2 minutes irradiation, Lanes 4, 5: 5 minutes irradiation, Lanes 6, 7: 10 minutes irradiation, Lanes 8, 9: 20 minutes irradiation, Lane 10: enzymatically aminoacylated Lys tRNA modified with BODIPY-FL. Lanes 2, 4, 6, 8: 0.5 µl load; Lanes 1, 3, 5, 7: 1.0 µl load.
Figure 25:
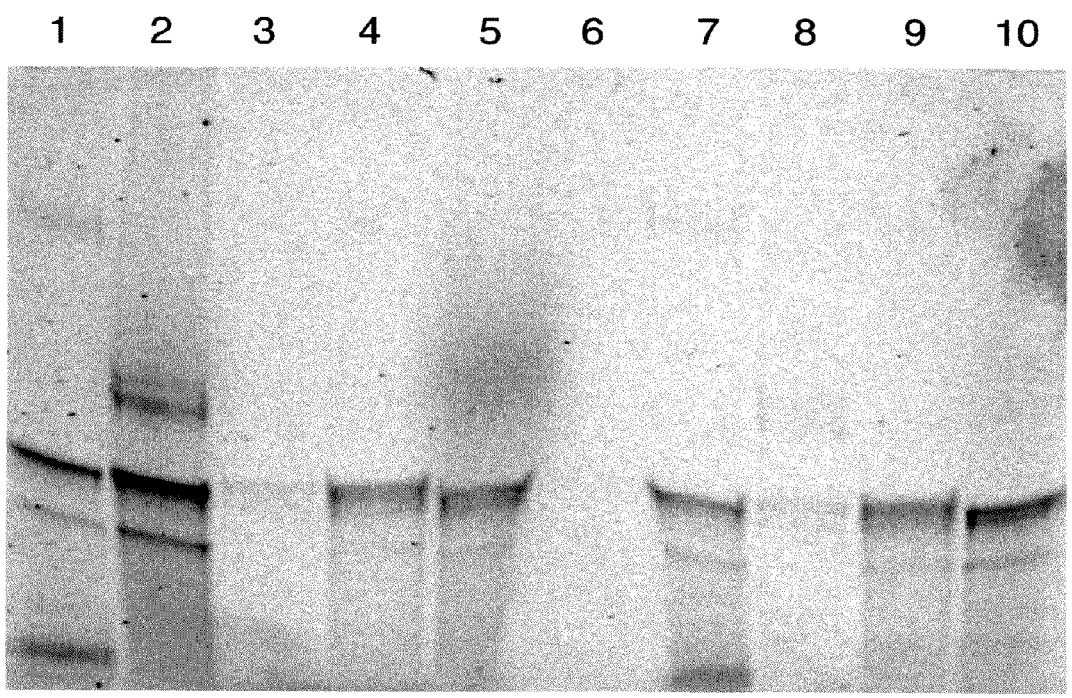
FIG. 25 depicts the results of the translation of α-hemolysin in the presence tRNAs aminoacylated with fluorescent lysine derivatives. Lane 1: ε-BODIPY-FL-Lys on tRNA-Lys prepared using enzymatic aminoacylation followed by BODIPY-FL modification, Lanes 2, 5, 10: α-Npe-, ε-BODIPY-FL-Lys on total tRNAs, Lanes 3, 8: α-Npe-, ε-FAM-6-Lys on total tRNAs, Lanes 4, 9: α-Npe-, ε-FAM-5-Lys on total tRNAs.
Figure 26:
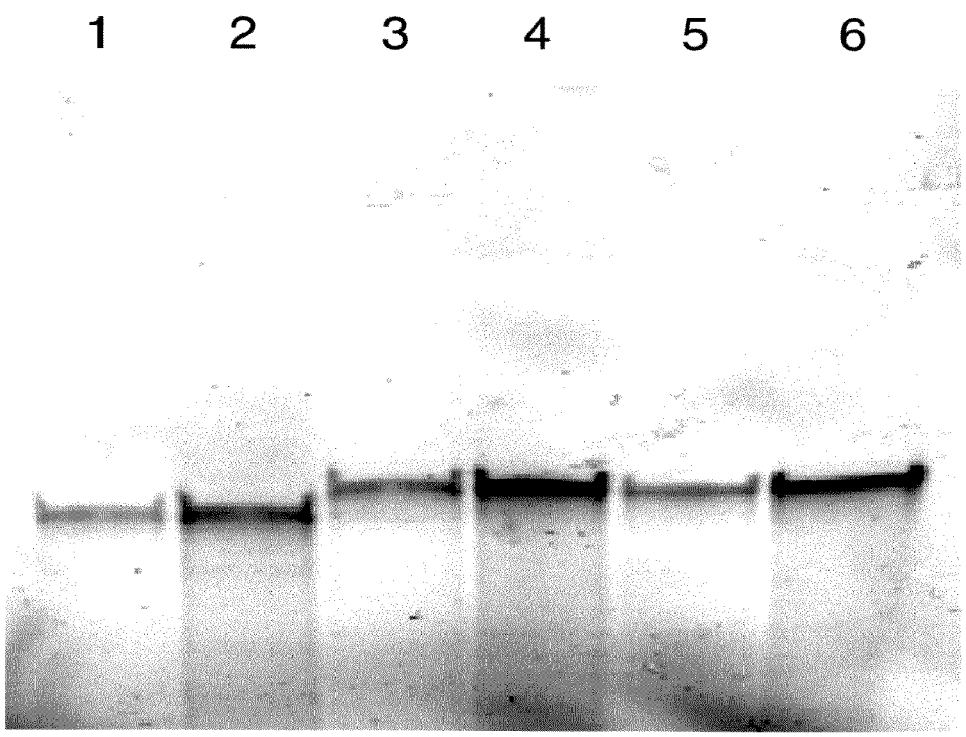
FIG. 26 depicts the results of the translation of Amber-1 hemolysin in the presence of initiator suppressor tRNAs aminoacylated with: 1, 2: α-Npe-, ε-BODIPY-FL-Lys; 3, 4: α-Npe-, ε-FAM-5-Lys, 5,6: α-Npe-, ε-FAM-6-Lys. Lanes 2, 4, 6: tRNA was irradiated prior to the addition to the translation reaction. Lanes 1, 3, 5: no irradiation.
Figure 27:
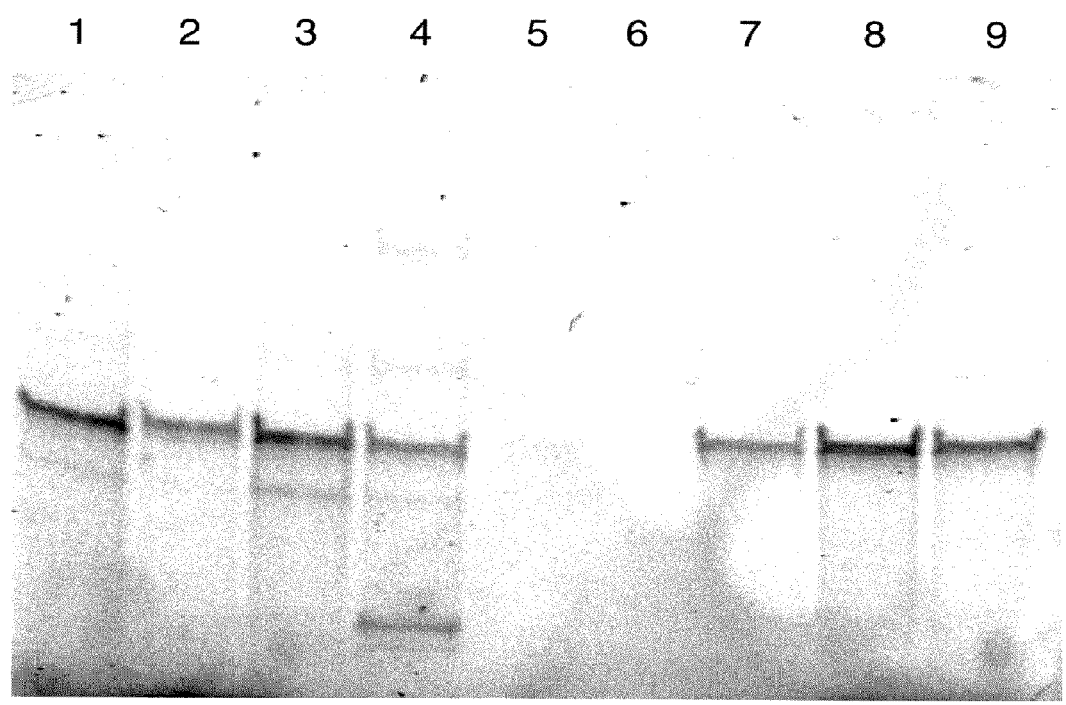
FIG. 27 depicts the results of the translation of normal (lanes 1-5) and Amber-1 (lanes 7-9) α-hemolysin in the presence of chemically misaminoacylated tRNAs. Lanes 1, 2, 4, and 5-total tRNAs (irradiated prior to translation), lane 1, 4: α-Npe-, ε-BODIPY-FL-Lys, Lane 2: α-Npe, ε-FAM-5-Lys, Lane 3: ε-BODIPY-FL-Lys (enzymatically prepared), Lane 5: α-Npe, ε-FAM-6-Lys, Lane 6: blank. Initiator suppressor tRNA aminoacylated with α-Npe, ε-FAM-5-Lys/Amber-1 hemolysin: Lane 7: no irradiation, Lane 8: irradiated before translation, Lane 9: irradiated after translation
Figure 28:
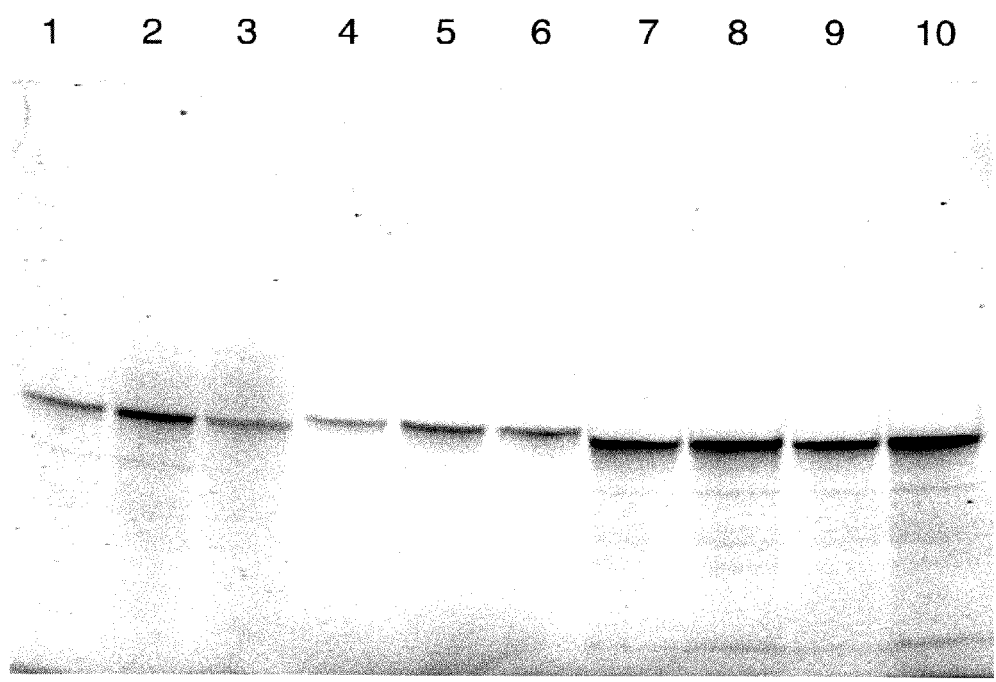
FIG. 28 depicts the results of the translation of Amber-1 α-hemolysin in the presence of suppressor initiator tRNA. Misaminoacylated with: α-Npe-, ε-BODIPY-FL-Lys (lanes 1-3); α-Npe, ε-FAM-6-Lys (lanes 4-6); and BODIPY-FL-Val (lanes 7-10). Lanes 1, 4: no irradiation, lanes 2, 5: irradiation prior to translation, lanes 3, 6: irradiation after the translation. Lanes 7, 9: 1 µl tRNA, lanes 8, 10: 2 µl of tRNA.
Figure 29:
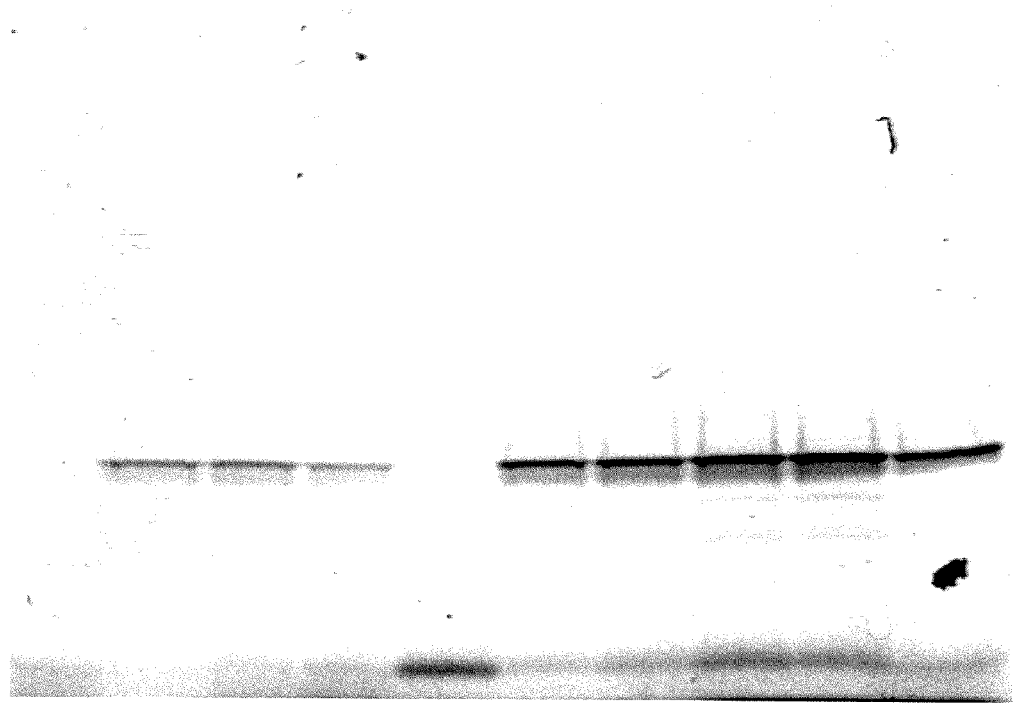
FIG. 29 depicts the results of the translation of WT (lanes 1-4) and Amber-1 α-hemolysin in the presence of ε-BODIPY-FL-Lys tRNA (lanes 1-4) and BODIPY-FL-Val initiator suppressor tRNA (lanes 5-10). Lanes 1, 5: no DNA template; lanes 1, 2, 3: 0.5, 1.0, 2.0 µl of tRNA respectively. Lanes 6, 7, 8, 9, 10 contained 0.5, 1.0, 2.0, 3.0, 4.0 µl of tRNA respectively.
Figure 30:
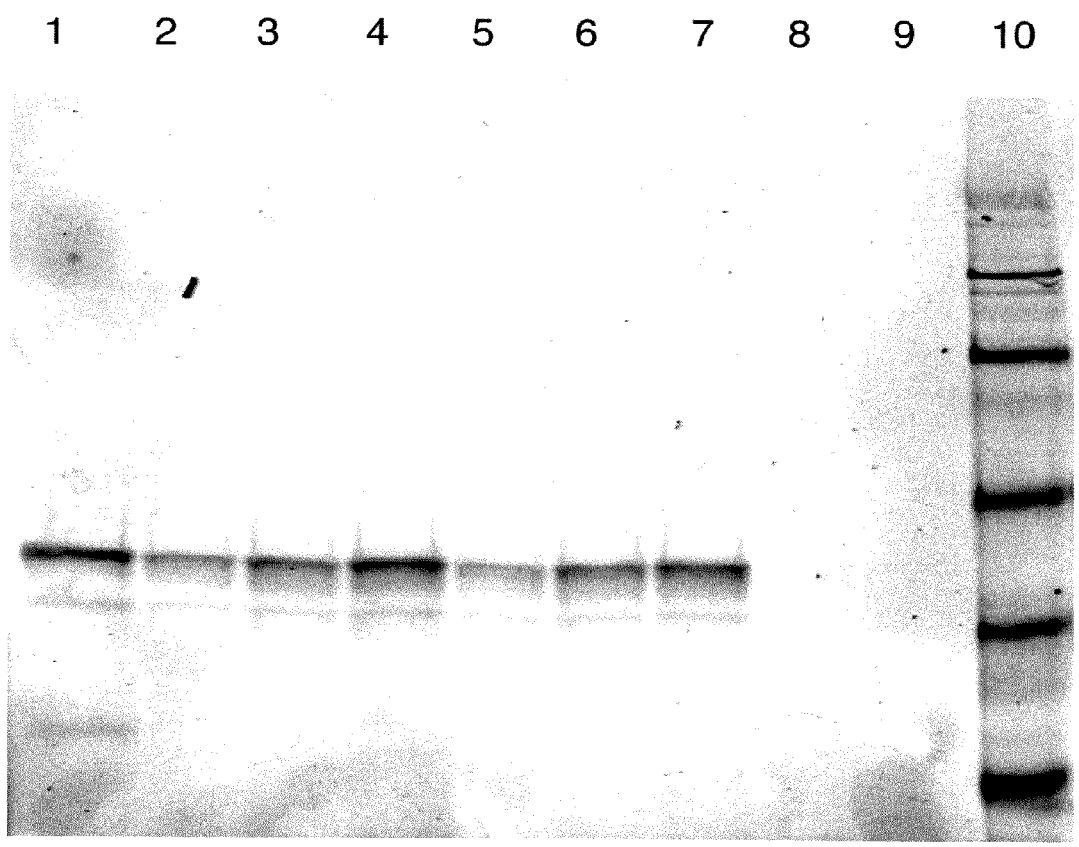
FIG. 30 depicts the results of the translation of α-hemolysin in the presence of enzymatically prepared ε-BODIPY-FL-Lys tRNA (lane 1), and crude (lanes 5-7) and purified α-Npe-, ε-BODIPY-FL-Lys on total tRNA (lanes 2-4). Lanes 2,5: 0.5 µl of tRNA, lanes 3,6: 1.0 µl of tRNA, lanes 4,7: 2.0 µl of tRNA.
Figure 31:
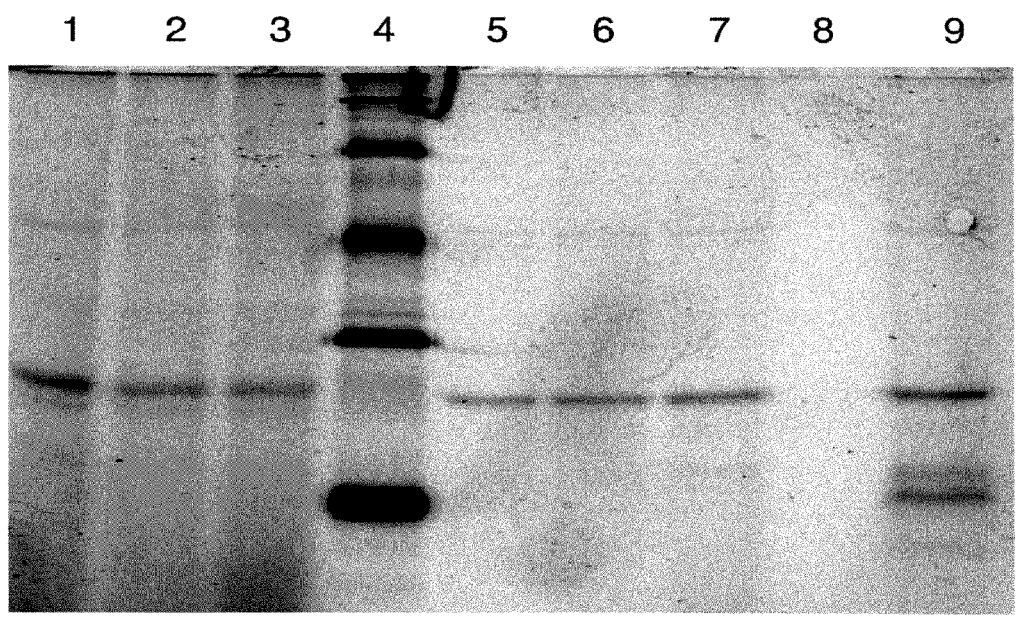
FIG. 31 depicts the results of the translation of bacterioopsin (bOp) gene in wheat germ extract in the presence of chemically and enzymatically prepared fluorophore (BODIPY-FL-Lys) labeled total tRNA. Lanes 1-3: chemically aminoacylated total tRNA with BODIPY-FL-Lys, 1, 2 and 3 µl, respectively. Lane 4: 1 µl fluorescent protein size marker (Sigma Cat. No. F-3526), lanes 5-7: chemically aminoacylated lysyl tRNA with BODIPY-FL-Lys, 1, 2 and 3 µl respectively. Lane 8: same as lane 7, but no irradiation prior to translation. Lane 9: enzymatically prepared lysyl tRNA aminoacylated with BODIPY-FL-Lys.
Figure 32:
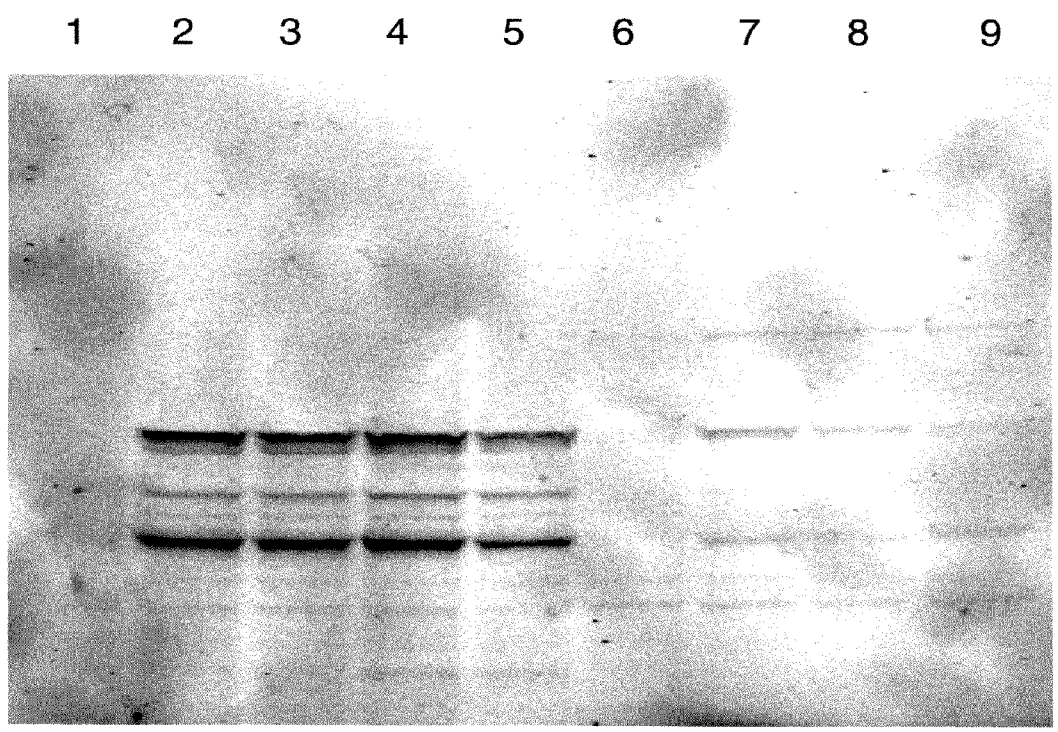
FIG. 32 depicts the results of the translation of luciferase gene in E. coli S30 system in the presence of chemically aminoacylated tRNAs. Lanes 1-5: tRNAs misaminoacylated with α-Npe, ε-BODIPY-FL-Lys. Lanes 6-9: tRNAs misaminoacylated with α-Npe, ε-5-FAM-Lys. Lane 1: total tRNAs without UV irradiation prior to translation; lanes 2 and 3-total tRNAs, 1 and 2 µl respectively (irradiated prior to translation). Lane 4 and 5: lysyl tRNA, 1 and 2 µl respectively (irradiated prior to translation). Lane 6: total tRNAs without UV irradiation prior to translation; lane 7 and 8-total tRNAs, 1 and 2 µl, respectively (irradiated prior to translation). Lane 9: lysyl tRNA, 1 µl (irradiated).
Figure 33:
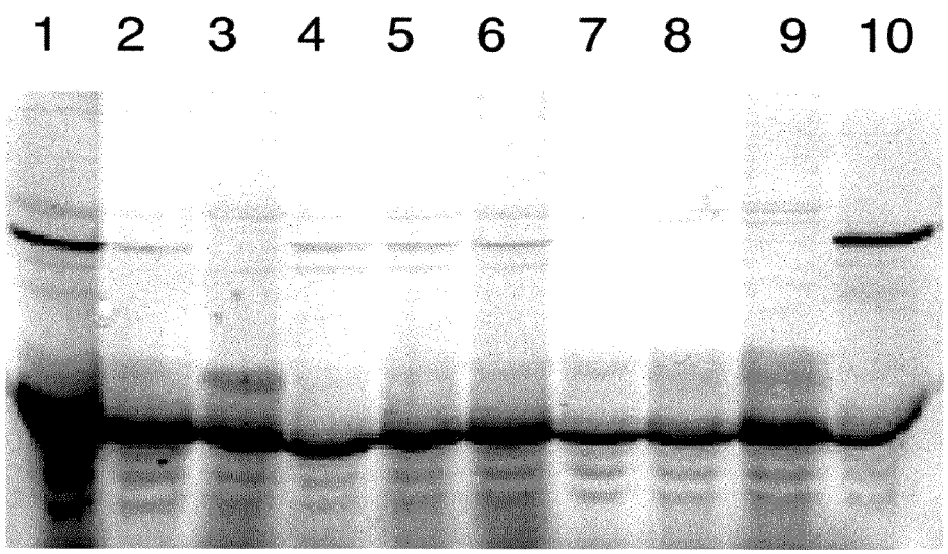
FIG. 33 depicts the results of the translation of α-hemolysin wild type (WT) and Amber-135 in the presence of misaminoacylated tRNAs. Lane 1: a mixture of WT and Amber- 135 α-hemolysin translated in the presence of BODIPY-FL-Lys tRNA. Lane 2: a mixture of Amber-1 and Amber-135 α-hemolysin. Lane 3: Amber-1/Amber-135 α-hemolysin double mutant translation in the presence of yeast Phe suppressor tRNA aminoacylated with α-Npe, ε-BODIPY-FL-Lys, no irradiation. Lanes 4-6: Amber-1/Amber-135 α-hemolysin double mutant translation in the presence of yeast Phe suppressor tRNA aminoacylated with α-Npe, ε-BODIPY-FL-Lys, irradiated prior to translation, 1, 2 and 3 μl of tRNA added, respectively. Lanes 7-9: Amber-1/Amber-135 α-hemolysin double mutant translation in the presence of yeast Phe suppressor tRNA aminoacylated with α-Npe, ε-5-FAM-Lys, irradiated prior to translation, 1, 2 and 3 μl of tRNA added, respectively. Lane 10 Amber-1/Amber-135 α-hemolysin double mutant translation in the presence of E. coli Tyr suppressor tRNA (chargeable in the translation system).
Figure 34:
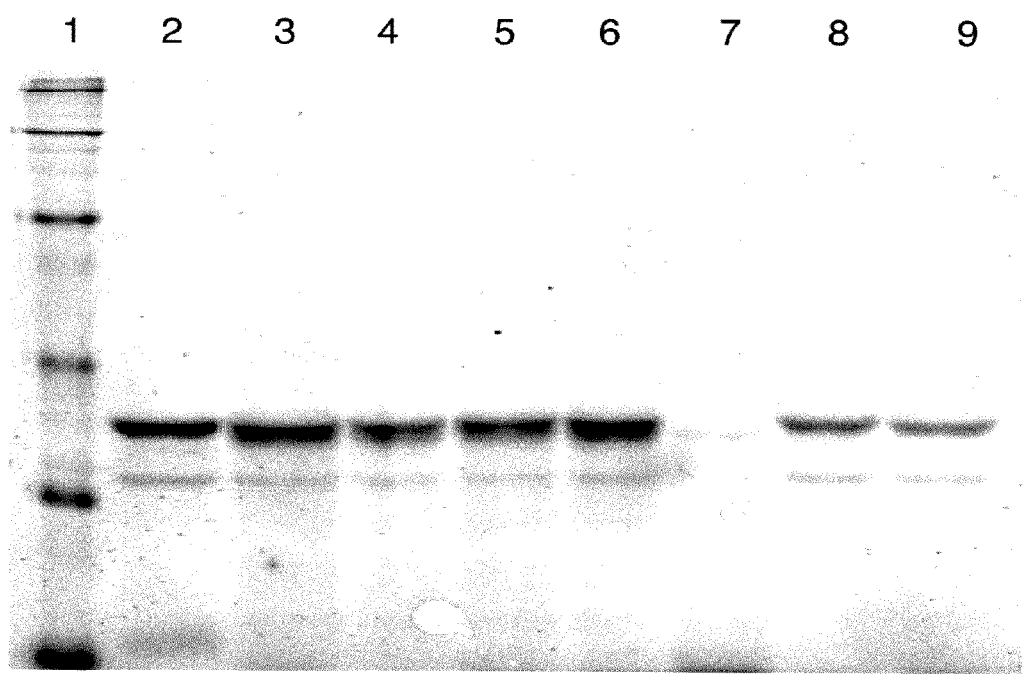
FIG. 34 depicts the results of the translation of α-hemolysin in the presence of enzymatically and chemically aminoacylated tRNAs. Lane 1: fluorescent protein standards, lane 2: enzymatically prepared lysyl tRNA modified with ε-BODIPY-FL-Lys, lanes 3, 4: chemically aminoacylated total tRNA (α-Npe, ε-BODIPY-FL-Lys), irradiation 10 minutes prior to translation, 2 and 1 μl added, respectively. Lanes 5 and 6: chemically aminoacylated total tRNA (α-Npe, ε-BODIPY-FL-Lys), irradiation 5 minutes prior to translation, 2 and 1 μl added, respectively. Lane 7: chemically aminoacylated total tRNA (α-Npe, ε-BODIPY-FL-Lys), no irradiation prior to translation, 2 μl added. Lanes 8, 9: chemically aminoacylated lysyl tRNA (α-Npe, ε-BODIPY-FL-Lys), irradiation 10 and 5 minutes, respectively, 2 μl added.
Figure 35:
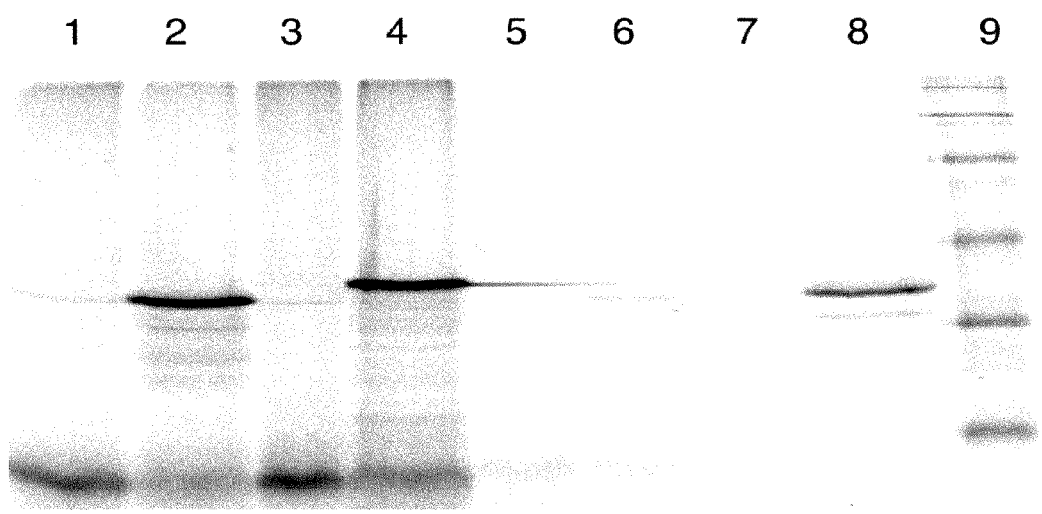
FIG. 35 depicts the results of the translation of α-hemolysin in the presence of chemically aminoacylated tRNAs. Lane 1, 2: initiator suppressor tRNA aminoacylated with BODIPY-FL-Val, lane 1–no DNA template, lane 2+DNA template. Lanes 3,4: initiator suppressor tRNA aminoacylated with Fluorescein-EX-Val, lane 3–no DNA template, lane 4+DNA template. Lanes 5-8: initiator suppressor tRNA chemically aminoacylated with α-Npe, ε-BODIPY-FL-Lys, lane 5–no DNA, lane 6+DNA template, lane 7–no DNA, irradiation prior to translation, lane 8+DNA template, irradiation prior to translation. Lane 9: fluorescent protein size marker.
Figure 36:
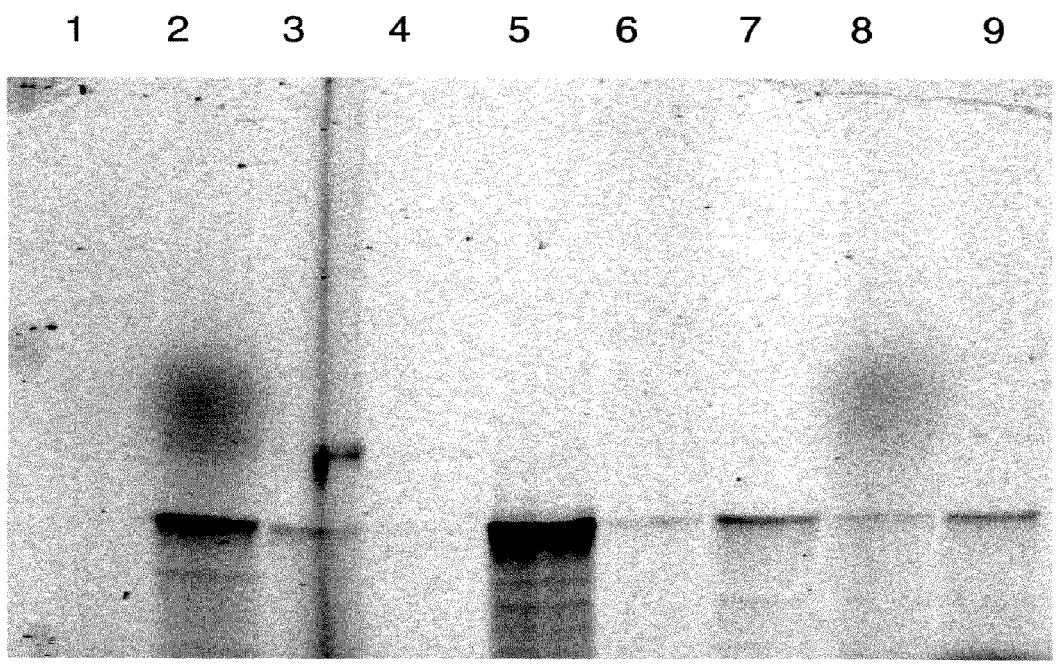
FIG. 36 depicts the results of the translation of WT α-hemolysin in the presence of total tRNAs misaminoacylated with α-Npe, ε-BODIPY-FL-Lys and α-Npe, β-BODIPY-FL-Dpr (diaminopropionic acid). Lanes 1, 2: total tRNA aminoacylated with α-Npe, ε-BODIPY-FL-Lys, lane 1-no irradiation, lane-2-irradiation prior to translation. Lanes 3,4: total tRNA aminoacylated with α-Npe, β-BODIPY-FL-Dpr, lane 3-irradiated, lane 4-non irradiated. Lanes 5-9: translation of Amber-1 α-hemolysin in the presence of aminoacylated initiator suppressor tRNA. Lane 5: BODIPY-FL-Val, lanes 6, 8-α-Npe, ε-BODIPY-FL-Lys, lane 7,9-α-Npe, β-BODIPY-FL-Dpr. Lanes 6, 7: irradiated prior to translation. Lanes 8, 9: non-irradiated.
Figure 37:
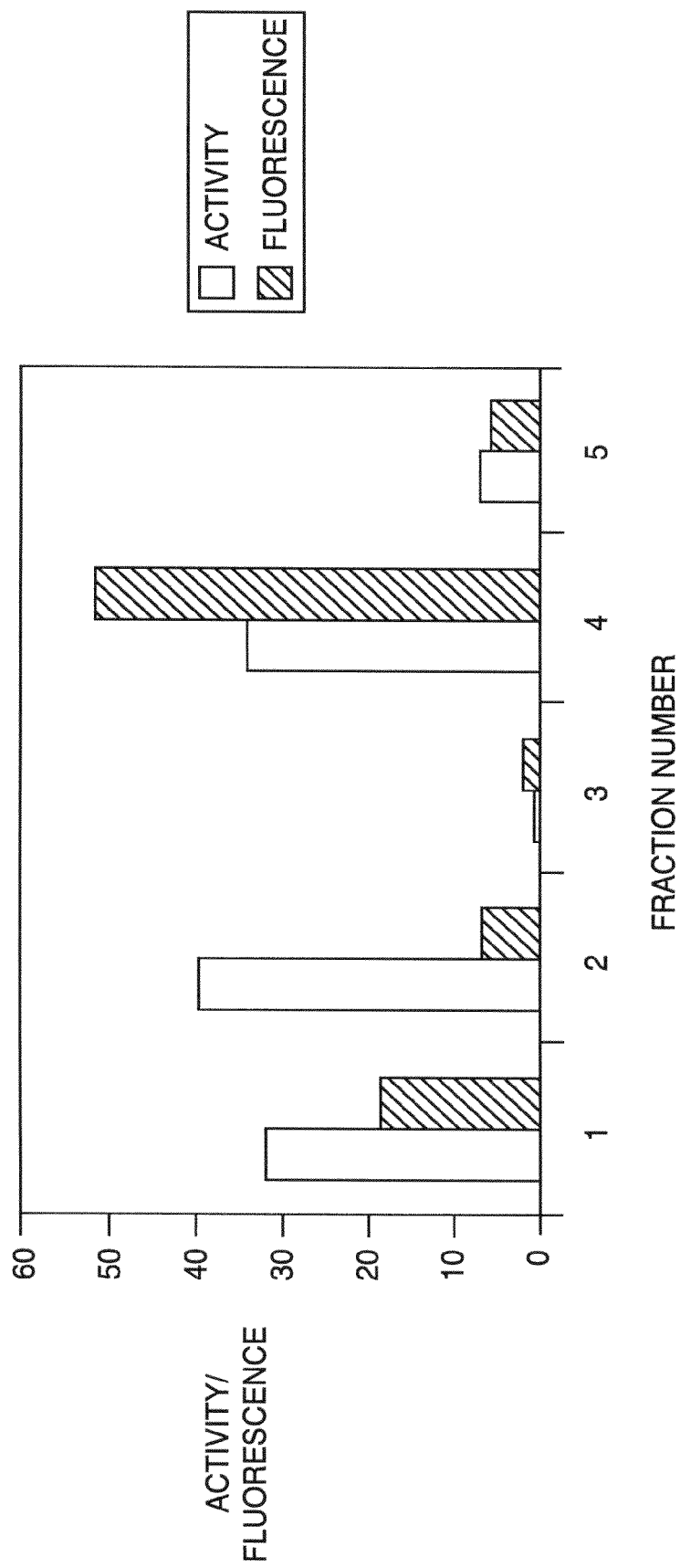
FIG. 37 depicts the results of the purification of in vitro translated α-PC-Biotin, ε-BODIPY-FL, α-hemolysin using streptavidin-agarose in graph form (activity/florescence). Fractions: 1—crude translation mixture, 2—flow through (unbound material), 3—wash, 4 and 5—irradiation/elution.
Figure 38:
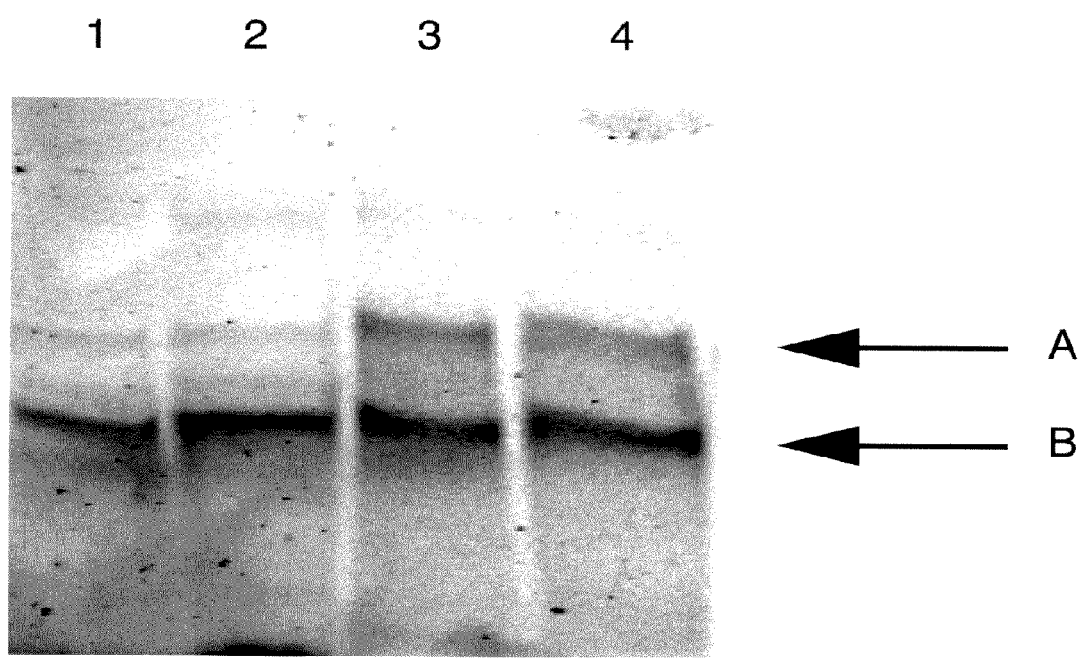
FIG. 38 depicts the results of the translation of amber-1 α-hemolysin template in the presence of α-Npe, ε-(PDBA)-Lys-initiator suppressor tRNA and BODIPY-FL-Lys tRNA. Lanes 1,2—no initiator suppressor tRNA added, lanes 3, 4 initiator suppressor tRNA carrying α-Npe, ε-(PDBA)-Lys added. Lane 3 non-irradiated, lane 4—irradiated (the Npe protective group removed). Fluorescent band of β-lactamase (B) visible in all lanes. The band of α-hemolysin (A) visible only after addition of initiator suppressor tRNA aminoacylated with α-Npe, ε-(PDBA)-Lys.

In this example, a method for the preparation of α-Npe, ε-Pent-Lys-COOH (FIG. 20, Compound 4) is provided. Briefly, to a solution of α-Npe, ε-Fmoc-Lys (FIG. 20, Compound 2)(76 mg, 0.132 mmol) in 1.5 ml DMF, was added 77 µl (0.66 mmol, 5 eq.) of tetramethylguanidine. The solution was stirred for 20 minutes after which TLC (9:1:1) results showed complete conversion into a ninhydrine-positive product (FIG. 20, Compound 3, not isolated). The solution was then acidified with 1N HCl to pH ~8.5 and pentenoic anhydride (1.1 eq., 25 µl, 0.145 mmol). The solution was stirred for 45 minutes after which TLC showed complete conversion to Compound 9 (FIG. 18). The mixture was acidified with 1N HCl to pH 1.0 and extracted with chloroform (3×5 ml). Organic extracts were combined and solvents removed under reduced pressure to give 90 mg of crude product as yellowish oil. The product was purified on a silica gel column using a step gradient of methanol in chloroform (0-10%) to give 51 mg of pure α-Npe, ε-Pent-Lys (FIG. 20, Compound 4)

EXAMPLE 9

In this example, a method for the preparation of α-Npe, ε-Pent-Lys-COOCH$_2$CN (FIG. 20, Compound 5) is provided. Briefly, α-Npe, ε-Pent-Lys (4)(51 mg, 0.117 mmol) was dissolved in 100 µl of triethylamine (6 eq.) and to this solution 66 µl of chloroacetonitrile (9 eq.) was added. The solution was stirred overnight at room temperature, at which time TLC (98:1:1) showed complete conversion of starting material into product. The solution was acidified with 1 N HCl to pH 1.0 and partitioned between chloroform and water. The organic layer was dried with sodium sulfate, evaporated under reduced pressure. The residue was re-dissolved in acetonitrile and freeze-dried to give 48 mg of pure α-Npe, ε-Pent-Lys-COOCH$_2$CN (FIG. 20, Compound 5) as brownish oil.

EXAMPLE 10

In this example, a method for the preparation of α-Npe, ε-Pent-Lys-pdCpA (FIG. 20, Compound 6) is provided. Briefly, pdCpA (10 O.D.$_{A260}$, 400 nmol)(Annovis) was dissolved in 10 µl of water, and to this solution, 10 µl of tetrabutylammonium hydroxide (0.01 M) was added. The sample was freeze-dried, re-dissolved in 20 µl of dry DMF and 20 µl of α-Npe, ε-Pent-Lys-COOCH$_2$CN (100 mM; 2.5 eq.) solution in DMF was added. The mixture was incubated at room temperature for 2-3 hrs after which RP-HPLC showed 95% conversion into product. The product was purified using preparative HPLC to give a yield of 6 O.D.$_{A260}$ of α-Npe, ε-pentenoyl-Lys-pdCpA.

EXAMPLE 11

In this example, a method for the preparation of α-Npe, ε-NH$_2$-Lys-pdCpA (FIG. 20, Compound 7) is provided. Briefly, α-Npe, ε-pentenoyl-Lys-pdCpA (14 O.D.$_{A260}$)(FIG. 20, Compound 6) was dissolved in 200 µl of water. To this solution was added 20 µl of 3M NaOAc, pH 4.5 followed by 200 µl of 25 mM solution of I$_2$ in THF. The mixture was incubated at room temperature for 3 hrs and analyzed by RP-HPLC showing almost complete conversion to α-Npe, ε-NH$_2$-Lys-pdCpA. Product was purified using RP-HPLC. Fractions containing product were pooled and freeze-dried to give a yield of 7.4 O.D.$_{A260}$ of α-Npe, ε-NH$_2$-Lys-pdCpA.

EXAMPLE 12

In this example, a method for the preparation of α-Npe, ε-BODIPY-FL-Lys-pdCpA (FIG. 20, Compound 8) is provided. Briefly, α-Npe, ε-NH$_2$-Lys-pdCpA (8 O.D.$_{A260}$, 320 nmol) was dissolved in 100 µl of water and 2 µl of 3M NaOAc, pH 4.5 was added. To this solution a 25 mM solution of BODIPY-FL, SE (100 µl; 7.8 eq.) was added and the mixture was incubated at room temperature for 2-3 hours, after which RP-HPLC showed almost complete conversion into α-Npe, ε-BODIPY-FL-Lys-pdCpA. The product (yield=4.32 O.D.$_{A260}$) was isolated using preparative HPLC. An aliquot (0.1 O.D.$_{A260}$) was added to 10 µl of 0.2 M Tris-HCL (pH 9.5), incubated at 37° C. for 1 hour, and analyzed by HPLC showing complete conversion into pdCpA. A separate aliquot (0.1 O.D.$_{A260}$) was added to 10 µl of 10 mM NaOAc (pH 4.5), irradiated 15 minutes using 365 nm light (BlakRay XX-15, UVP Inc.) and analyzed by HPLC showing removal of the Npe protective group. In addition, the UV-VIS spectra measured showed an absorbance ratio (A505/A260 nm) of 3:1 (approximately equal to the theoretical yield).

EXAMPLE 13

In this example, a method for the preparation of α-Npe, ε-(5-FAM)-Lys-pdCpA is provided. Briefly, α-Npe, ε-NH$_2$-Lys-pdCpA (obtained as (8 O.D.$_{A260}$, 320 mmol) was dissolved in 100 µl of water and 2 µl of 3M NaOAc, pH 4.5 was added. To this solution, a 25 mM solution of 5-FAM (100 µl; 7.8 eq.) was added and the mixture was incubated at room temperature for 24 hours, after which RP-HPLC showed ~70% conversion into α-Npe, ε-(5-FAM)-Lys-pdCpA. The product (yield=4.56 O.D.$_{A260}$) was isolated using preparative HPLC and characterized by alkaline hydrolysis, irradiation with near UV light, and UV-Vis absorption spectra.

EXAMPLE 14

In this example, a method for the preparation of α-Npe, ε-(6-FAM)-Lys-pdCpA is provided. Briefly, α-Npe, ε-NH$_2$-Lys-pdCpA (8 O.D.$_{A260}$, 320 nmol) was dissolved in 100 µl of water, followed by the addition of 2 µl of 3M NaOAc, pH 4.5. To this solution, a 25 mM solution of 5-FAM (100 µl; 7.8 eq.) was added and the mixture was incubated at room temperature for 24 hours, after which RP-HPLC showed ~70% conversion into α-Npe, ε-(6-FAM)-Lys-pdCpA. The product (yield=3.79 O.D.$_{A260}$) was isolated using preparative HPLC and characterized by alkaline hydrolysis, irradiation with near UV light, and UV-Vis absorption spectra.

EXAMPLE 15

In this example, a method for the preparation of α-Npe, ε-(PDBA)-Lys-pdCpA is provided. Briefly, α-Npe, ε-NH$_2$-Lys-pdCpA (8 O.D.$_{A260}$, 320 nmol) was dissolved in 100 µl of water and 2 µl of 3M NaOAc, pH 4.5 was added. To this solution a 25 mM solution of PDBA-X-NHS (100 µl; 7.8 eq.) was added and the mixture was incubated at room temperature for 24 hours, after which RP-HPLC showed ~75% conversion into α-Npe, ε-(PDBA)-Lys-pdCpA. The product (yield=4.2 O.D.$_{A260}$) was isolated using preparative HPLC and characterized by alkaline hydrolysis, irradiation with near UV light, and UV-Vis absorption spectra.

EXAMPLE 16

In this example, methods for the preparation of several Diaminopropionic acid (Dpr) derivatives useful in the present invention are presented.

A. Preparation of α-Npe, β-Fmoc-Dpr-COOH

Briefly, α-tBoc, β-Fmoc-Dpr-COOH (300 mg; 0.703 mmol) was added to 4 ml of a 50% trifluoroacetic acid (TFA) solution in CH$_2$Cl$_2$. The solution was stirred at room temperature for 15 min. and the solvents were evaporated under reduced pressure. The resulting residue was re-dissolved in acetonitrile (5 ml) and toluene (2 ml) and solvents removed under reduced pressure. This was repeated 2 more times. The remaining residue was dried in vacuum for 1 hr. The α-NH$_2$, β-Fmoc-Dpr-COOH was dissolved in 4 ml of acetonitrile and 2 ml of H$_2$O. To this solution 160 µl of N,N'-diisopropylethylamine (DIPEA) was added followed by a solution of Npe-ONHS in 100 µl portions prepared from 127 mg (0.703 mmol) of Npe-OH as described above. The solution was stirred at room temperature for 1 hr and acidified with 1N HCl to pH 2.0. The crude product was extracted using chloroform and purified on a silica gel column using step gradient of MeOH in chloroform (0-4%) with a yield of 140 mg (i.e., a 49% yield).

B. Preparation of α-Npe, β-Pent-Dpr-COOH

Briefly, α-Npe, β-Fmoc-Dpr-COOH (70 mg, 0.117 mmol) was dissolved in 1.5 ml of DMF and to this solution 68 µl (0.585 mmol) of tetramethylguanidine was added. The solution was stirred at room temperature for 20 minutes and the pH adjusted to ~8.5 by the addition of 1N HCl. Pentenoyl anhydride (23 µl; 0.128 mmol) was added and the reaction was incubated for additional 45 min., acidified to pH 2.0 with 1 N HCl, and the product extracted with chloroform (3×10 ml). Solvents were removed under reduced pressure and the product was purified on a silica gel column using a step gradient of methanol in chloroform (0-12%) with a yield of 40 mg (i.e. a 55% yield).

C. Preparation of α-Npe, β-Pent-Dpr-COOCH$_2$CN

Briefly, α-Npe, β-Pent-Dpr-COOH (40 mg, 0.101 mmol) was added to 90 µl of triethylamine followed by 60 µl of chloroacetonitrile. The reaction was stirred overnight at room temperature, at which time TLC showed complete conversion of the starting material. The reaction was acidified to pH 1.0 with 1N HCl and extracted with chloroform. The solvents were evaporated under reduced pressure, re-dissolved in DMF and used for aminoacylation without any further purification.

D. Preparation of α-Npe, β-Pent-Dpr-COO-pdCpA

Briefly, pdCpA (10 O.D.$_{A260}$, 400 nmol) was dissolved in 10 µl of water and to this solution 10 µl of tetrabutylammonium hydroxide (0.01M) was added. The sample was freeze-dried, re-dissolved in 20 µl of dry DMF and 20 µl of α-Npe, β-Pent-Dpr-COOCH$_2$CN (100 mM; 2.5 eq.) solution in DMF was added. The mixture was incubated at room temperature for 2-3 hrs after which RP-HPLC showed 95% conversion into product. The product was purified using preparative HPLC to give a yield of 31 O.D.$_{A260}$ of α-Npe, β3-Pent-Dpr-COO-pdCpA.

E. Preparation of α-Npe, β-NH$_2$-Dpr-COO-pdCpA

Briefly, α-Npe, β-Pent-Dpr-COO-pdCpA (31 O.D.$_{A260}$, 1.24 µmol) was dissolved in 440 µl of H$_2$O and to this solution 44 µl of 3M NaOAc, pH 4.5 was added followed by 442 µl of 25 mM I$_2$ in THF. After 2 hrs at room temperature RP-HPLC showed almost complete conversion to the product. The product was purified using RP-HPLC to give a yield of 20.5 O.D.$_{A260}$ of α-Npe, β-NH$_2$-Dpr-COO-pdCpA.

F. Preparation of α-Npe, β-BODIPY-FL-Dpr-COO-pdCpA

Briefly, α-Npe, β-NH$_2$-Dpr-COO-pdCpA (5 O.D.$_{A260}$) was dissolved in 50 µl of H$_2$O and to this solution 5 µl of 1 M NaOAc, pH 4.5 was added followed by 40 µl of 25 mM solution of BODIPY-FL in DMF (5 eq.). The reaction was kept at room temperature for 3 hrs, after which RP-HPLC analysis showed almost complete conversion. Product was isolated using preparative RP-HPLC with a yield of 4.2 O.D.$_{A260}$

EXAMPLE 17

In this example, methods for the preparation of several bifunctional amino acid derivatives useful in the present invention are presented.

A. Preparation of α-Biotin, β-BODIPY-FL-Dpr-COO-pdCpA

Briefly, 2 O.D.$_{A260}$ of α-Npe, β-BODIPY-FL-Dpr-COO-pdCpA was prepared as described in Example 16F and dissolved in 50 µl of water, followed by the addition of 20 µl of a 25 mM solution of Biotin-NHS in DMF. The mixture was irradiated for 15 min. using a BlakRay XX-15 lamp (UVP, Inc., San Gabriel, Calif.) at a distance of 10 cm, and then was incubated at room temperature for additional 2 hours. The target compound was purified using RP-HPLC with a yield of 0.68 O.D.$_{A260}$.

B. Preparation of α-Biotin, ε-BODIPY-FL-Lys-pdCpA

Briefly, 2 O.D.$_{A260}$ α-Npe, ε-BODIPY-FL-Lys-pdCpA was prepared as described in Example 12 and dissolved in 50 µl of water, followed by the addition of 20 µl of a 25 mM solution of Biotin-NHS in DMF. The mixture was irradiated for 15 min. using a BlakRay XX-15 lamp (UVP, Inc., San Gabriel, Calif.) at a distance of 10 cm, and then was incubated at room temperature for additional 2 hours. The target compound was purified using RP-HPLC with a yield of 0.68 O.D.$_{A260}$.

C. Preparation of α-PC-Biotin, ε-BODIPY-FL-Lys-pdCpA

α-Npe, ε-BODIPY-FL-Lys-pdCpA (3.7 O.D.$_{A260}$) was dissolved in 200 µl of H$_2$O, 2 µl of 3M NaOAc, pH 4.5 was added and the solution was irradiated for 15 min. using a BlakRay XX-15 lamp (UVP, Inc., San Gabriel, Calif.) at a distance of 10 cm. At this time RP-HPLC showed nearly quantitative removal of the Npe protective group from the α-NH$_2$ group of lysine. 12 µl of 1M NaHCO$_3$ was then added to the mixture, followed by 30 µl of PC-Biotin-NHS (prepared as described in U.S. Pat. No. 5,643,722 to Rothschild et al.). The reaction was incubated at room temperature for 2 hours. The product was isolated using preparative RP-HPLC with a yield of 2.44 O.D.$_{A260}$

EXAMPLE 18

In this example, one method for the expression and purification of amber-suppressor tRNA$^{fMet}$ is provided.

A. Cloning of the *E. coli* Initiator tRNA gene

A 420-base-pair fragment of the nusA *E. coli* gene containing the gene for tRNA-Metf2 (S. Ishi et al., *Proc. Natl. Acad. Sci.*, 81: 409-413 (1984)) was amplified by PCR using the primers 5'-CAC TAC TGC AAG ATT TTA CGT CCG TCT CGG-3'(SEQ ID NO: 1) and 5'-CCA CAA AGC TTC AAA ACC CAG GGC CTC AAC-3'(SEQ ID NO: 2) from *E. coli* genomic DNA introducing PstI and HindIII restriction sites. The PCR fragment was isolated and purified using the QIAquick kit (QIAGEN, Inc., Valencia, Calif.), digested by PstI/HindIII and cloned into PstI/HindIII site of the plasmid pGEM-3 (Promega) to give the plasmid construct pGEM-fmW. The Amber suppressor mutant tRNA-Metf2 gene (A35->U; U36->A) was prepared using the QuickChange method (Stratagene) and primers 5'-GGT AGC TCG TCG GGC TCT AAA CCC GAA GAT CGT CGG-3' (SEQ ID NO: 3) and 5'-CCG ACG ATC TTC GGG TTT AGA GCC CGA CGA GCT A-3' (SEQ ID NO: 4) to give the plasmid pGEM-fmA. Cloning and mutagenesis were verified by dideoxy sequencing procedure according to Sanger et al.

B. Isolation and Purification of Initiator tRNAs

Suppressor tRNA$^{fmet}$ was purified using native PAGE (Seong and RajBhandary, *Proc. Nat'l. Acad. Sci.*, 84: 334-338 (1987)). Briefly, tRNA was isolated from overnight culture (i.e. *E. coli*) using phenol extraction, followed by non-denaturing polyacrylamide gel electrophoresis and "crush and soak" elution into 50 mM sodium acetate buffer pH 5.0, 1% SDS, 2 mM EDTA. (See generally, Sambrook et al., "Molecular Cloning, A Laboratory Manual," (1989)). The tRNA was then subjected to ethanol precipitation. Isolated amber suppressor tRNA$^{fmet}$ appeared as a single band after 8% 7M urea PAGE and ethidium bromide staining.

C. tRNA Truncation by Snake Venom Phosphodiesterase I (SVPDE I)

1.0 O.D.$_{A260}$ of purified initiator suppressor tRNA was dissolved in in 50 µL of a solution of 50 mM Tris-HCl pH 7.5, 10 mM MgCl$_2$ and 100 mM NaCl. To this solution 0.5 unit of SVPDE I was added and the mixture was incubated for 30 min at 0° C. After phenol extraction, the tRNA was precipitated by EtOH, dried, and dissolved in 100 µl of water. Selective (—CA) dinucleotide removal from the 3'-terminus was confirmed by 8%, 7M Urea PAGE analysis.

D. Ligation with BODIPY-Val-pdCpA with Truncated Initiator Suppressor tRNA 0.5 O.D.$_{260}$ of tRNA was incubated overnight at 16° C. with 0.5 O.D.$_{260}$ of BODIPY-Val-pdCpA in 100 µl of ligation buffer (50 mM Tris-HCl pH 7.8; 10 mM MgCl$_2$; 10 mM DTT; 1 mM ATP 30% of DMSO) and 200 units of T4 RNA ligase (New England Biolabs, Beverly, Mass.). After the incubation, the tRNA was precipitated in 3-4 volumes of EtOH, dissolved in 50 µl of water, and spin-filtered using G-25 MicroSpin column (Amersham-Pharmacia Biotech Inc.). The ligated tRNA was aliquoted and stored at −70° C. Additional purification to homogeneity was performed using HPLC (POROS R2M, 4.6×100 mm, buffer A: 0.1 M TEAA pH 6.0, buffer B: 0.05% TFA in acetonitrile, linear gradient 0-50% B at 2 ml/min flow rate). Fractions containing ligated tRNA were pooled, freeze-dried, redissolved in 100 µl water and 10 µl 3M NaOAc, and re-precipitated with 400 µl ethanol.

E. Translation and Analysis

Translation was performed in a cell-free *E. coli* T7 S30 extract (Promega, Madison, Wis.) in 20 µl total volume. The mixture contained 1 µg DNA coding for the particular protein (i.e. α-hemolysin) and initiator amber suppressor tRNA prepared by chemical aminoacylation (1 µg) as described above. The mixture was incubated for 1 hour at 37° C. and 1 µl of the mixture was mixed with the loading buffer (1% SDS, 50 mM Tris pH 8.0, 50% glycerol), heat denatured and run on a 14% SDS-PAGE (150 V, 1 hr) gel. The gel was then rinsed briefly and analyzed using FluorImager in case of BODIPY label. In the case of PC-Biotin, the gel was blotted onto Immobilon PVDF membrane (Millipore) and the biotin detected using streptavidin-HRP (Pierce, Rockford, Ill.).

EXAMPLE 19

In this example, one method for the truncation of total tRNA by venom phosphodiesterase I (SVPDE I) to produce tRNAs (-CA) is provided. Briefly, 10 O.D.$_{A260}$ of total *E. coli* tRNAs (Sigma) was dissolved in 100 µL 50 mM Tris-HCl pH 7.5; 10 mM MgCl$_2$ and 100 mM NaCl and the solution prechilled to 0° C. To this solution, an aliquot of snake venom phosphodiesterase I (Worthington Biochem Cat. No. LS003926, Lakewood, N.J.) was added and the mixture was incubated for 30 min at 0° C. The reaction was terminated by addition of 10 µl of 3M sodium acetate followed by buffered phenol (100 µl, pH 4.3), vortexed, the aqueous layer separated by centrifugation. Aqueous layer was aspirated by pipette, transferred to new tube, and 300 µl of ethanol was added. The solution incubated at −70° C. for 2 hours. The tRNAs were recovered by centrifugation, the pellet dried and re-dissolved in 100 µL of water.

EXAMPLE 20

In this example, one method for the ligation of truncated total tRNA with pdCpA-Lys-BODIPY; Npe is provided. Briefly, 1 O.D.$_{A260}$ unit of tRNA(-CA) was incubated with 0.2 O.D.$_{A260}$ unit of pdCpA-Lys BODIPY; Npe into 100 µl of ligation buffer: 50 mM Tris-HCl pH 7.8; 10 mM MgCl$_2$; 10 mM DTT; 1 nM ATP with 10% of DMSO and 200 units of T4 RNA ligase (New England Biolabs) for 16 hours at 40° C. After incubation tRNA was precipitated by EtOH, dissolved in 50 µl of water and purified on G-25 MicroSpin column (Amersham Pharmacia Biotech Inc.). The ligated tRNA was stored at −20° C.

EXAMPLE 21

In this example, one method for the in vitro translation of α-Hemolysin using total tRNA-Lys-BODIPY; Npe is presented. Typical translation has been done using 10 µL of Promega's S30 T7 *E. coli* translation mixture (Promega Cat. No. L1130) containing 1 µg of alpha Hemolysin plasmid DNA and 1-2 µL of labeled tRNA (0.8-1.6 µg). Before translation, the tRNA solution was placed in a microwell plate and UV irradiated during 5 min using a UVP Black-Ray Lamp model XX-15 to remove the Npe protecting group from alpha amino group of Lys and immediately added to translation mixture. An aliquot 1-3 mL of translation mixture was mixed with 15 µl of SDS loading buffer and applied on 12% SDS Tris-glycin iGel (GradiGels: Gradipore Ltd., French Forest, Australia). Fluorescence was measured using a FluorImager SI (Molecular Dynamics).

EXAMPLE 22

In this example, one method for the expression, purification and analysis of Amber-1 α-Hemolysin (α-PC-Biotin, ε-BODIPY-FL-Lys) is presented. For each 100 µl of translation extract (i.e. Promega's T7 S30 *E. coli* mixture), ~15 µg of initiator suppressor tRNA aminoacylated with α-PC-Biotin, ε-BODIPY-FL-Lys was used. The mixture was incubated for 30 min at 37° C. and diluted to 1 ml by Tris-buffered saline (150 mM NaCl, 10 mM Tris-HCl, pH 7.5) buffer containing 0.1% BSA and 0.1% Tween 20 (buffer A). 15 µl of NeutrAvidin Agarose (30 µl of a 50% of slurry)(Pierce) was added and the suspension was incubated for 30 min at room temperature in the dark with gentle shaking. The resin was washed with buffer A (4×1 mL), resuspended in 50 µl of Buffer A, exposed to UV light (UVP Black-Ray lamp model XX-15) for 10 min, and the eluate collected. The procedure was repeated 3 times and eluates were collected. The eluates were then subjected to SDS-PAGE analysis as follows. 2 µl of crude translation mixture, or 10 µl of diluted translation mixture and wash fractions, and 5 µl of elution fractions aliquots, were subjected to 12% Tris-glycine:SDS-PAGE analysis. The resulting gel was analyzed using a Fluorimager SI.

Finally, the elution fractions were subjected to a α-Hemolysin activity assay as follows. (See Walker et al., *J. Biol. Chem.*, 1992, 267: 10902-10909) 200 µl of Rabbit Red Blood Cells (RRBC) was added to TBS buffer and incubated with 5 µl aliquot of elution fractions for 30 min at room temperature following centrifugation (4000 rpm, 5 minutes). The absorbance of the supernatants at 575 nm was then measured.

EXAMPLE 23

Figure 39:
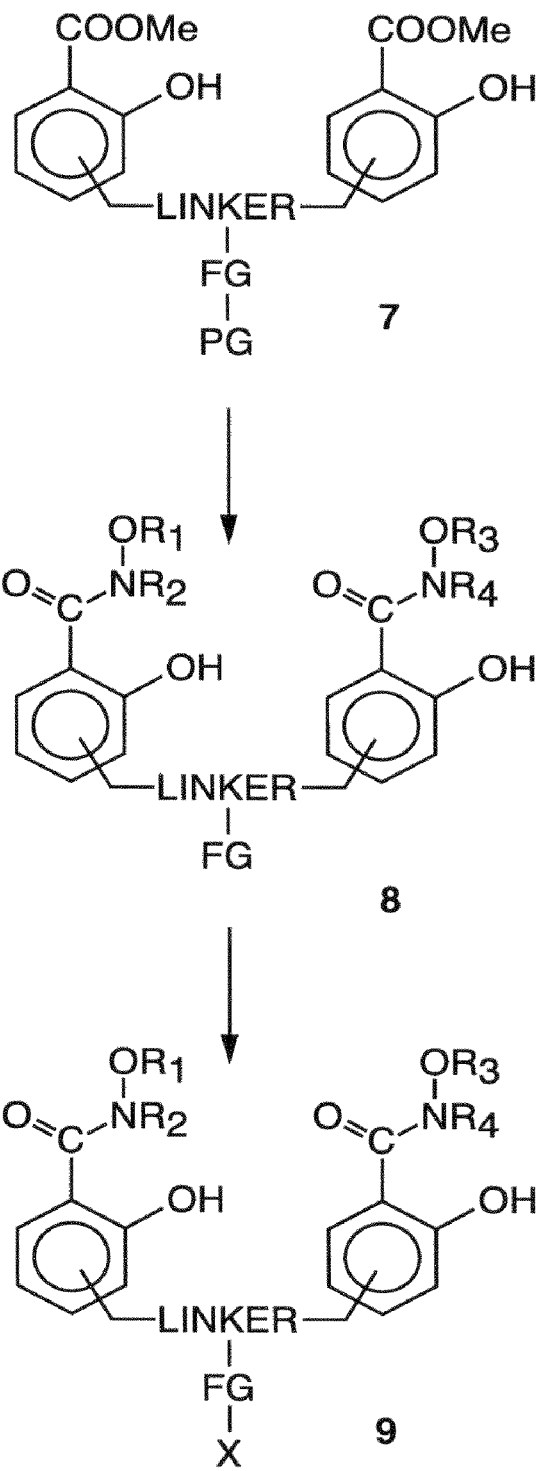
FIG. 39 depicts the general reaction scheme for one embodiment of a method to produce a bis(SHA) conjugate, wherein LINKER is a linker moiety, FG is a functional group, PG is a protective group, groups R1-R4 are either hydrogen or an alkyl group, and X is a group or structure selected from a marker moiety, a bifunctional cross-linker, a polypeptide, a nucleic acid, and a solid support. In one embodiment, X is a polypeptide selected from (but not limited to) alkaline phosphatase, horseradish peroxidase, glutathione transferase, streptavidin, and avidin. In one embodiment, X is a deoxyribonucleic acid. In another embodiment, X is a peptide nucleic acid (PNA). In one particular embodiment, X is a nucleic acid and a corresponding binding partner (e.g. PDBA) is conjugated to a polypeptide. The two conjugates are incubated together and the complex formed has a structure DNA-bis(SHA)-PDBA-Polypeptide. This comprises a method of preparing nucleic acid-polypeptide conjugates. In one embodiment, the PDBA moiety is incorporated into protein via in vitro translation. In another embodiment, the protein is chemically labeled with PDBA reagent.

In this example, one method for the synthesis of a bis(salicylhydroxamic acid) affinity linker with amine handle is provided (as depicted in FIG. 39). Briefly, 4-methylsalicylic acid (compound 1, 5 g, 33 mmol) was added slowly to a chilled solution of concentrated $H_2SO_4$ (4.3 ml, 78 mmol) in 45 ml of methanol. The solution was refluxed for 5 hours, concentrated under reduced pressure, and partitioned between 50 mM $NaHCO_3$ (100 ml) and EtOAc (100 ml). The organic layer was dried with anhydrous $Na_2SO_4$ and the volatiles evaporated under reduced pressure to give methyl 4-methyl salicylate (compound 2) as a colorless oil.

Methyl 4-methyl salicylate (compound 2, 5.52 g, 36 mmol) was dissolved in 56 ml of anhydrous acetic acid. To this solution acetic anhydride (5.57 ml, 144 mmol) was added followed by a catalytic amount of concentrated $H_2SO_4$ (~8 drops or 120 µl). The solution was heated to 70° C. for 20 minutes and then cooled to room temperature. The mixture was partitioned between water (50 ml) and hexane (50 ml), extracted with hexane (4×50 ml), concentrated under reduced pressure, and purified over a silica gel column using a step gradient of hexane/$CH_2Cl_2$/$CHCl_3$ to give 4.36 g of pure 2-OAc-4-Me-salicylic acid methyl ester (compound 3).

2-OAc-4-Me-salicylic acid methyl ester (compound 3, 4 g, 20.8 mmol) was dissolved in $CCl_4$ (25 ml). To this solution was added N-bromosuccinimide (NBS, 3.88 g, 21.8 mmol) and benzoyl peroxide (70 mg, 0.2 mmol). The mixture was refluxed with stirring under argon for 12 hours, solids filtered off, filtrate evaporated under reduced pressure, and purified on a silica gel column using $CH_2Cl_2$ followed by $CHCl_3$ and a step gradient of MeOH in $CHCl_3$ (0-2%) to give 2.34 g of pure 2-OAc-4-bromomethyl-salicylic acid methyl ester (compound 4).

To a solution of hexamethylenetetramine (300 mg, 3.8 mmol) in 15 ml of chlorobenzene (at 50° C.) was added a solution of 2-OAc-4-bromomethyl-salicylic acid methyl ester (compound 4; 1 g, 3.6 mmol) in 2 ml of chlorobenzene. The reaction was heated to 50° C. with stirring and then left overnight at room temperature. The precipitate was filtered off, washed with chlorobenzene (5 ml) and diethyl ether (5 ml), and dried in vacuum to give 850 mg of product as white powder (yield 74%). The resulting hexamethyltetraamonium salt (505 mg, 1.86 mmol) was suspended in 4.8 ml of chlorobenzene. 2.4 ml of methanol was added, followed by 0.6 ml of concentrated HCl. The mixture was stirred at room temperature overnight, 25 ml of cold diethyl ether was added, and the supernatant was removed. The solids were dried under vacuum and used for the next step without purification (4-aminomethyl-salicylic acid methyl ester hydrochloride; compound 5)

Fmoc-Glu(Osu)-O-tBu (Bachem, Torrance, Calif.; 151 mg, 0.29 mmol) was dissolved in DMF (1 ml) and added to a solution of crude 4-aminomethyl-salicylic acid methyl ester hydrochloride (compound 5), followed by the addition of DIPEA (243 µl, 1.39 mmol). The mixture was stirred overnight at room temperature, solvents evaporated and the product (compound 6) isolated using a silica gel column and $CH_2Cl_2$ followed a step gradient of MeOH in $CHCl_3$ (0-10%) with a yield of 40 mg (23%).

Compound 6 (40 mg, 67 µmol) was dissolved in 50% TFA/$CH_2Cl_2$ solution (5 ml) and incubated at room temperature for 15 minutes, then solvents were evaporated and solids re-dissolved and co-evaporated with toluene (5 ml). The material was then dissolved in DMF (0.5 ml) and PyBOP (Novabiochem, 67 µmol, 1 eq.) was added followed by DIPEA (24 µl, 134 µmol, 2 eq.). The solution was stirred at room temperature for 30 minutes and then added to 4-aminomethyl-salicylic acid methyl ester hydrochloride (compound 5, 67 µmol, 1 eq.). An additional 56 µl (321 µmol) of DIPEA was also added and the mixture was stirred overnight at room temperature. The solvents were then removed under reduced pressure and the product (compound 7) was isolated using a silica gel column and a gradient of MeOH in $CHCl_3$ (0-5%) with a yield of 14 mg.

Compound 7 (10 mg, 14 µmoles) was added to a pre-chilled mixture of 11 mg of NaOH (280 µmol, 20 eq.) and hydroxylamine hydrochloride (8 mg, 112 µmol, 8 eq.) in 100 µl of water. The mixture was then placed on a shaker and after 2 hours 20 µl of dioxane was added to improve solubility. The mixture was kept on shaker overnight, then centrifuged for 5 min @16,000 rpm and the supernatant was transferred to a new tube. 1N NaOAc (pH 4.5) was added in portions until the supernatant reached a pH ~4.5. The product was then isolated using preparative HPLC column (NovaPak C18, 10×100 mm, Waters) using a linear gradient (0-90%) of acetonitrile in 50 mM TEAA, pH 4.5 over 45 min at a flow rate of 1 ml/min. Fractions containing the desired product pooled and evaporated to dryness to give 3.6 mg (2.1 µmoles) of compound 8.

It should be noted that while hydroxylamine was employed in this example, other compounds can be substituted (see Table 8).

EXAMPLE 24

This example provides one method for the conjugation of bis(SHA), compound 8, with BODIPY-FL as depicted in FIG. 39. Briefly, to a solution of bis(SHA)(210 mmoles) in 10 µl of 50% ethanol was added 30 µl of 12.5 mM BODIPY-FL solution in DMF, followed by 5 µl of 1N $NaHCO_3$. The mixture was incubated for 1 hour at room temperature and then purified using preparative HPLC (NovaPak C18, 10×100 mm, Waters) using a linear gradient (0-90%) of acetonitrile in 50 mM TEAA (pH 4.5) over a 45 min period at a flow rate of 1 ml/min. Fractions containing the desired product were pooled and evaporated to give 52 nmoles of the target compound 9.

EXAMPLE 25

This example provides one method for the preparation of PDBA-modified sepharose beads. Briefly, 100 mg of 6-aminohexanoic acid N-hydroxysuccinimidyl ester-Sepharose 4B (SIGMA Cat. No. A9019) beads was suspended in 1 ml of water and centrifuged. The beads were washed 2 additional times with 1 ml of water and finally suspended in ~200 µl of water. To this suspension, 50 µl of 2,2'(Ethylenedioxy)bis (ethylamine)(Aldrich Cat. No. 38, 550-6) was added and the suspension was incubated on a shaker for 2 hours. The beads were washed with water until a neutral pH (i.e., 7.0) was obtained, and re-suspended in 200 µl of water. To the 50 µl of this suspension, 10 µl of a 25 mM PDBA-X-NHS solution in DMF was added, followed by 10 µl of 1N $NaHCO_3$. The mixture was incubated on a shaker for 2 hours, and the beads washed with 0.1 N $NaHCO_3$ (5×200 µl) and water until a neutral pH was obtained.

EXAMPLE 26

This example provides one method for the preparation of a PDBA-modified protein (e.g., trypsin inhibitor). Briefly, to a solution of 1 mg of trypsin inhibitor (in 200 µL of water) was added 20 µl (~10 eq.) of 25 mM solution of PDBA-X-NHS (Invitrogen) and 30 µl of 1N $NaHCO_3$. The mixture was incubated at room temperature for 1 hour and purified using a gel filtration column (NAP-5, Pharmacia). The concentration of protein in the eluate (~1 mg/ml) and the label content (~6 labels/protein molecule) was determined using UV-VIS absorbance. Modification of the trypsin inhibitor with BODIPY-FL was performed using same stoichiometry/conditions.

EXAMPLE 27

In this example one embodiment of a PDBA-agarose-bis (SHA)-BODIPY-FL binding experiment and imaging is provided. Briefly, 1 µl of bis(SHA)-BODIPY-FL solution at $5.19 \times 10^{-4}$ M was added to a 10 µl of PDBA-agarose bead suspension (prepared as described in Example 25) in washing/binding buffer (0.1 N $NaHCO_3$ in 10% acetonitrile/water), and the suspension was incubated for 1 hour on a shaker. The beads were washed extensively with washing/binding buffer, and 1 µl of bead suspension was spotted onto a microscope slide. The slide was imaged with either UV transilluminator (365 nm) and a CCD camera (ChemImager, AlphaInnotech)(See, FIG. 48), or a laser scanner (FluorImager SI, Molecular Dynamics)(See, FIG. 49).

EXAMPLE 28

In this example one embodiment of the solution binding of bis(SHA)-BODIPY-FL to a PDBA-modified protein is provided. Briefly, a gel filtration column (4×18 mm) was prepared using Sephadex G-25 (fine) in 50 mM HEPES-Na, pH 7.5. 1 µl of PDBA-modified trypsin inhibitor (~1 µg/µl) was mixed with 1 µl of bis(SHA)-BODIPY-FL ($5.19 \times 10^{-4}$ M) and the volume was adjusted with 50 mM HEPES-Na, pH 7.5 to 10 µl. After the incubation, the sample was loaded onto the Sephadex column and eluted with ~240 µl of the 50 mM HEPES-Na, pH 7.5. Fractions of ~20 µl were collected and fluorescence measured using a fluorescence scanner (FluorImager SI, Molecular Dynamics). A similar experiment was also performed on the bis(SHA)-BODIPY-FL alone, the results of which, are shown in FIG. 50.

EXAMPLE 29

In this example one embodiment of the protein blot detection of unmodified control, BODIPY, and PDBA labeled proteins is provided. Briefly, PVDF membrane (Immobilon, Millipore) was pre-wetted with methanol and ~0.1 µl of protein. As depicted in FIG. 43, Lane 1 was spotted with BODIPY-FL trypsin inhibitor, Lane 2 was spotted with trypsin inhibitor alone, and Lane 3 was spotted with PDBA-trypsin inhibitor. All samples were at a concentration of ~1 µg/µl, and were spotted using pipette. After drying, the membrane was washed with washing/binding buffer (0.1 N $NaHCO_3$ in 10% acetonitrile/water). The membrane was then incubated for 2 hours with a $5.19 \times 10^{-6}$ M solution of BODIPY-FL-bis(SHA) in washing/binding buffer. The membrane was washed again with washing/binding buffer and imaged using reflective UV (254 nm) illumination (See, FIG. 51) and a CCD camera (ChemImager, AlphaInnotech).

EXAMPLE 30

In this example, one embodiment of the in vitro translation and purification of Amber-1 glutathione transferase (GST) labeled with BODIPY-FL-Val or PDBA-X-Lys at the N-terminus is provided. For each 100 µL of translation extract (T7 S30 E. coli, Promega) ~15 µg of initiator suppressor tRNA aminoacylated with either BODIPY-FL-Val or α-Npe, ε-PDBA-Lys was used. The mixture was incubated for 30 min at 37° C., diluted to 1 mL by TBS buffer containing 0.1% BSA and loaded onto Co-NTA column (5×30 mm) equilibrated with the same buffer. The column was washed with loading buffer containing 10 mM imidazole and target protein was eluted using 200 mM imidazole in TBS/BSA buffer. Fractions of ~50 µl were collected and analyzed on gel using Fluorimager or staining with Coomassie Blue for the presence of GST.

EXAMPLE 31

Purified BODIPY-FL labeled GST and PDBA labeled GST (~0.1 µl each) were spotted on a PVDF membrane pre-wetted with methanol. The membrane was allowed to dry and then it was washed with wash/bind buffer (0.1 N $NaHCO_3$ in 10% acetonitrile/water) and SuperBlock PBS (1:1 v/v) for 1 hour. The membrane was imaged using reflective UV (254 nm) illumination and a CCD camera followed by quantitative integration (ChemImager, AlphaInnotech). The membrane was then incubated for 2 hours with a $5.19 \times 10^{-6}$ M solution of BODIPY-FL-bis(SHA) in the same buffer. The membrane was washed again with wash and bind buffer and imaged again as described above. The results of this experiment are presented in FIG. 52. Sample set 1 represents the intensity of the BODIPY-FL and PDBA labeled GST spotted on the membrane. Sample set 2 represents the intensity of the same samples after incubation with BODIPY-FL-bis(SHA).

EXAMPLE 32

Figure 53A:
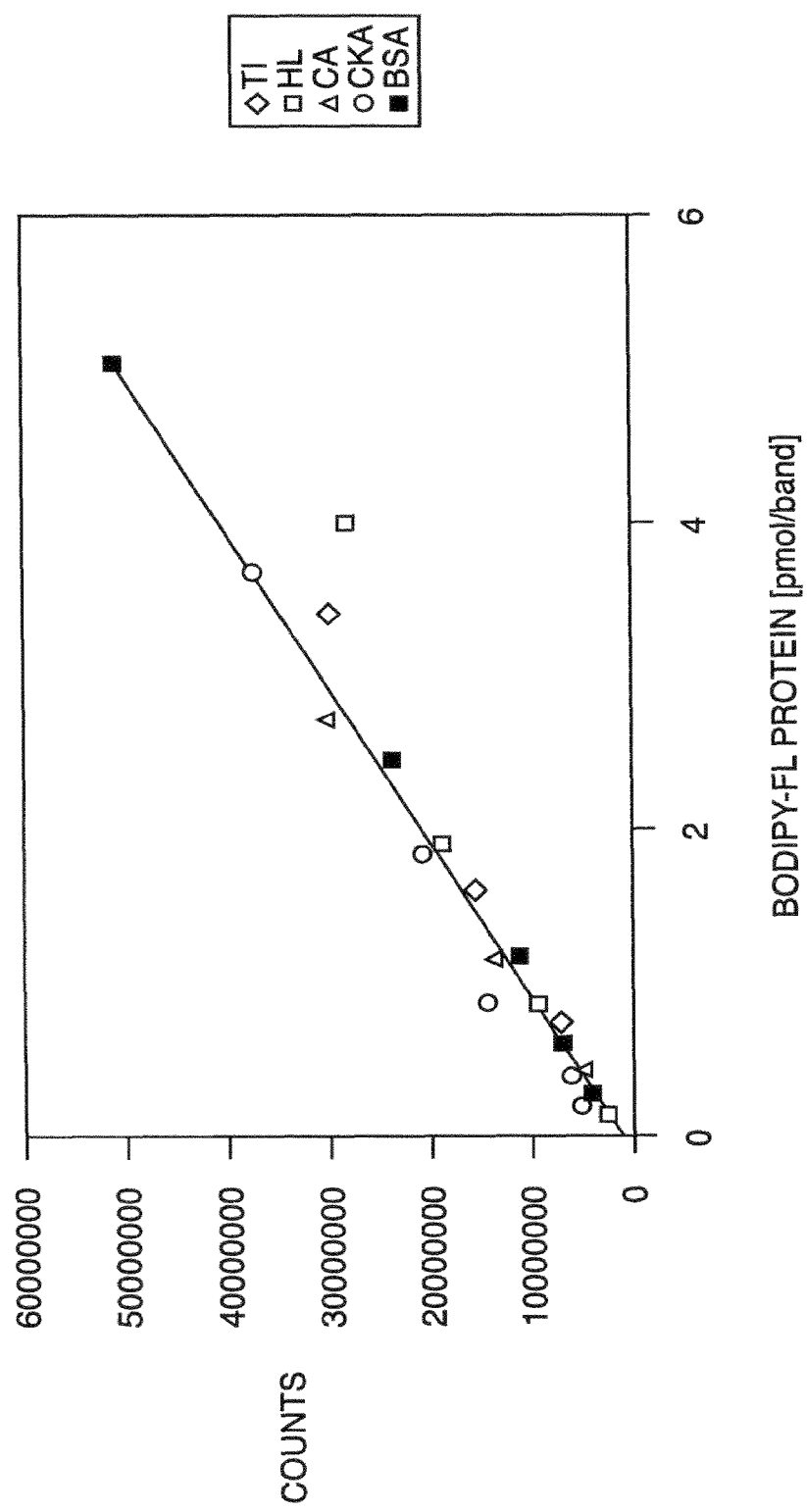
Figure 53B:
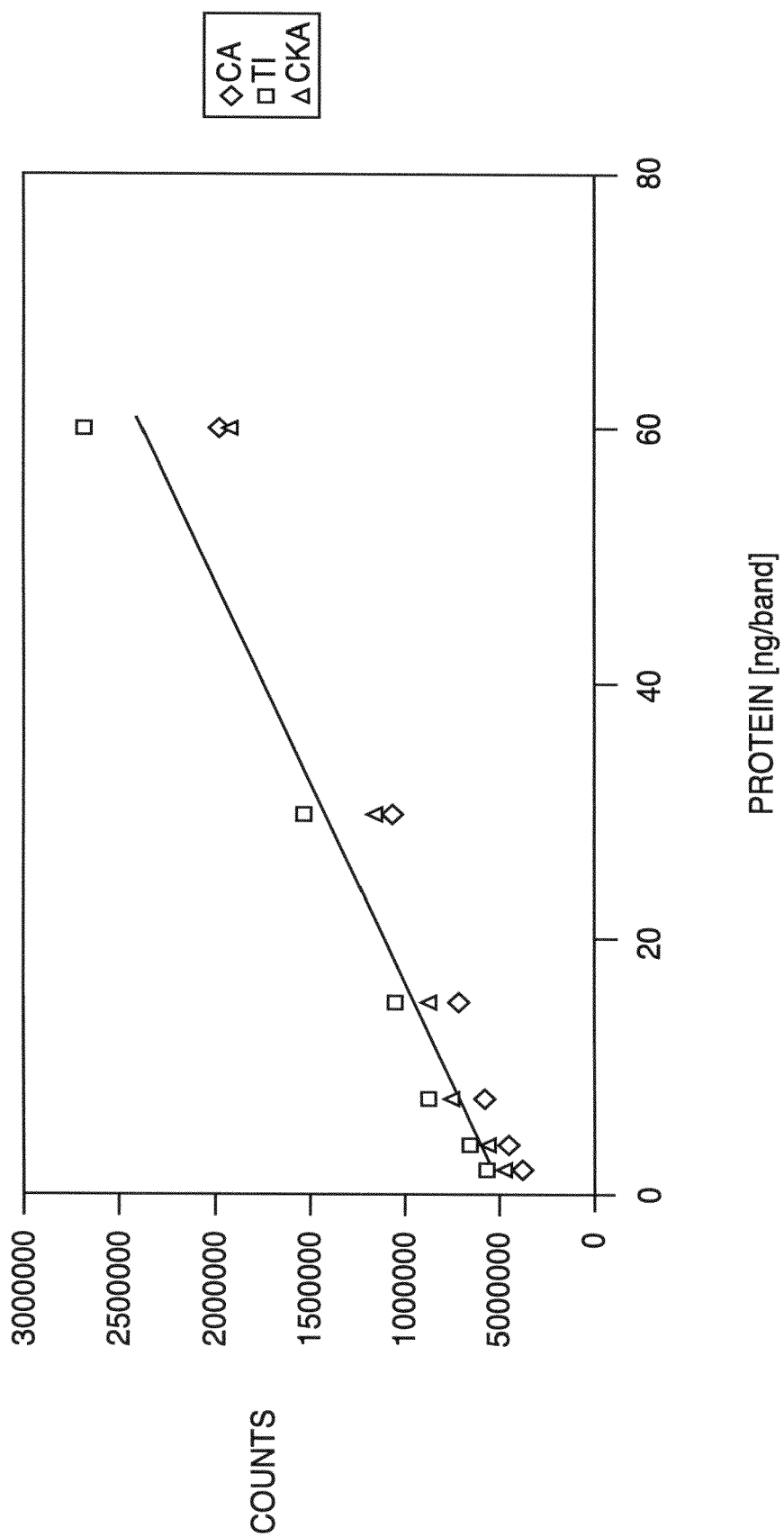

This example describes the determination of specific labeling in the in vitro expressed proteins. For the determination of specific labeling 3 model proteins (trypsin inhibitor, a-hemolysin, carbonic anhydrase) were chemically labeled with BODIPY-FL and purified by gel filtration using NAP-5 columns. The average fluorophore/protein ratio was determined by measuring UV-VIS absorption at 280 and 505 nm. Various amounts of BODIPY-FL labeled proteins were then analyzed by SDS-PAGE and FluorImager (488 nm excitation). The signal intensity was plotted against the amount of BODIPY-FL labeled protein loaded on the gel and served as a calibration curve for the quantitation of the in vitro produced BODIPY-FL labeled proteins (FIG. 53A, 53B). For the determination of total amount of in vitro produced proteins a protein standard mixture (Molecular Probes) was diluted serially (120-7.5 ng/band), separated on 8-16% SDS-PAGE and stained using SYPRO Orange according to the manufacturer instructions and intensity measured using FluoImager (488 nm excitation). The calibration curve was then used for the determination of the total amount of protein produced in an in vitro system. The presence of the BODIPY-FL label on the protein does not interfere with the protein quantitation using the SYPRO Orange stain (data not shown). 3 model 6×His-tagged proteins (hemolysin, calmodulin and glutathione S transferase) were expressed and labeled in E. coli translation system using amber suppressor tRNA aminoacylated with BODIPY-FL-Val. Proteins were purified using Ni-NTA affinity support, separated on the SDS-PAGE and fluorescence quantitated before and after SYPRO Orange staining. The readings were applied to the calibration curves and the amount of protein and fluorophore calculated (FIG. 53C).

EXAMPLE 33

In this example, a method for the preparation of α-Npe, ε-Biotin-X-Lys-pdCpA is provided (where Biotin- X=biotinamidocaproic acid). Briefly, α-Npe, ε-$NH_2$-Lys-pd-CpA (8 O.D.A260, 320 nmol) was dissolved in 100 μl of water and 2 μl of 3M NaOAc, pH 4.5 was added. To this solution a 25 mM solution of Biotin-X-NHS (100 μl; 7.8 eq.)(Pierce) was added followed by 10 μl of 0.5 M HEPES-Na, pH 7.5 and the mixture was incubated at room temperature for 2 hours, after which RP-HPLC showed ~80% conversion into α-Npe, ε-(Biotin-X)-Lys-pdCpA. The product (yield=5 O.D.A260) was isolated using preparative HPLC and characterized by alkaline hydrolysis, irradiation with near UV light, and UV-Vis absorption spectra.

EXAMPLE 34

In this example preparation of total yeast tRNAs aminoacylated with Biotin-X-Lys is described. α-Npe, ε-Biotin-X-Lys-pdCpA (1 OD) was ligated with crude brewers yeast tRNAs (Roche Biochemicals)(20 OD) in 250 μl volume containing 50 μl DMSO, 25 μl of 10×ligation buffer (NEB) and 25 μl of T4 RNA ligase (NEB). The mixture was incubated overnight at 4° C., precipitated by addition of 25 μl of 3M NaOAc followed by 625 μl of EtOH. Pellet was redissolved in 50 μl of water and purified using HPLC (Poros R2H 4.6×100 mm, Perseptive Biosystems) using 0-50% gradient of acetonitrile in 0.1M triethylammonium acetate (TEAA) over 25 minutes and flow rate 2 ml/min. Fractions containing ligated product (~12.5-13.5 min retention time) were pooled, freeze-dried, desalted on a NAP-5 column and concentrated to a final concentration of 0.024 OD/μl. Alternatively, bulk deprotection was carried out by redissolving the crude ligated material in 250 μl of 50 mM NaOAc, pH 4.5 and irradiating for 15 minutes with near UV light source (BlakRay XX-15, UVP Inc.). Irradiation was followed by preparative HPLC (retention time ~10.5 min), desalting and concentration to a final concentration of 0.024 OD/μl. Yield approximately 4-6 OD α-Npe, ε-Biotin-X-Lys-tRNA$^{TOTAL}$, 2-3 OD deprotected and purified α-$NH_2$, ε-Biotin-X-Lys-Lys-tRNA$^{TOTAL}$.

EXAMPLE 35

In this example synthesis of α-Pent-2-enoyl, ε-PC-Biotin-Lys-pdCpA is described. α-Fmoc, ε-$NH_2$-Lys (200 mg, 0.5 mmol) was suspended in 4 ml of DMF and to this suspension 175 μl of N,N'-diisopropylethylamine (DIPEA, 2 eqs.) was added followed by a solution of PC-Biotin-NHS (274 mg, 0.5 mmol, 1 eq.) in 1 ml of DMF. The reaction was stirred overnight at room temperature and partitioned between 0.1 N HCl (50 ml and 50 ml chloroform). The chloroform extract was concentrated under reduced pressure to give 360 mg of a-Fmoc, e-PC-Biotin-Lys. This intermediate was dissolved in 6 ml DMF and to this solution tetramethylguanidine (TMG, 277 μl, 5 eq.) was added. The mixture was incubated 20 minutes at room temperature and acidified with 1N HCl to pH 8.5. Pent-2-enoyl anhydride (90 μl, 0.52 mmol, 1.1 eq.) was then added and the mixture was stirred at room temperature till TLC analysis (9:1:1, chloroform:methanol:acetic acid, v/v) shows complete conversion into a product (about 45 minutes). The mixture was then acidified to pH=2 with 1N HCl and extracted with chloroform (3×30 ml). Extracts were combined, concentrated under reduced pressure and the product purified on small silica gel column using step gradient (0-50%) of methanol in chloroform to give 210 mg (57% yield) of α-Pentenoyl, ε-PC-Biotin-Lys. This product (37 mg) was then dissolved in the mixture of triethylamine (16 μl, 0.116 mmol) and chloroacetonitrile (11 μl, 0.175 mmol) and the mixture incubated overnight, concentrated to dryness and the product α-Pentenoyl, ε-PC-Biotin-Lys-COOCH$_2$CN purified using step gradient of methanol in chloroform (0-12%) on a small silica gel column. Aminoacylation of pdCpA and the purification of product (α-Pentenoyl, ε-PC-Biotin-Lys-pdCpA) was as described in Example 10. Yield was 5 OD of α-Pentenoyl, ε-PC-Biotin-Lys-pdCpA from 10 OD of the starting material pdCpA.

EXAMPLE 36

In this example preparation of total tRNAs aminoacylated with PC-Biotin, its deprotection and purification is described. Total tRNAs from brewers yeast (Roche Biochemicals) was used in these experiments. 5 tubes containing 25 μl of 10×ligation buffer, 50 μl of DMSO, α-Pentenoyl, ε-PC-Biotin-Lys-pdCpA (0.5 OD), total yeast tRNA (10 OD) and 25 μl of T4 RNA ligase (NEB) in a total volume of 250 μl were incubated at 4° C. overnight. The tRNAs were then precipitated by addition of 25 μl of 3M NaOAc pH 4.5 and 625 μl of EtOH. The precipitates were combined (53 OD total) in 120 μl volume and the aliquot was analyzed by HPLC to determine ligation yield (RT unligated 8.25 min, vs 12.1 min ligated material; 23.6% yield). To the solution of tRNAs were added: 3 M NaOAc, pH 4.5 (32 μl) followed by 50 mM solution of I2 in tetrahydrofuran (70 μl). The homogenous solution was then incubated at room temperature for 1 hr and analytical HPLC showed complete conversion of the peak with retention time of 12.1 min to a new peak with retention time of 10.5 min.) The reaction was then precipitated with ethanol and purified using preparative HPLC, fractions containing product pooled, freeze dried, desalted using NAP-5 Sephadex column and concentrated to concentration of 0.024 OD/μl. Total yield of purified and deprotected α-$NH_2$, ε-PC-Biotin-Lys-tRNA$^{TOTAL}$=7.4 OD.

EXAMPLE 37

In this example the evaluation of α-$NH_2$, ε-PC-Biotin-Lys-tRNA$^{TOTAL}$ and α-$NH_2$, ε-Biotin-X-Lys-Lys-tRNA$^{TOTAL}$. is described. For this purpose in vitro translations were performed in rabbit reticulocyte extract (TNT T7 Coupled Reticulocyte Lysate, Promega Corp., Madison, Wis.) utilizing epitope tagged protein template and the tRNAs. The protein template was human p53 protein cloned into pET expression vector (Novagen, Madison, Wis.) containing HSV epitope. Briefly a mixture containing 10 μl of reticulocyte extract, 0.5 μl of DNA template (@ 0.5-1.0 ug/μl) and 0.5 μl of either α-$NH_2$, ε-PC-Biotin-Lys-tRNA$^{TOTAL}$, ε-Biotin-X-Lys-Lys-tRNATOTAL or Biotin-X-Lys-tRNA$^{Lys}$ (tRNA$^{scend}$, Promega Corp, Madison, Wis.) was prepared and incubated at 30° C. for 1 hr. The translation products were analyzed using ELISA and/or Western blots.

EXAMPLE 38

This example describes the detection of biotin and PC-Biotin incorporation into in vitro produced proteins using ELISA. To a 96-well opaque polystyrene plate was added capture protein. Anti-HSV antibody (Novagen, Madison, Wis.) was used at a concentration of 1.5 μl/100 μl of 100 mM carbonate buffer, pH 9.5. The plate was incubated at room temperature for 45 minutes on a platform shaker, was washed with TBST buffer (50 mM tris, pH 7.5, 200 mM NaCl, 0.05% Tween-20)(5×300 μL) and wells were next blocked by addition of 300 μl 5% BSA in TBST and 30 min. incubation. Translation mixture (10 μl was diluted to 400 μl with 5% BSA in TBST and 200 μl of the diluted translation mixture was added to the first well. This sample was serially diluted with 5% BSA in TBST and then samples were incubated at room temperature on a shaker for 45 minutes. Wells were washed with TBST buffer (5×300 µl) and blocked with 5% BSA in TBST. Streptavidin-alkaline phosphatase (Pierce) at 1:25,000 dilution (200 µl/well) was added, and wells were incubated at room temperature on a shaker for 45 minutes, washed with TBST (5×300 µl) and TBS (2×300 µl) and an AP substrate (Roche Biochemicals, BM Chemiluminescence ELISA Substrate) with a dilution of 1:500, incubated for 10 minutes and the wells read using luminometer (Lumicount, Packard Biosciences).

Alternatively, ELISA assays were performed under denaturing conditions where 4 µl of translation was added mixed with 4 µl of 10% SDS, 20 mM EDTA solution, boiled for 5 minutes and diluted 50-fold with 5% BSA in TBST prior to assay.

Alternatively, plates are coated with Neutravidin (Pierce) at a concentration of 10 ug/200 µl of carbonate buffer. Detection of HSV epitope was performed with anti-HSV-AP diluted 1:500 followed by wash and development with chemiluminescent substrate.

EXAMPLE 39

In this example the detection of incorporated Biotin or PC-Biotin into proteins during in vitro translation with tRNA-TOTAL by means of Western blot will be described. 1 µl of crude translation mixture was denatured by boiling in 1% SDS/50 mM Tris pH 6.8 for 5 minutes. The mixture was then separated on a 8-16% SDS gradient gel (100 V, 1 hr) and transferred to PVDF membrane (Immobilon, Millipore) using electroblotter (110 v, 1 hr) and transfer buffer (6 mM Tris, 48 mM glycine, 0.005% SDS) The membrane was then blocked 1% BSA/TBST for 1 hr and then a solution of anti-HSV-AP (diluted 1:1,000) or streptavidin-AP (diluted 1:10,000) was added and the membrane was incubated at 37° C. for 1 hour on a platform shaker. The membrane was washed with TBST (2×30 s, 4×5 min) and TBS (2×30 sec). ECF substrate solution (Amersham Biosciences) was then added and membrane incubated face down for 5 min at room temperature after which membrane was imaged using FluorImager (488 nm excitation, 530 nm emission).

TABLE 2

Amine to Amine Homobifunctional Crosslinkers

| Acronym | PrdNum | Spacer Arm Length | Links | Cleavable By | Water Soluble | Membrane Permeable |
|---|---|---|---|---|---|---|
| BS$^3$ | 21580 | 11.4 Å | Amines To Amines | non | Yes | No |
| DSS | 21555 | 11.4 Å | Amines To Amines | non | No | Yes |
| DMS | 20700 | 11.0 Å | Amines To Amines | non | Yes | Yes |
| DMP | 21666 | 9.1999998 Å | Amines To Amines | non | Yes | Yes |
| DMA | 20663 | 8.6000004 Å | Amines To Amines | non | Yes | Yes |
| DSG | 20593 | 7.6999998 Å | Amines To Amines | non | No | Yes |
| MSA | 22605 | 7.1999998 Å | Amines To Amines | non | No | nd |
| DFDNB | 21525 | 3.0 Å | Amines To Amines | non | No | Yes |

TABLE 3

Amine to Sulfhydryl Heterobifunctional Crosslinkers

| Acronym | PrdNum | Spacer Arm Length | Links | Cleavable By | Water Soluble | Membrane Permeable |
|---|---|---|---|---|---|---|
| Sulfo-KMUS | 21111 | 19.5 Å | Amines To Sulfhydryls | non | Yes | No |
| LC-SMCC | 22362 | 16.1 Å | Amines To Sulfhydryls | non | No | Yes |
| KMUA | 22211 | 15.7 Å | Amines To Sulfhydryls | non | No | nd |
| Sulfo-SMPB | 22317 | 14.5 Å | Amines To Sulfhydryls | non | Yes | No |
| SMPB | 22416 | 14.5 Å | Amines To Sulfhydryls | non | No | Yes |
| SMPH | 22363 | 14.3 Å | Amines To Sulfhydryls | non | No | nd |
| SMCC | 22360 | 11.6 Å | Amines To Sulfhydryls | non | No | Yes |
| Sulfo-SMCC | 22322 | 11.6 Å | Amines To Sulfhydryls | non | Yes | No |
| SIAB | 22329 | 10.6 Å | Amines To Sulfhydryls | non | No | Yes |
| Sulfo-SIAB | 22327 | 10.6 Å | Amines To Sulfhydryls | non | Yes | No |
| Sulfo-GMBS | 22324 | 10.2 Å | Amines To Sulfhydryls | non | Yes | No |
| GMBS | 22309 | 10.2 Å | Amines To Sulfhydryls | non | No | Yes |
| MBS | 22311 | 9.8999996 Å | Amines To Sulfhydryls | non | No | Yes |
| Sulfo-MBS | 22312 | 9.8999996 Å | Amines To Sulfhydryls | non | Yes | No |
| EMCA | 22306 | 9.3999996 Å | Amines To Sulfhydryls | non | Yes | No |
| EMCS | 22308 | 9.3999996 Å | Amines To Sulfhydryls | non | No | Yes |
| Sulfo-EMCS | 22307 | 9.3999996 Å | Amines To Sulfhydryls | non | Yes | No |
| SVSB | 22358 | 8.3000002 Å | Amines To Sulfhydryls | non | No | Yes |
| BMPS | 22298 | 6.9000001 Å | Amines To Sulfhydryls | non | No | nd |
| SBAP | 22339 | 6.1999998 Å | Amines To Sulfhydryls | non | No | Yes |

TABLE 3-continued

Amine to Sulfhydryl Heterobifunctional Crosslinkers

| Acronym | PrdNum | Spacer Arm Length | Links | Cleavable By | Water Soluble | Membrane Permeable |
|---|---|---|---|---|---|---|
| BMPA | 22296 | 5.9000001 Å | Amines To Sulfhydryls | non | Yes | No |
| AMAS | 22295 | 4.4000001 Å | Amines To Sulfhydryls | non | No | nd |
| SATP | 26100 | 4.09999 Å | Amines To Sulfhydryls | non | No | Yes |
| SIA | 22349 | 1.5 Å | Amines To Sulfhydryls | non | No | nd |

TABLE 4

Amine to Nonselective Heterobifunctional Crosslinkers

| Acronym | PrdNum | Spacer Arm Length | Links | Cleavable By | Water Soluble | Membrane Permeable |
|---|---|---|---|---|---|---|
| SANPAH | 22600 | 18.200001 Å | Amines To Nonselective | non | No | Yes |
| Sulfo-SANPAH | 22589 | 18.200001 Å | Amines To Nonselective | non | Yes | No |
| sulfo-NHS-LC-ASA | 27735 | 18.0 Å | Amines To Nonselective | non | Yes | No |
| Sulfo-HSAB | 21563 | 9.0 Å | Amines To Nonselective | non | Yes | No |
| NHS-ASA | 27714 | 8.0 Å | Amines To Nonselective | non | No | Yes |
| ANB-NOS | 21451 | 7.6999998 Å | Amines To Nonselective | non | No | No |
| TFCS | 22299 | 7.6999998 Å | Amines To Nonselective | non | Yes | nd |
| SPB(NHS-Psoralen) | 23013 | Å | Amines To Nonselective | non | No | Yes |

TABLE 5

$$HOOC-CH_2-CH(NH_2)-CH_2-COOH$$

$$HOOC-CH(NH_2)-COOH$$

$$HOOC-(CH_2)_2-CH(NH_2)-CH_2-COOH$$

$$HOOC-CH_2-CH(NH_2)-COOH$$

$$HOOC-(CH_2)_2-CH(NH_2)-(CH_2)_2-COOH$$

$$HOOC-(CH_2)_2-CH(NH_2)-COOH$$

$$HOOC-(CH_2)_3-CH(NH_2)-COOH$$

TABLE 6a

| Linker general formula | Examples | Activators (Examples) |
|---|---|---|
| NHS—O—C(=O)-LINKER-C(=O)—O-PG2, with FG and PG1 substituents | Fmoc-Asp(OtBu)OSu (Bachem B-1075): NHS—OOC—CH_2—CH(Fmoc-HN)—COOtBu | DCC (N,N'-Dicyclohexylcarbodiimide) CDI (1,1'-Carbonyldimidazole) DSC (N,N'-Disuccinimidyl carbonate) PyBOP (Benzotriazole-1-yl-oxy-tris-pyrrolidino-phosphonium hexafluorophosphate) |

TABLE 6a-continued

| Linker general formula | Examples | Activators (Examples) |
| --- | --- | --- |
| | Fmoc-Asp(OtBu)OPfp (Bachem B-1110)<br>Pfp-OOC—CH$_2$—CH—COOtBu<br>$\|$<br>Fmoc-HN | PyBroP (Bromo-tris-pyrrolidino-phosphonium hexafluorophosphate)<br>EDC (1-Ethyl-3-(3'-dimethylamino-propyl)carbodiimide•HCl) |
| | Fmoc-Asp(OtBu)OSu (Bachem B-2310)<br>NHS—OOC—CH$_2$CH$_2$—CH—COOtBu<br>$\|$<br>Fmoc-HN | |

TABLE 6b

| Linker general formula | Examples | Activators (Examples) |
| --- | --- | --- |
| HO—C(=O)-LINKER-C(=O)—OH<br>$\|$<br>FG<br>$\|$<br>PG | 2-aminomalonic acid<br>HO—C(=O)—CH—C(=O)—OH<br>$\|$<br>NH-PG | DCC (N,N'-Dicyclohexylcarbodiimide)<br>CDI (1,1'-Carbonyldimidazole)<br>DSC (N,N'-Disuccinimidyl carbonate)<br>PyBOP (Benzotriazole-1-yl-oxy-tris-pyrrolidino-phosphonium hexafluorophosphate) |
| | 3-aminoglutaric acid<br>HO—C(=O)—CH$_2$—CH—CH$_2$—C(=O)—OH<br>$\|$<br>NH-PG | PyBroP (Bromo-tris-pyrrolidino-phosphonium hexafluorophosphate)<br>EDC (1-Ethyl-3-(3'-dimethylamino-propyl)carbodiimide•HCl) |
| | Glutamic acid<br>HO—C(=O)—CH$_2$—CH$_2$—CH—C(=O)—OH<br>$\|$<br>NH-PG | |
| | 1-amino, 1,6-hexanedicarboxylic acid<br>HO—C(=O)—CH$_2$—CH$_2$—CH$_2$—CH—C(=O)—OH<br>$\|$<br>NH-PG | |
| | 4-amino, 1,7-heptanedicarboxylic acid<br>HO—C(=O)—CH$_2$—CH$_2$—CH—CH$_2$—CH$_2$—C<br>$\|$<br>NH-PG | |

TABLE 7

N-hydroxysuccinimidyl and N-hydroxysulfosuccinimidyl Active Esters (amine reactive)

| Cat # | Product Name | Unit Size |
| --- | --- | --- |
| A-2522 | 4-azido-2,3,5,6-tetrafluorobenzoic acid, succinimidyl ester (ATFB, SE) | 25 mg |
| A-2952 | 3-amino-3-deoxydigoxigenin hemisuccinamide, succinimidyl ester | 5 mg |
| A-6118 | 6-((7-amino-4-methylcoumarin-3-acetyl)amino)hexanoic acid, succinimidyl ester (AMCA-X, SE) | 10 mg |

TABLE 7-continued

N-hydroxysuccinimidyl and N-hydroxysulfosuccinimidyl Active Esters (amine reactive)

| Cat # | Product Name | Unit Size |
|---|---|---|
| A-10168 | Alexa Fluor ® 350 carboxylic acid, succinimidyl ester | 5 mg |
| A-10169 | Alexa Fluor ® 430 carboxylic acid, succinimidyl ester | 5 mg |
| A-20000 | Alexa Fluor ® 488 carboxylic acid, succinimidyl ester | 1 mg |
| A-20001 | Alexa Fluor ® 532 carboxylic acid, succinimidyl ester | 1 mg |
| A-20002 | Alexa Fluor ® 546 carboxylic acid, succinimidyl ester | 1 mg |
| A-20003 | Alexa Fluor ® 568 carboxylic acid, succinimidyl ester | 1 mg |
| A-20004 | Alexa Fluor ® 594 carboxylic acid, succinimidyl ester | 1 mg |
| A-20005 | Alexa Fluor ® 633 carboxylic acid, succinimidyl ester | 1 mg |
| A-20006 | Alexa Fluor ® 647 carboxylic acid, succinimidyl ester | 1 mg |
| A-20007 | Alexa Fluor ® 660 carboxylic acid, succinimidyl ester | 1 mg |
| A-20008 | Alexa Fluor ® 680 carboxylic acid, succinimidyl ester | 1 mg |
| A-20009 | Alexa Fluor ® 555 carboxylic acid, succinimidyl ester | 1 mg |
| A-20010 | Alexa Fluor ® 700 carboxylic acid, succinimidyl ester | 1 mg |
| A-20011 | Alexa Fluor ® 750 carboxylic acid, succinimidyl ester | 1 mg |
| A-20770 | 6-((acryloyl)amino)hexanoic acid, succinimidyl ester (acryloyl-X, SE) | 5 mg |
| B-1513 | D-biotin, succinimidyl ester (succinimidyl D-biotin) | 100 mg |
| B-1577 | 4-benzoylbenzoic acid, succinimidyl ester | 100 mg |
| B-1582 | 6-((biotinoyl)amino)hexanoic acid, succinimidyl ester (biotin-X, SE; biotinamidocaproate, N-hydroxysuccinimidyl ester) | 100 mg |
| B-1606 | 6-((6-((biotinoyl)amino)hexanoyl)amino)hexanoic acid, succinimidyl ester (biotin-XX, SE) | 100 mg |
| B-2603 | 12-((biotinoyl)amino)dodecanoic acid, succinimidyl ester | 25 mg |
| B-2604 | biotin-X 2,4-dinitrophenyl-X-L-lysine, succinimidyl ester (DNP-X-biocytin-X, SE) | 5 mg |
| B-6352 | 6-((6-((biotinoyl)amino)hexanoyl)amino)hexanoic acid, sulfosuccinimidyl ester, sodium salt (biotin-XX, SSE) | 25 mg |
| B-6353 | 6-((biotinoyl)amino)hexanoic acid, sulfosuccinimidyl ester, sodium salt (Sulfo-NHS-LC-Biotin; biotin-X, SSE) | 25 mg |
| B-10622 | bis-(4-carboxypiperidinyl)sulfonerhodamine, di(succinimidyl ester) | 5 mg |
| C-653 | 5-(and-6)-carboxynaphthofluorescein, succinimidyl ester *mixed isomers* | 25 mg |
| C-1157 | 5-(and-6)-carboxyfluorescein diacetate, succinimidyl ester (5(6)-CFDA, SE; CFSE) *mixed isomers* | 25 mg |
| C-1165 | 5-(and-6)-carboxy-2',7'-dichlorofluorescein diacetate, succinimidyl ester *mixed isomers* | 25 mg |
| C-1171 | 5-(and-6)-carboxytetramethylrhodamine, succinimidyl ester (5(6)-TAMRA, SE) *mixed isomers* | 25 mg |
| C-1309 | 5-(and-6)-carboxy-X-rhodamine, succinimidyl ester (5(6)-ROX, SE) *mixed isomers* | 25 mg |
| C-1311 | 5-(and-6)-carboxyfluorescein, succinimidyl ester (5(6)-FAM, SE) *mixed isomers* | 100 mg |
| C-2210 | 5-carboxyfluorescein, succinimidyl ester (5-FAM, SE) *single isomer* | 10 mg |
| C-2211 | 5-carboxytetramethylrhodamine, succinimidyl ester (5-TAMRA, SE) *single isomer* | 5 mg |
| C-3061 | 5-(and-6)-carboxy SNAFL ®-1, succinimidyl ester *mixed isomers* | 1 mg |
| C-3062 | 5-(and-6)-carboxy SNAFL ®-2, succinimidyl ester *mixed isomers* | 1 mg |
| C-6123 | 6-carboxytetramethylrhodamine, succinimidyl ester (6-TAMRA, SE) *single isomer* | 5 mg |
| C-6125 | 5-carboxy-X-rhodamine, succinimidyl ester (5-ROX, SE) *single isomer* | 5 mg |
| C-6126 | 6-carboxy-X-rhodamine, succinimidyl ester (6-ROX, SE) *single isomer* | 5 mg |
| C-6127 | 5-carboxyrhodamine 6G, succinimidyl ester (5-CR 6G, SE) *single isomer* | 5 mg |
| C-6128 | 6-carboxyrhodamine 6G, succinimidyl ester (6-CR 6G, SE) *single isomer* | 5 mg |
| C-6157 | 5-(and-6)-carboxyrhodamine 6G, succinimidyl ester (5(6)-CR 6G, SE) *mixed isomers* | 5 mg |
| C-6164 | 6-carboxyfluorescein, succinimidyl ester (6-FAM, SE) *single isomer* | 10 mg |
| C-6166 | 5-carboxy-2',4',5',7'-tetrabromosulfonefluorescein, succinimidyl ester, bis-(diisopropylethylammonium) salt | 5 mg |
| C-6171 | 6-carboxy-4',5'-dichloro-2',7'-dimethoxyfluorescein, succinimidyl ester (6-JOE, SE) | 5 mg |
| C-7933 | coumarin-3-carboxylic acid, succinimidyl ester (SECCA) | 25 mg |
| C-10164 | Cascade Yellow ™ succinimidyl ester | 5 mg |
| C-20050 | 5-carboxyfluorescein-bis-(5-carboxymethoxy-2-nitrobenzyl) ether, β-alanine-carboxamide, succinimidyl ester (CMNB-caged carboxyfluorescein, SE) | 1 mg |

TABLE 7-continued

N-hydroxysuccinimidyl and N-hydroxysulfosuccinimidyl Active Esters (amine reactive)

| Cat # | Product Name | Unit Size |
|---|---|---|
| C-22803 | 5-(and-6)-carboxyeosin diacetate, succinimidyl ester *mixed isomers* | 5 mg |
| D-374 | 7-dimethylaminocoumarin-4-acetic acid, succinimidyl ester (DMACA, SE) | 25 mg |
| D-1412 | 7-diethylaminocoumarin-3-carboxylic acid, succinimidyl ester | 25 mg |
| D-2184 | 4,4-difluoro-5,7-dimethyl-4-bora-3a,4a-diaza-s-indacene-3-propionic acid, succinimidyl ester (BODIPY ® FL, SE) | 5 mg |
| D-2187 | 4,4-difluoro-5,7-diphenyl-4-bora-3a,4a-diaza-s-indacene-3-propionic acid, succinimidyl ester (BODIPY ® 530/550, SE) | 5 mg |
| D-2191 | 4,4-difluoro-1,3,5,7-tetramethyl-4-bora-3a,4a-diaza-s-indacene-8-propionic acid, succinimidyl ester (BODIPY ® 493/503, SE) | 5 mg |
| D-2219 | 4,4-difluoro-5-(2-thienyl)-4-bora-3a,4a-diaza-s-indacene-3-propionic acid, succinimidyl ester (BODIPY ® 558/568, SE) | 5 mg |
| D-2222 | 4,4-difluoro-5-styryl-4-bora-3a,4a-diaza-s-indacene-3-propionic acid, succinimidyl ester (BODIPY ® 564/570, SE) | 5 mg |
| D-2225 | 4,4-difluoro-5-(2-pyrrolyl)-4-bora-3a,4a-diaza-s-indacene-3-propionic acid, succinimidyl ester (BODIPY ® 576/589, SE) | 5 mg |
| D-2228 | 4,4-difluoro-5-(4-phenyl-1,3-butadienyl)-4-bora-3a,4a-diaza-s-indacene-3-propionic acid, succinimidyl ester (BODIPY ® 581/591, SE) | 5 mg |
| D-2245 | 4-((4-(dimethylamino)phenyl)azo)benzoic acid, succinimidyl ester (dabcyl, SE) | 100 mg |
| D-2248 | 6-(2,4-dinitrophenyl)aminohexanoic acid, succinimidyl ester (DNP-X, SE) | 25 mg |
| D-2935 | 2',7'-dichlorodihydrofluorescein diacetate, succinimidyl ester (OxyBURST ® Green H$_2$DCFDA, SE) | 5 mg |
| D-6102 | 6-((4,4-difluoro-5,7-dimethyl-4-bora-3a,4a-diaza-s-indacene-3-propionyl)amino)hexanoic acid, succinimidyl ester (BODIPY ® FL-X, SE) | 5 mg |
| D-6104 | 6-((5-dimethylaminonaphthalene-1-sulfonyl)amino)hexanoic acid, succinimidyl ester (dansyl-X, SE) | 25 mg |
| D-6116 | 6-(((4-(4,4-difluoro-5-(2-thienyl)-4-bora-3a,4a-diaza-s-indacene-3-yl)phenoxy)acetyl)amino)hexanoic acid, succinimidyl ester (BODIPY ® TR-X, SE) | 5 mg |
| D-6117 | 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY ® TMR-X, SE) | 5 mg |
| D-6140 | 4,4-difluoro-5,7-dimethyl-4-bora-3a,4a-diaza-s-indacene-3-propionic acid, sulfosuccinimidyl ester, sodium salt (BODIPY ® FL, SSE) | 5 mg |
| D-6141 | N-(4,4-difluoro-5,7-dimethyl-4-bora-3a,4a-diaza-s-indacene-3-propionyl)cysteic acid, succinimidyl ester, triethylammonium salt (BODIPY ® FL, CASE) | 5 mg |
| D-6144 | 2,6-dibromo-4,4-difluoro-5,7-dimethyl-4-bora-3a,4a-diaza-s-indacene-3-propionic acid, succinimidyl ester (BODIPY ® FL Br$_2$, SE) | 5 mg |
| D-6180 | 4,4-difluoro-5-phenyl-4-bora-3a,4a-diaza-s-indacene-3-propionic acid, succinimidyl ester (BODIPY ® R6G, SE) | 5 mg |
| D-6184 | 4,4-difluoro-5,7-dimethyl-4-bora-3a,4a-diaza-s-indacene-3-pentanoic acid, succinimidyl ester (BODIPY ® FL C$_5$, SE) | 5 mg |
| D-6186 | 6-((4,4-difluoro-5-phenyl-4-bora-3a,4a-diaza-s-indacene-3-propionyl)amino)hexanoic acid, succinimidyl ester (BODIPY ® R6G-X, SE) | 5 mg |
| D-10000 | 6-(((4,4-difluoro-5-(2-thienyl)-4-bora-3a,4a-diaza-s-indacene-3-yl)styryloxy)acetyl)aminohexanoic acid, succinimidyl ester (BODIPY ® 630/650-X, SE) | 5 mg |
| D-10001 | 6-(((4,4-difluoro-5-(2-pyrrolyl)-4-bora-3a,4a-diaza-s-indacene-3-yl)styryloxy)acetyl)aminohexanoic acid, succinimidyl ester (BODIPY ® 650/665-X, SE) | 5 mg |
| D-10161 | Dapoxyl ® carboxylic acid, succinimidyl ester | 5 mg |
| D-10162 | Dapoxyl ® 3-sulfonamidopropionic acid, succinimidyl ester | 10 mg |
| D-20092 | 2',7'-dichloro-6-carboxy-4,7-dichlorofluorescein, succinimidyl ester (6-TET, SE) *single isomer* | 5 mg |
| F-2181 | 6-(fluorescein-5-(and-6)-carboxamido)hexanoic acid, succinimidyl ester (5(6)-SFX) *mixed isomers* | 10 mg |
| F-6106 | 6-(fluorescein-5-carboxamido)hexanoic acid, succinimidyl | 5 mg |

TABLE 8

| Chemical name | Source | Structure |
|---|---|---|
| Hydroxylamine hydrochloride | SIGMA H9876 | $H_2N-O-H \times HCl$ |
| Methoxylamine hydrochloride | Aldrich 226904 | $H_2N-O-CH_3 \times HCl$ |
| N-Methylhydroxylamine hydrochloride | Aldrich M5,040-0 | $CH_3-NH-OH \times HCl$ |

We claim:

1. A composition having the formula:

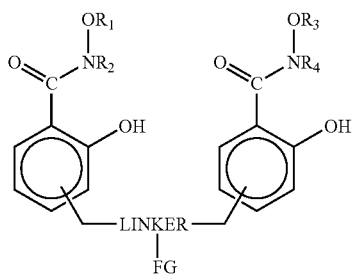

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, and LINKER is a chain comprising at least three carbon atoms.

2. The composition of claim 1, wherein said functional group is an amino group.

3. A composition having the formula:

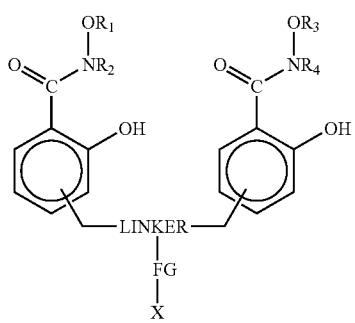

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, LINKER is a chain comprising at least three carbon atoms, and X is selected from the group consisting of a solid support, a detectable marker, and a biomolecule.

4. The composition of claim 3, wherein said functional group is an amino group.

5. The composition of claim 3, wherein said detectable marker is a fluorescent marker.

6. A composition having the formula:

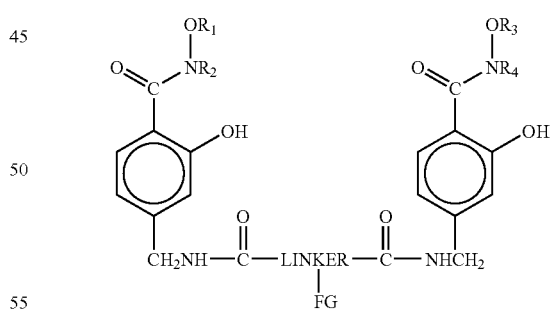

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, and LINKER is a chain comprising at least one carbon atom.

7. The composition of claim 6, wherein said functional group is an amino group.

8. A composition having the formula:

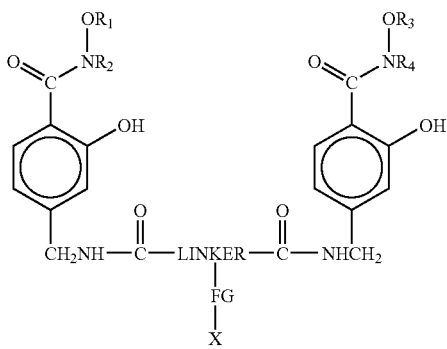

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, FG is a functional group, LINKER is a chain comprising at least one carbon atom, and X is selected from the group consisting of a solid support, a detectable marker, and a biomolecule.

9. The composition of claim 8, wherein said functional group is an amino group.

10. The composition of claim 8, wherein said detectable marker is a fluorescent marker.

11. A composition having the formula:

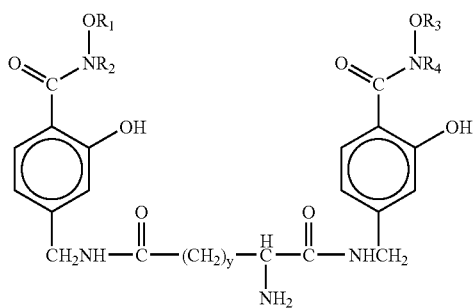

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, and y is an integer between 0 and 6.

12. The composition of claim 11, wherein said functional group is an amino group.

13. A composition having the formula:

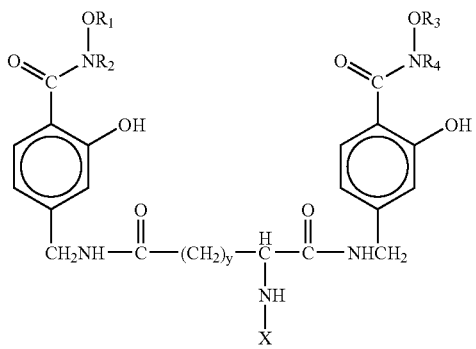

wherein $R_1$ is hydrogen or a lower alkyl group, $R_2$ is hydrogen or a lower alkyl group, $R_3$ is hydrogen or a lower alkyl group, $R_4$ is hydrogen or a lower alkyl group, y is an integer between 0 and 6, and X is selected from the group consisting of a solid support, a detectable marker, and a protein.

14. The composition of claim 13, wherein said functional group is an amino group.

15. The composition of claim 13, wherein said detectable marker is a fluorescent marker.

* * * * *

SEQUENCE LISTING

```
<160> NUMBER OF SEQ ID NOS: 7

<210> SEQ ID NO 1
<211> LENGTH: 30
<212> TYPE: DNA
<213> ORGANISM: Artificial Sequences
<220> FEATURE:
<223> OTHER INFORMATION: Synthetic

<400> SEQUENCE: 1
cactactgca agattttacg tccgtctcgg                                  30

<210> SEQ ID NO 2
<211> LENGTH: 30
<212> TYPE: DNA
<213> ORGANISM: Artificial Sequences
<220> FEATURE:
<223> OTHER INFORMATION: Synthetic

<400> SEQUENCE: 2
ccacaaagct tcaaacccca gggcctcaac                                  30

<210> SEQ ID NO 3
<211> LENGTH: 36
<212> TYPE: DNA
<213> ORGANISM: Artificial Sequences
<220> FEATURE:
<223> OTHER INFORMATION: Synthetic

<400> SEQUENCE: 3
ggtagctcgt cgggctctaa acccgaagat cgtcgg                           36

<210> SEQ ID NO 4
<211> LENGTH: 34
<212> TYPE: DNA
<213> ORGANISM: Artificial Sequences
<220> FEATURE:
<223> OTHER INFORMATION: Synthetic

<400> SEQUENCE: 4
ccgacgatct tcgggtttag agcccgacga gcta                             34

<210> SEQ ID NO 5
<211> LENGTH: 33
<212> TYPE: RNA
<213> ORGANISM: Artificial Sequences
<220> FEATURE:
<223> OTHER INFORMATION: Synthetic

<400> SEQUENCE: 5
auguacacua aacaugauga uauccgaaaa uga                              33

<210> SEQ ID NO 6
<211> LENGTH: 10
```

```
<212> TYPE: PRT
<213> ORGANISM: Artificial Sequences
<220> FEATURE:
<223> OTHER INFORMATION: Synthetic

<400> SEQUENCE: 6

Met Tyr Thr Lys Asp His Asp Ile Arg Lys
1               5                   10

<210> SEQ ID NO 7
<211> LENGTH: 10
<212> TYPE: PRT
<213> ORGANISM: Artificial Sequences
<220> FEATURE:
<223> OTHER INFORMATION: Synthetic

<400> SEQUENCE: 7

Lys Arg Ile Asp Asp His Lys Thr Tyr Met
1               5                   10
```